(12) United States Patent
Thompson et al.

(10) Patent No.: US 12,029,055 B2
(45) Date of Patent: Jul. 2, 2024

(54) OLED WITH HYBRID EMISSIVE LAYER

(71) Applicants: The University of Southern California, Los Angeles, CA (US); The Regents of the University of Michigan, Ann Arbor, MI (US)

(72) Inventors: Mark E. Thompson, Anaheim, CA (US); Abegail Tadle, Bakersfield, CA (US); Muazzam Idris, Los Angeles, CA (US); Karim El Roz, Los Angeles, CA (US); Daniel Sylvinson Muthiah Ravinson, Los Angeles, CA (US); Stephen R. Forrest, Ann Arbor, MI (US); Chan Ho Soh, Ann Arbor, MI (US)

(73) Assignees: The University of Southern California, Los Angeles, CA (US); The Regents of the University of Michigan, Ann Arbor, MI (US)

( * ) Notice: Subject to any disclaimer, the term of this patent is extended or adjusted under 35 U.S.C. 154(b) by 798 days.

(21) Appl. No.: 16/262,408

(22) Filed: Jan. 30, 2019

(65) Prior Publication Data
US 2019/0237694 A1    Aug. 1, 2019

Related U.S. Application Data

(60) Provisional application No. 62/623,764, filed on Jan. 30, 2018.

(51) Int. Cl.
*H10K 50/11*     (2023.01)
*C07D 233/58*    (2006.01)
(Continued)

(52) U.S. Cl.
CPC .......... *H10K 50/11* (2023.02); *C07D 233/58* (2013.01); *C07D 401/10* (2013.01); *C09K 11/06* (2013.01);
(Continued)

(58) Field of Classification Search
None
See application file for complete search history.

(56) References Cited

U.S. PATENT DOCUMENTS

| 4,594,413 | A | 6/1986 | Munavalli |
| 4,769,292 | A | 9/1988 | Tang |

(Continued)

FOREIGN PATENT DOCUMENTS

| CN | 104817540 A | * | 8/2015 |
| EP | 0650955 | | 5/1995 |

(Continued)

OTHER PUBLICATIONS

Liu et al., Journal of Materials Chemistry C, vol. 3, pp. 4394-4401. (Year: 2015).*

(Continued)

*Primary Examiner* — Dawn L Garrett
(74) *Attorney, Agent, or Firm* — Riverside Law LLP

(57) ABSTRACT

A hybrid emissive layer and OLED incorporating the same are provided. The hybrid emissive layer includes a first material having a triplet state energy level $T1_H$ and a singlet state energy level $S1_H$, a second material having a triplet state energy level $T1_F$ and a singlet state energy level $S1_F$; and a third material having a triplet state energy level $T1_P$ and a single state energy level $S1_P$, where $T1_F \geqslant T1_H$; $S1_F \leqslant S1_H$; and $T1_P < T1_H$.

17 Claims, 30 Drawing Sheets

Phenanthro[9,10-d]imidazoles (I1–I6).

(51) Int. Cl.
  *C07D 401/10* (2006.01)
  *C09K 11/06* (2006.01)
  *H10K 50/125* (2023.01)
  *H10K 85/30* (2023.01)
  *H10K 85/60* (2023.01)
  *H10K 101/00* (2023.01)
  *H10K 101/10* (2023.01)
  *H10K 101/30* (2023.01)

(52) U.S. Cl.
  CPC ......... *H10K 50/125* (2023.02); *H10K 85/322* (2023.02); *H10K 85/654* (2023.02); *H10K 85/6572* (2023.02); *C09K 2211/1018* (2013.01); *H10K 2101/10* (2023.02); *H10K 2101/27* (2023.02); *H10K 2101/30* (2023.02); *H10K 2101/90* (2023.02)

(56) References Cited

U.S. PATENT DOCUMENTS

| | | |
|---|---|---|
| 5,061,569 A | 10/1991 | Vanslyke |
| 5,247,190 A | 9/1993 | Friend |
| 5,703,436 A | 12/1997 | Forrest |
| 5,707,745 A | 1/1998 | Forrest |
| 5,834,893 A | 11/1998 | Bulovic |
| 5,844,363 A | 12/1998 | Gu |
| 6,013,982 A | 1/2000 | Thompson |
| 6,087,196 A | 7/2000 | Sturm |
| 6,091,195 A | 7/2000 | Forrest |
| 6,097,147 A | 8/2000 | Baldo |
| 6,278,237 B1 | 8/2001 | Campos |
| 6,294,398 B1 | 9/2001 | Kim |
| 6,303,238 B1 | 10/2001 | Thompson |
| 6,310,360 B1 | 10/2001 | Forrest |
| 6,337,102 B1 | 1/2002 | Forrest |
| 6,468,819 B1 | 10/2002 | Kim |
| 6,528,187 B1 | 3/2003 | Okada |
| 6,687,266 B1 | 2/2004 | Ma |
| 6,835,469 B2 | 12/2004 | Kwong |
| 6,921,915 B2 | 7/2005 | Takiguchi |
| 7,087,321 B2 | 8/2006 | Kwong |
| 7,090,928 B2 | 8/2006 | Thompson |
| 7,154,114 B2 | 12/2006 | Brooks |
| 7,250,226 B2 | 7/2007 | Tokito |
| 7,279,704 B2 | 10/2007 | Walters |
| 7,332,232 B2 | 2/2008 | Ma |
| 7,338,722 B2 | 3/2008 | Thompson |
| 7,393,599 B2 | 7/2008 | Thompson |
| 7,396,598 B2 | 7/2008 | Takeuchi |
| 7,431,968 B1 | 10/2008 | Shtein |
| 7,445,855 B2 | 11/2008 | Mackenzie |
| 7,534,505 B2 | 5/2009 | Lin |
| 7,968,146 B2 | 6/2011 | Wagner |
| 8,409,729 B2 | 4/2013 | Zeng |
| 8,777,291 B2 | 7/2014 | Mcneely |
| 2002/0034656 A1 | 3/2002 | Thompson |
| 2002/0134984 A1 | 9/2002 | Igarashi |
| 2002/0158242 A1 | 10/2002 | Son |
| 2003/0138657 A1 | 7/2003 | Li |
| 2003/0152802 A1 | 8/2003 | Tsuboyama |
| 2003/0162053 A1 | 8/2003 | Marks |
| 2003/0175553 A1 | 9/2003 | Thompson |
| 2003/0201415 A1 | 10/2003 | Hoag |
| 2003/0230980 A1 | 12/2003 | Forrest |
| 2004/0036077 A1 | 2/2004 | Ise |
| 2004/0124766 A1* | 7/2004 | Nakagawa .......... H01L 51/5234 313/504 |
| 2004/0137267 A1 | 7/2004 | Igarashi |
| 2004/0137268 A1 | 7/2004 | Igarashi |
| 2004/0174116 A1 | 9/2004 | Lu |
| 2004/0265628 A1* | 12/2004 | Wang ................. H10K 85/6572 546/64 |
| 2005/0025993 A1 | 2/2005 | Thompson |
| 2005/0058853 A1 | 3/2005 | Cosimbescu |
| 2005/0112407 A1 | 5/2005 | Ogasawara |
| 2005/0170204 A1 | 8/2005 | Vargas |
| 2005/0181232 A1 | 8/2005 | Ricks |
| 2005/0196638 A1* | 9/2005 | Son ...................... H01L 51/5016 428/690 |
| 2005/0208329 A1* | 9/2005 | Conley ................ C09K 11/06 428/690 |
| 2005/0211958 A1 | 9/2005 | Conley |
| 2005/0221120 A1 | 10/2005 | Owczarczyk |
| 2005/0227112 A1 | 10/2005 | Ise |
| 2005/0238919 A1 | 10/2005 | Ogasawara |
| 2005/0244673 A1 | 11/2005 | Satoh |
| 2005/0260441 A1 | 11/2005 | Thompson |
| 2005/0260449 A1 | 11/2005 | Walters |
| 2006/0006792 A1 | 1/2006 | Strip |
| 2006/0008670 A1 | 1/2006 | Lin |
| 2006/0158104 A1* | 7/2006 | Iijima ................. H01L 51/5016 313/504 |
| 2006/0202194 A1 | 9/2006 | Jeong |
| 2006/0240279 A1 | 10/2006 | Adamovich |
| 2006/0251923 A1 | 11/2006 | Lin |
| 2006/0263635 A1 | 11/2006 | Ise |
| 2006/0273714 A1* | 12/2006 | Forrest ................ H01L 51/5044 313/504 |
| 2006/0280965 A1 | 12/2006 | Kwong |
| 2007/0190359 A1 | 8/2007 | Knowles |
| 2007/0278938 A1 | 12/2007 | Yabunouchi |
| 2008/0015355 A1 | 1/2008 | Schafer |
| 2008/0018221 A1 | 1/2008 | Egen |
| 2008/0106190 A1 | 5/2008 | Yabunouchi |
| 2008/0124572 A1 | 5/2008 | Mizuki |
| 2008/0220265 A1 | 9/2008 | Xia |
| 2008/0286610 A1* | 11/2008 | Deaton ............... H01L 51/5016 428/704 |
| 2008/0297033 A1 | 12/2008 | Knowles |
| 2009/0008605 A1 | 1/2009 | Kawamura |
| 2009/0009065 A1 | 1/2009 | Nishimura |
| 2009/0017330 A1 | 1/2009 | Iwakuma |
| 2009/0030202 A1 | 1/2009 | Iwakuma |
| 2009/0039776 A1 | 2/2009 | Yamada |
| 2009/0045730 A1 | 2/2009 | Nishimura |
| 2009/0045731 A1 | 2/2009 | Nishimura |
| 2009/0101870 A1 | 4/2009 | Prakash |
| 2009/0108737 A1 | 4/2009 | Kwong |
| 2009/0115316 A1 | 5/2009 | Zheng |
| 2009/0165846 A1 | 7/2009 | Johannes |
| 2009/0167162 A1 | 7/2009 | Lin |
| 2009/0179554 A1 | 7/2009 | Kuma |
| 2010/0237334 A1 | 9/2010 | Ma |
| 2013/0026452 A1 | 1/2013 | Kottas |
| 2013/0119354 A1 | 5/2013 | Ma |
| 2014/0054564 A1 | 2/2014 | Kim |
| 2015/0318487 A1 | 11/2015 | Ito |
| 2016/0232265 A1* | 8/2016 | Thompson ............ H01L 51/002 |
| 2017/0229663 A1 | 8/2017 | Tsai |
| 2018/0053901 A1 | 2/2018 | Yoshida |
| 2019/0067589 A1 | 2/2019 | Yoon |
| 2019/0237694 A1 | 8/2019 | Thompson |
| 2020/0239456 A1 | 7/2020 | Thompson |
| 2020/0243772 A1 | 7/2020 | Thompson |
| 2020/0321540 A1 | 10/2020 | Yoshizaki |

FOREIGN PATENT DOCUMENTS

| | | |
|---|---|---|
| EP | 1238981 | 9/2002 |
| EP | 1340798 A2 | 9/2003 |
| EP | 1725079 | 11/2006 |
| EP | 1844108 A2 | 10/2007 |
| EP | 2034538 | 3/2009 |
| EP | 2551932 | 1/2013 |
| EP | 2977378 | 1/2016 |
| EP | 3276697 A1 | 1/2018 |
| JP | 200511610 | 1/2005 |
| JP | 2007123392 | 5/2007 |
| JP | 2007254297 | 10/2007 |
| JP | 2008074939 | 4/2008 |
| JP | 2010135467 | 6/2010 |
| KR | 20030071581 | 9/2003 |

(56) References Cited

FOREIGN PATENT DOCUMENTS

| | | |
|---|---|---|
| KR | 20060133566 | 12/2006 |
| KR | 20170131398 | 11/2017 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2004111066 A1 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |
| WO | 2008057394 A1 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010011390 A2 | 1/2010 |
| WO | 2010111175 | 9/2010 |
| WO | 2010126234 | 11/2010 |
| WO | WO-2012087955 A1 * | 6/2012 |
| WO | 201615840 A1 | 2/2016 |

OTHER PUBLICATIONS

Wang, B. et al., 2015. Pyridine-containing phenanthroimidazole electron-transport materials with electron mobility/energy-level trade-off optimization for highly efficient and low roll-off sky blue fluorescent OLEDs. Journal of Materials Chemistry C, 3(29), pp. 7709-7719. (Year: 2015).*

Zhu, Ze-Lin, et al. "Tuning electrical properties of phenanthroimidazole derivatives to construct multifunctional deep-blue electroluminescent materials." Journal of Materials Chemistry C 6.14 (2018): 3584-3592. (Year: 2018).*

Du, X. et al., (2017). Multifunctional Phenanthroimidazole Derivatives to Realize High-Performance Deep-Blue and White Organic Light-Emitting Diodes. Advanced Optical Materials, 5(23), 1700498. (Year: 2017).*

Machine translation of CN 104817540 A (Publication date: Aug. 2015). (Year: 2015).*

Chen, W. C., Zhu, Z. L., & Lee, C. S. (2018). Organic light-emitting diodes based on imidazole semiconductors. Advanced Optical Materials, 6(18), 1800258. (Year: 2018).*

Adachi et al., "Nearly 100% Internal Phosphorescent Efficiency in an Organic Light Emitting Device," J. Appl. Phys., vol. 90, No. 10, pp. 5048-5051 (2001).

Adachi, Chihaya et al., "High-Efficiency Red Electrophosphorescence Devices," Appl. Phys. Lett., 78(11):1622-1624 (2001).

Adachi, Chihaya et al., "Organic Electroluminescent Device Having a Hole Conductor as an Emitting Layer," Appl. Phys. Lett., 55(15): 1489-1491 (1989).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., "Highly Efficient Phosphorescent Emission from Organic Electroluminescent Devices," Nature, vol. 395, pp. 151-154 (1998).

Baldo et al., "Very high-efficiency green organic light-emitting devices based on electrophosphorescence," Appl. Phys. Lett., vol. 75, No. 3, 4-6 (1999).

Baldo, et al., "Very high-efficiency green organic light-emitting devices based on electrophosphorescence", Applied Physics Letters, Jul. 5, 1999,4 pp., vol. 75, No. 1, American Institute of Physics, Melville, NY, USA.

Gao, Zhiqiang et al., "Bright-Blue Electroluminescence From a Silyl-Substituted ter-(phenylenevinylene) derivative," Appl. Phys. Lett., 74(6):865-867 (1999).

Guo, Tzung-Fang et al., "Highly Efficient Electrophosphorescent Polymer Light-Emitting Devices," Organic Electronics, 1:15-20 (2000).

Hamada, Yuji et al., "High Luminance in Organic Electroluminescent Devices with Bis(10-hydroxybenzo[h]quinolinato)beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3,"Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185: Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kevin S. Huang, Makhluf J. Haddadin, Marilyn M. Olmstead, and Mark J. Kurth: "Synthesis and Reactions of Some Heterocyclic Azacyanines", J. Org. Chem., vol. 66,Feb. 1, 2001 (Feb. 1, 2001), pp. 1310-1315, XP002799306, DOI: 10.1021/jo001484k.

Kido, Junji et al.,"1,2,4-Triazole Derivative as an Electron Transport Layer in Organic Electroluminescent Devices," Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Kwong et al., "High Operational Stability of Electrophosphorescent Devices," Appl. Phys. Lett., vol. 81, No. 1, pp. 162-164 (2002).

(56) References Cited

OTHER PUBLICATIONS

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21):5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mariusz Tasior et al.: "An internal charge transfer-dependentsolvent effect in V-shaped azacyanines", Organic & Biomolecular Chemistry, vol. 13, No. 48, Jan. 1, 2015 (Jan. 1, 2015), pp. 11714-11720, XP055313516, ISSN: 1477-0520, DOI: 10 .1039/C5OBO1633A.

Mi, Bao-Xiu et al., "Thermally Stable Hole-Transporting Material for Organic Light-Emitting Diode: an Isoindole Derivative," Chem. Mater., 15(16):3148-3151 (2003).

Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,6-Bis(dinnesitylboryl)-2,2'-bithiophene and 5,5"-Bis(dimesitylbory1)-2,2':5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based On Silole Derivatives And Their Exciplexes," Organic Electronics, 4:113-121 (2003).

Paulose, Betty Marie Jennifer S, et al., "First Examples of Alkenyl Pyridines as Organic Ligands for Phosphorescent Iridium Complexes," Adv. Mater., 16(22):2003-2007 (2004).

Poopathy Kathirgamanathan et al., "Arylvinylene phenanthroline derivatives for electron transport in blue organic light emitting diodes", Organic Electronics, Elsevier, Amsterdam, NL, vol. 12, No. 4, doi:10.1016/J.ORGEL.2010.12.025, ISSN 1566-1199, (Dec. 31, 2010), pp. 666-676, (Jan. 18, 2011), XP028171608.

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91:209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Ostergard et al., "Langmuir-Blodgett Light-Emitting Diodes Of Poly(3-Hexylthiophene): Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-a]pyridine Ligands: Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8):1059-1064 (2005).

Van Slyke, S. A. et al., "Organic Electroluminescent Devices with Improved Stability," Appl. Phys. Lett, 69(15 ):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., "A Novel Class of Phosphorescent Gold(III) Alkynyl-Based Organic Light-Emitting Devices with Tunable Colour," Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Database Reaxys [Online] Elsevier; Jan. 1, 1986 (Jan. 1, 1986), Munavalli S: "Synthesis of Novel Azapyridocyanines", XP055935941, Database accession No. XRN = 6456896.

Database Reaxys [Online] Elsevier; Jan. 1, 1991 (Jan. 1, 1991), Kaplan G: "Journal of general chemistry of the USSR; vol. 61; (1991); p. 1671-1675", XP055935944, Database accession No. XRN = 16038091.

Golden, et al., J. Org. Chem. 2017, 82, 7215-7222.

Liu, Yi et al: "Optical properties and mechanofluorochromism of new BODIPY dyes based on the pyridine-pyrimidine hybrid structure", Dalton Transactions, vol. 46, No. 31, Jan. 1, 2017 (Jan. 1, 2017), pp. 10332-10338, XP055935942, Cambridge ISSN: 1477-9226, DOI: 10.1039/C7DT02259J.

Sun, Lin et al: "Geometric and Electronic Structures of Boron(III)-Cored Dyes Tailored by Incorporation of Heteroatoms into Ligands", Chemistry—An Asian Journal, vol. 10, No. 3, Mar. 1, 2015 (Mar. 1, 2015), pp. 709-714, XP055935943, ISSN: 1861-4728, DOI: 10.1002/asia.201403272.

Tadle, et al., Tuning the Photophysical and Electrochemical Properties of Aza-Boron-Dipyridylmethenes for Fluorescent Blue OLEDs Advanced Functional Materials, vol. 31, pp. 2101175-2101175, 2001.

Madhu, Difference Between Excimer and Exiplex, May 24, 2022, pp. 1-8.

\* cited by examiner

X = NR, O, S
$R_n$ = H, Alkyl/Aryl, OR, $NR_2$, CN, F, Cl, Br, I

R = Me, Mesityl

Synthetic route of azaDiPYR derivatives.

Synthetic route to produce oxazolone derivatives.

Normalized absorption (solid lines) and emission (dashed lines) spectra for oxazolone derivatives in $CH_2Cl_2$ (air-equilibrated).

Alternative synthesis of 4P-NPD

Singlet sensing (DCM2)

Singlet + Triplet sensing (PQIr)

Singlet + Triplet sensing (PQIr)

@100 mA/cm$^2$

Distribution of relevant design parameters computed for the DIPYR library.

Distribution of relevant design parameters computed for the α-DIPYR library.

Library of synthesized azaDIPYR compounds used as fluorescent blue dopant which were studied for WOLED application.

Absorption and emission spectra of aD (left) and α-aD (right) taken in 2-methyltetrahydrofuran.

Normalized spectra of absorption (dash), fluorescence (solid) at 298 K, phosphorescence emission at Normalized spectra of absorption (dash), fluorescent emission at 298 K in solution (solid), and fluorescent emission at 298 K in solid (dash dot) for cationic aCarD and α-aCarD in ethanol/methanol mixture in 2:1.

Different ways the azaDIPYR core can be modified either by substitution with electron donor or withdrawing group. These are examples and are not limiting. Additionally, the core can also be substituted with different atoms in the core which has been shown to be ideal fluorophores based on DFT calculations.

carDIPYR structures of interest. These are examples and are not limiting. Asymmetric versions can also be synthesized by our methods. X: anionic moiety such as COO- but not limiting. R: aliphatic moiety such as -CH$_3$, -CN, iPr, etc. Ar: aromatic moiety such as phenyl or substituted phenyl group like mesityly, tolyl, or xylyl.

Synthesis of phenanthro[9,10-d]imidazoles

Phenanthro[9,10-*d*]imidazoles (I1–I6).

Photoluminescence spectra of I1 – I6

Cyclic voltammetry of phenanthro[9,10-*d*]imidazoles

OLED characteristics of phenanthro[9,10-*d*]imidazoles as neat emitters

OLED characteristics of α-aD with phenanthro[9,10-*d*]imidazoles as hosts

WOLED characteristics of α-aD with I5 as a host material

WOLED characteristics of I5 as a neat emitter

OLED WITH HYBRID EMISSIVE LAYER

CROSS-REFERENCE TO RELATED APPLICATIONS

This application claims the priority benefit of U.S. Provisional Patent Application No. 62/623,764, filed Jan. 30, 2018, the disclosure of which is incorporated by reference in its entirety.

STATEMENT REGARDING FEDERALLY SPONSORED RESEARCH OR DEVELOPMENT

This invention was made with government support under Grant No. DE-EE0007077 and DE-EE0008244 awarded by the Department of Energy. The government has certain rights in the invention.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an embodiment, an organic light emitting diode/device (OLED) is also provided. The OLED can include an anode, a cathode, and an organic layer, disposed between the anode and the cathode. According to an embodiment, the organic light emitting device is incorporated into one or more device selected from a consumer product, an electronic component module, and/or a lighting panel.

In an embodiment, a hybrid emissive layer for use in a device such as an OLED and, more specifically, for use in a white-emitting OLED (WOLED) is provided, which includes a first material having a triplet state energy level $T1_H$ and a singlet state energy level $S1_H$; a second material having a triplet state energy level $T1_F$ and a singlet state energy level $S1_F$; and a third material having a triplet state energy level Tip and a single state energy level $S1_P$, where $T1_F \geq T1_H$, $S1_F \leq S1_H$, and $T1_P < T1_H$. The second material may be a fluorescent emissive material such as a fluorescent dopant and/or the third material may be a phosphorescent emissive material such as a phosphorescent dopant.

In one embodiment, the primary emission from the OLED occurs from the first material. In a most preferred embodiment, all the emission from the OLED occurs from the first material. The OLED also may include a second emissive layer, which also may include the first material. In an embodiment, the first and third materials may be or include the same material.

In some embodiments, the singlet and triplet energy levels of the materials may be within specific ranges, or may exhibit specific relationships. For example, $T1_H$ may be at least 0.1 eV greater than $T1_F$; $T1_F$ may be at least 0.1 eV greater than $T1_H$; $S1_H$ may be at least 3.5 eV; $T1_H$ may be 2.4 eV to 2.6 eV; and/or $T1_P$ is 1.7 to 2.5 eV, or any combination thereof. Furthermore, the energy gap between $S1_F$ and $T1_F$ may be 0.05 eV to 0.8 eV or 0.1 eV to 0.8 eV. In some embodiments, the fluorescent emissive dopant may have a fluorescence efficiency of at least 60%.

In one embodiment, the second material is selected from compounds selected from the group consisting of Formula A, Formula B, Formula C, and Formula D:

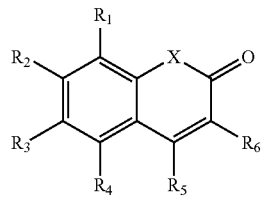

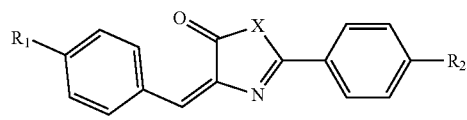

X = NR, O, S
$R_n$ = H, Alkyl/Aryl, OR, $NR_2$, CN, F, Cl, Br, I.

In another embodiment, groups $R_1$ to $R_{11}$ for the compounds of Formula A, Formula B, Formula C, and Formula D are independently hydrogen or a substituent selected from the group consisting of deuterium, halogen, alkyl, cycloalkyl, heteroalkyl, heterocycloalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof. Moreover, if X is NR, then R is selected from the group consisting of hydrogen, deuterium, alkyl, cycloalkyl, heteroalkyl, heterocycloalkyl, arylalkyl, silyl, aryl, heteroaryl, and combinations thereof.

In some instances, the group substituents $R_1$ to $R_{11}$ are independently selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the group substituents $R_1$ to $R_{11}$ are independently selected from the group consisting of deuterium, fluorine, alkyl, cycloalkyl, alkoxy, aryloxy, amino, silyl, aryl, heteroaryl, and sulfanyl.

In an embodiment, the first material may include a compound selected from the group consisting of:

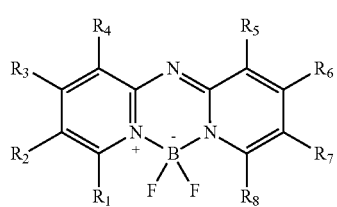

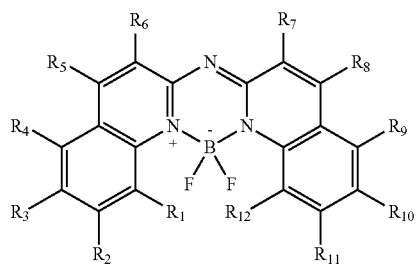

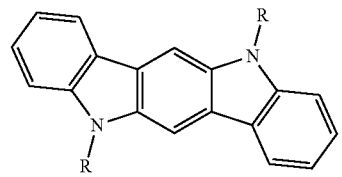

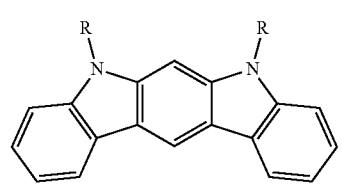

-continued

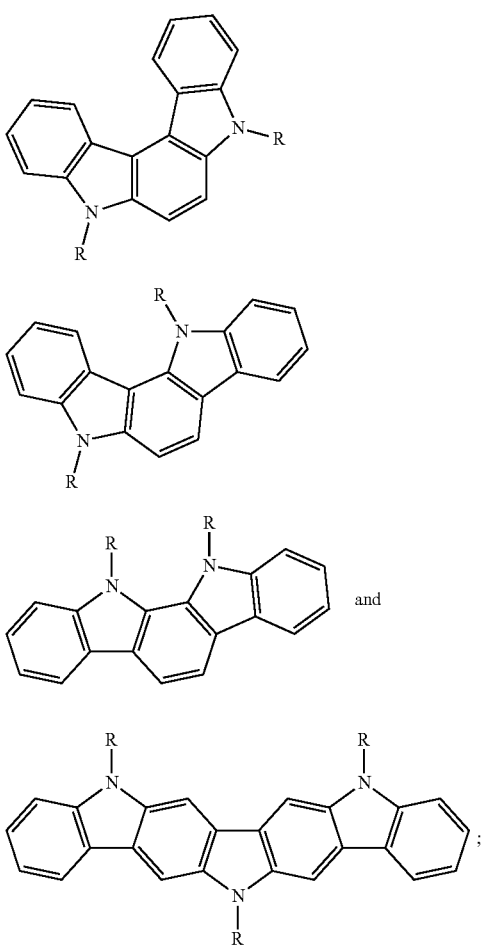

wherein R is selected from the group consisting of hydrogen, deuterium, alkyl, cycloalkyl, heteroalkyl, heterocycloalkyl, arylalkyl, silyl, aryl, heteroaryl, and combinations thereof.

In an embodiment, the first material may include a compound selected from the group consisting of:

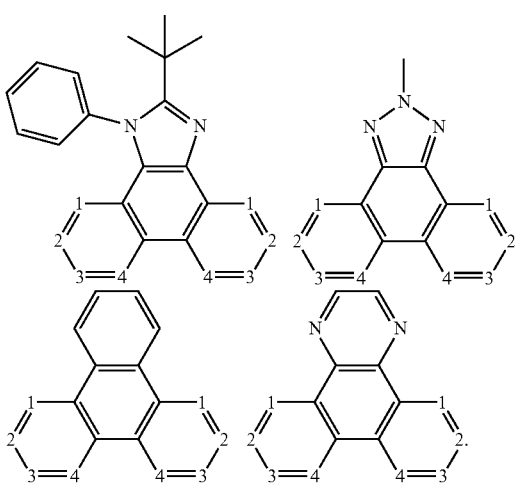

In each of the first material compounds above, ring members 1 to 4 are independently selected from $CR^P$ or N, wherein no more than two of ring members 1 to 4 are N; wherein $R^P$ is independently hydrogen or a substituent selected from the group consisting of deuterium, halogen, alkyl, cycloalkyl, heteroalkyl, heterocycloalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof. In some instances, the group substituents are independently selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof. In an embodiment, the second material may emit light with a peak wavelength of 400 nm to 510 nm.

In an embodiment, a compound is provided of Formula I:

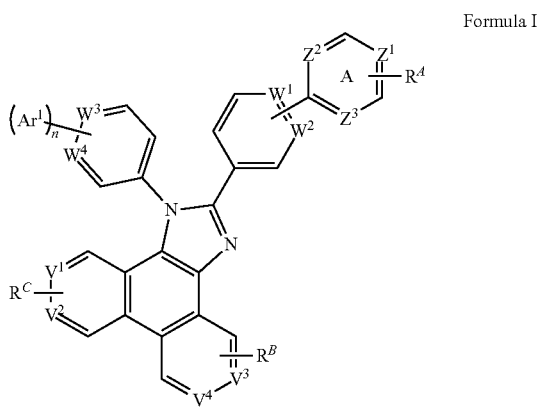

Formula I wherein
$W^1$ and $W^2$ are independently selected from C, CH, or N; wherein one of $W^1$ or $W^2$ is C that is substituted with Ring A;
$W^3$ and $W^4$ are independently selected from C, $CR^W$, or N, and n is 0 or 1, wherein if n is 1 then one of $W^3$ or $W^4$ is C that is substituted with $Ar^1$;
$Z^1$, $Z^2$, and $Z^3$ are independently selected from $CR^A$ or N, and at least one of $Z^1$, $Z^2$, or $Z^3$ is N;
$V^1$ and $V^2$ are independently selected from $CR^C$ or N;
$V^3$ and $V^4$ are independently selected from $CR^B$ or N; and
$Ar^1$ is selected from an optionally substituted aryl, or an optionally substituted heteroaryl;
$R^W$ is independently selected from the group consisting of hydrogen, deuterium, alkyl, cycloalkyl, alkoxy, aryloxy, amino, silyl, heterocyclic, aryl, heteroaryl, nitrile, isonitrile, and combinations thereof;
each $R^A$ is independently hydrogen or a substituent selected from the group consisting of deuterium, alkyl, cycloalkyl, alkoxy, aryloxy, amino, silyl, heterocyclic, aryl, heteroaryl, nitrile, isonitrile, and combinations thereof; or optionally, two adjacent $R^A$ join to form a fused aromatic ring, which is optionally substituted;
$R^B$ and $R^C$ independently represent from mono substitution to the maximum possible number of substitution, or no substitution; and
each $R^B$ and $R^C$ is independently hydrogen or a substituent selected from the group consisting of deuterium, alkyl, cycloalkyl, alkoxy, aryloxy, amino, silyl, heterocyclic, aryl, heteroaryl, nitrile, isonitrile, and combinations thereof, or optionally, two adjacent $R^B$ or $R^C$ join to form a fused aromatic ring, which is optionally substituted.

In an embodiment, the compound may be selected from the group consisting of
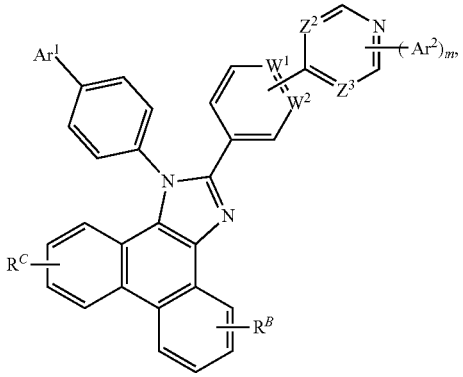
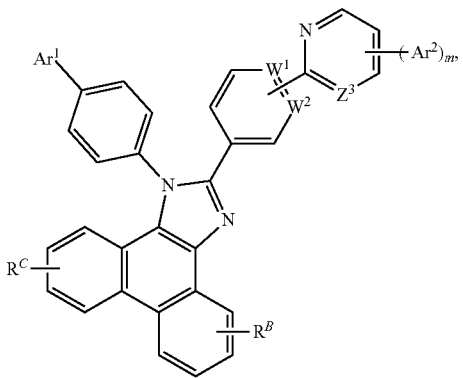
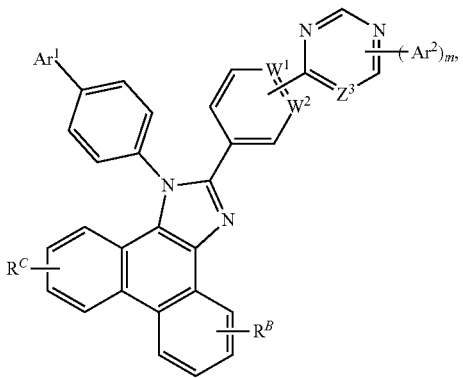
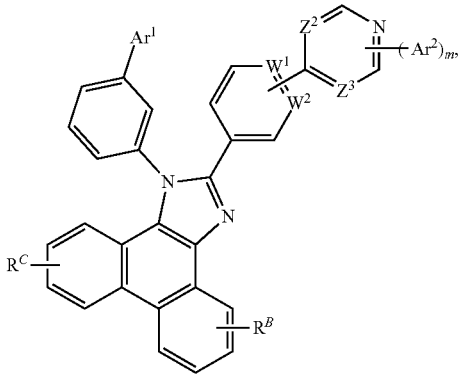
-continued
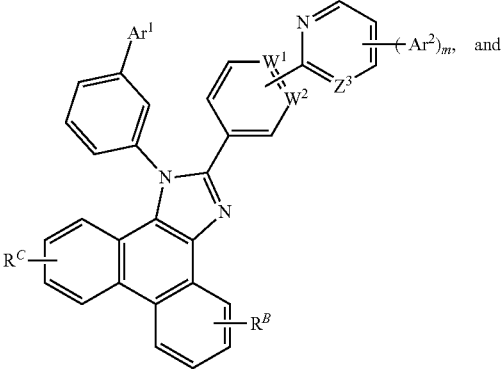
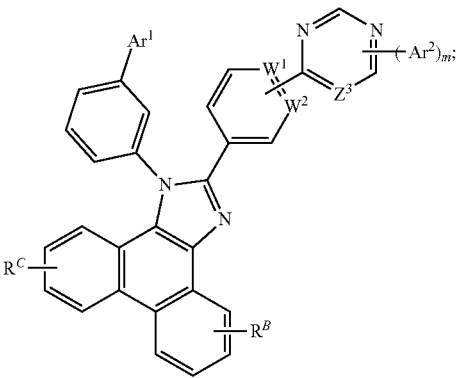
wherein m is 0 or 1, and Ar² is selected aryl or heteroaryl, each of which is optionally substituted.
In an embodiment, Ar¹ and Ar² may be independently selected from the group consisting of
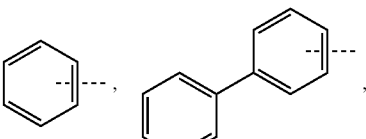
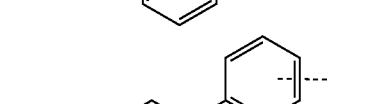
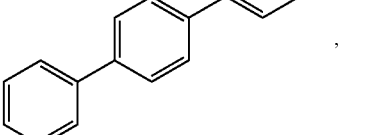
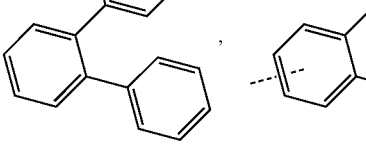

-continued

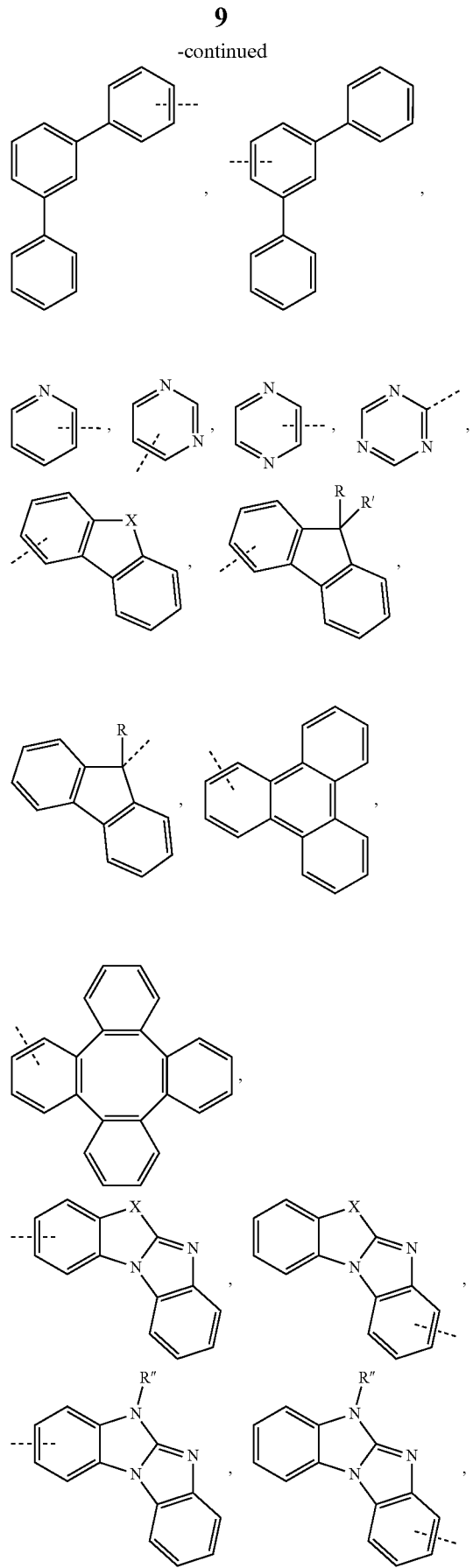

-continued and combinations thereof, or any one aza variant thereof, wherein X is selected from O, S, or Se;

R, R', and R" are independently selected from the group consisting of hydrogen, deuterium, alkyl, cycloalkyl, heteroalkyl, amino, silyl, alkynyl, aryl, heteroaryl, and combinations thereof; and the dotted line represents attachment to the Ring A.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998 ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
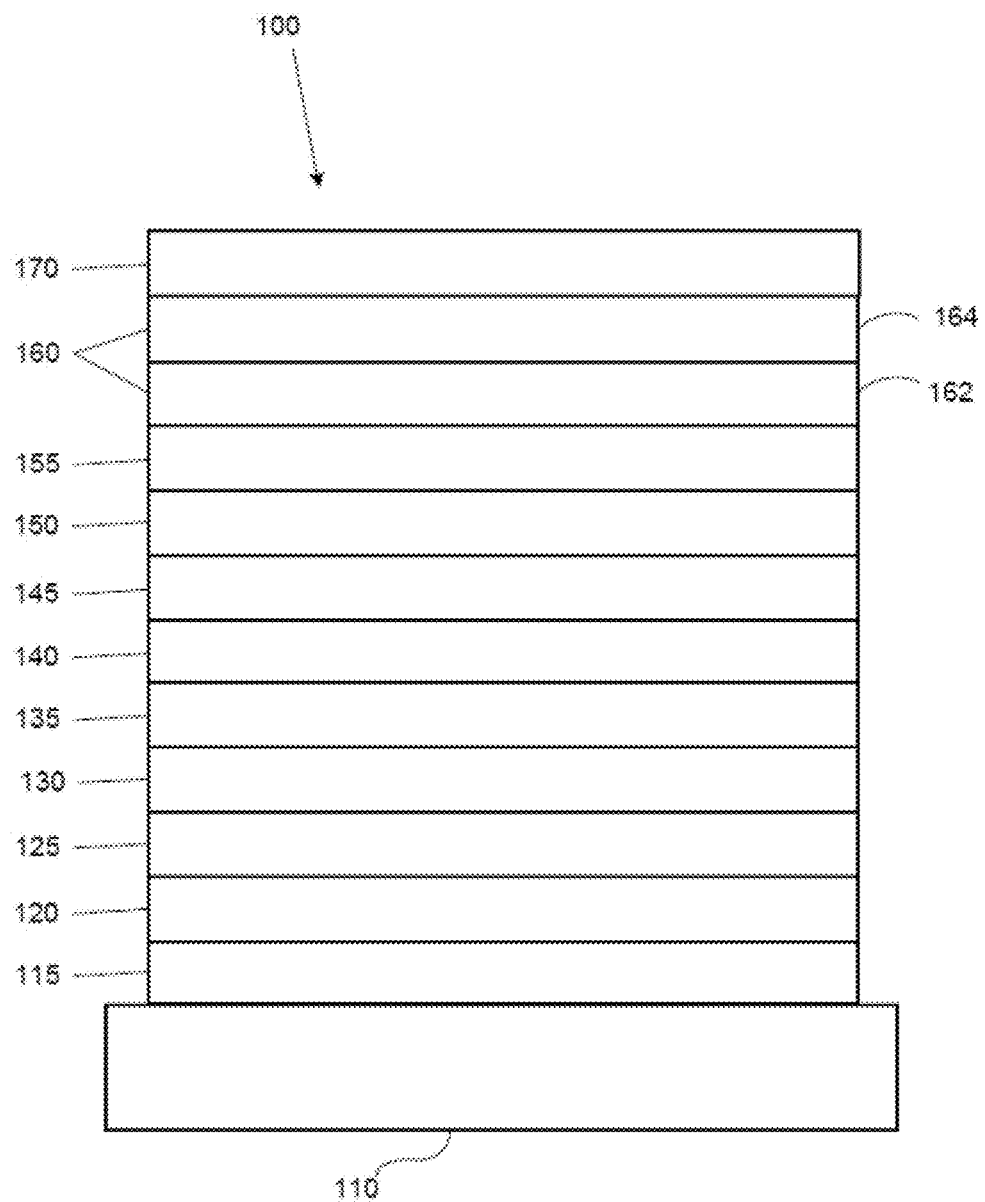
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
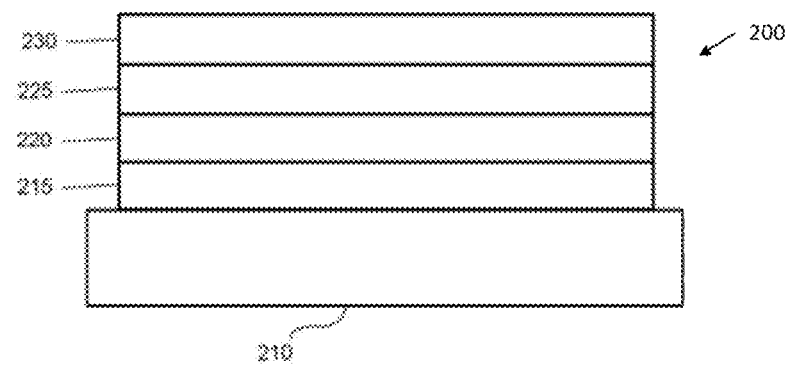
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed wider anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as inkjet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, mobile phones, tablets, phablets, personal digital assistants (PDAs), wearable devices, laptop computers, digital cameras, camcorders, viewfinders, microdisplays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 C to 30 C, and more preferably at room temperature (20-25 C), but could be used outside this temperature range, for example, from −40 C to 80 C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," or "halide" as used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —O$R_s$ radical.

The terms "sulfanyl" or "thio-ether" are used interchangeably and refer to a —S$R_s$ radical.

The term "sulfinyl" refers to a —S(O)—$R_s$ radical.

The term "sulfonyl" refers to a —$SO_2$—$R_s$ radical.

The term "phosphino" refers to a —P($R_s$)$_3$ radical, wherein each $R_s$ can be same or different.

The term "silyl" refers to a —Si($R_s$)$_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and Spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si and Se, preferably, O, S or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si and Se, preferably, O, S or N. Hetero-aromatic cyclic radicals may be used interchangeably with heteroaryl. Preferred hetero-non-aromatic cyclic groups are those containing 3 to 7 ring atoms, which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring hetero-aromatic groups and polycyclic aromatic ring systems that include at least one heteroatom. The heteroatoms include, but are not limited to O, S, N, P, B, Si and Se. In many instances, O, S or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted or substituted with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (Reviews) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments of the emissive region, the emissive region further comprises a host.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be an inorganic compound.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Various materials may be used for the various emissive and non-emissive layers and arrangements disclosed herein. Examples of suitable materials are disclosed in U.S. Patent Application Publication No. 2017/0229663, which is incorporated by reference in its entirety.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

HIL/HTL:

A hole injecting/transporting material to be used in the present invention is not particularly limited, and any compound may be used as long as the compound is typically used as a hole injecting/transporting material.

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples, of the host material are not particularly limited, and any metal complexes or organic compounds may be used as long as the triplet energy of the host is larger than that of the dopant. Any host material may be used with any dopant so long as the triplet criteria is satisfied.

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

ETL:

An electron transport layer (ETL) may include a material capable of transporting electrons. The electron transport layer may be intrinsic (undoped), or doped. Doping may be used to enhance conductivity. Examples of the ETL material are not particularly limited, and any metal complexes or organic compounds may be used as long as they are typically used to transport electrons.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

White OLEDs (or WOLEDs) with stacked multiple emissive layers are known and have been reported to produce white light, particularly, for commercial and residential lighting applications. See, for example, U.S. Pub. No. 2006/0006792 to Strip, and U.S. Pat. No. 8,777,291, assigned to Universal Display Corporation. In the UDC '291 patent, calculations showed that the light emitted for a stacked white OLED is a function of both the wavelength and the source position of the individual light emitting layers.

Results indicate that R, G, and B sub-elements, arranged in different orders, have different extraction efficiencies and thus yield different color temperature and color rending indices (CRI) with other parameters staying the same. The emitting layer order of B-G-R (with R adjacent to the ITO anode) is said to lead to an optimal color balance. Although many of such WOLEDs to exhibit high quantum efficiencies (60-70%) and luminous power efficiencies approaching 150 lm/W at brightnesses of 500-1000 cd/m², device performance often falls short of the desired goal, particularly, in terms of device stability or lifetime. One issue arises from a need to improve upon the relatively short operational lifetime of blue phosphorescent emitter dopants, and a consequent loss of color stability for the device.

In 2006, research produced a novel WOLED architecture that minimized many of the shortcomings of an all-phosphorescent OLED resulting in a high efficiency and long lived WOLED. The device employed a fluorescent-emitting dopant to harness all electrically generated high energy singlet excitons for blue emission, and phospherescent dopants to harvest the remainder of lower-energy triplet excitons for green, red, or yellow emission. Such a structure takes advantage of the fortuitous connection between the proportion of singlets dictated by spin statistics (i.e., one singlet vs. three triplets are produced by electrical excitation) and the roughly 25% contribution of blue to the perceived white light spectrum. The 25:75 spin branching ratio of blue to green+red conforms naturally to the visible spectrum, allowing for WOLEDs that have high color rendering indices (CRIs). Resonant energy transfer from both the host singlet and triplet energy levels minimizes exchange energy losses for both singlet and triplet exciton transfer from the host to each of the dopants, thereby maximizing device power efficiency while maintaining the potential for unity internal quantum efficiency (IQE). This approach has the further advantages of a stable white balance with current, a high efficiency at high brightness due to reduced geminate exciton recombination, and an enhanced lifetime due to the combined use of a stable fluorescent blue, and long lived phosphorescent green and red dopants in a single emissive region. Subsequent research has determined that further improvements and advances in OLED and WOLED technology may be achieved by selecting materials for use in the OLED that have specific energy level relationships.

Figure 3:
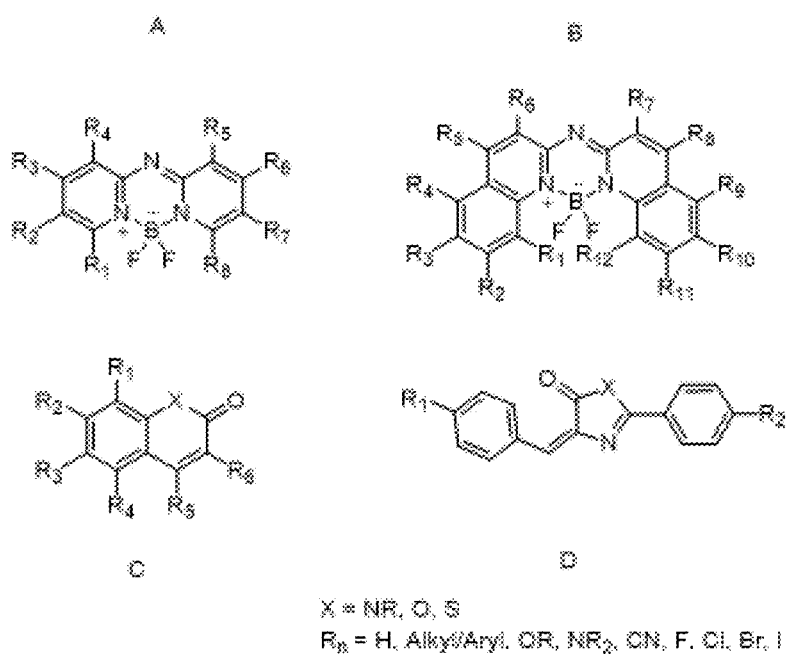
FIG. 3 shows the core structure libraries for fluorescent dopant materials that have been analysed as disclosed herein.

To do so, Density Functional Theory (DFT) calculations may be employed to screen through large libraries of compounds based on critical parameters such as $S_1$, $T_1$, HOMO/LUMO energies, and the $S_1$-$T_1$ gap ($\Delta S_1/T_1$) to inform and accelerate the materials discovery process. FIG. 3 shows the core structure libraries for fluorescent dopant materials that have been analysed as disclosed herein.

All DFT calculations were performed at the B3LYP/6-31G** level using the Materials Science Suite developed by Schrödinger. LLC. The goal was to identify blue fluorescent dopant materials ("fl-dopants") that have a relatively small $\Delta S_1/T_1$ (for example, preferably not greater than 0.4 eV) and/or host materials with relatively large $\Delta S_1/T_1$ such that efficient collection of singlet excitons at the fl-dopant and triplet excitons on the phosphorescent dopant materials ("ph-dopants") is simultaneously possible.

The DFT calculations on the fl-dopant libraries described herein indicate that the coumarin (C) and azlactone (D) based structures have rather large $\Delta S_1/T_1$ due to significant HOMO/LUMO overlap, thereby disqualifying them. The relevant data are provided in Tables 1.1a and 1.1b. The calculations also indicate that the Aza-DIPYR structures (A) may suffer from the existence of a close-lying $T_2$ state relative to the $S_1$ state that could potentially quench fluorescence on account of fast symmetry-allowed ISC as reported for a similar dye motif. It has also been found that benzannulation could potentially mitigate this problem by pushing the $T_2$ state above the $S_1$ state which has been found to be true for the Aza-alpha-DIPYR structures (B). It is also worth noting that the singlet excited states of the Aza-DIPYR/Alpha-Aza-DIPYR systems have significant multi-reference character that lead to an overestimation of the DFT computed $S_1$ energy by approx. 0.44 eV and warrant further investigation using multi-reference methods. A summary of the DFT calculated parameters on all the fl-dopants is shown in Tables 1.1a-1.1d.

TABLE 1.1a

DFT calculated properties for coumarin (C) based dye structures.

| | | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|---|
| C-1 | H₂N-coumarin | 3.97 | 312 | 2.59 | 479 | −5.21 | −1.90 | 1.38 |
| C-2 | Me₂N-coumarin | 3.77 | 329 | 2.52 | 492 | −5.01 | −1.94 | 1.25 |
| C-3 | Me₂N-N-methylquinolinone | 3.88 | 320 | 2.67 | 465 | −4.93 | −1.61 | 1.21 |
| C-4 | HO-coumarin | 4.20 | 295 | 2.71 | 457 | −5.82 | −2.09 | 1.49 |

TABLE 1.1a-continued

DFT calculated properties for coumarin (C) based dye structures.

| | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| C-5 | 4.11 | 302 | 2.84 | 436 | −5.55 | −1.65 | 1.27 |

TABLE 1.1b

DFT calculated properties for azlactone (D) based dye structures.

| | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| JF-1 | 3.34 | 371 | 1.77 | 701 | −5.70 | −2.90 | 1.57 |
| JF-2 | 4.01 | 309 | 2.13 | 581 | −6.00 | −2.55 | 1.88 |
| JF-3 | 3.25 | 382 | 1.75 | 710 | −5.40 | −2.75 | 1.50 |

TABLE 1.1b-continued
DFT calculated properties for azlactone (D) based dye structures.
| | | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|---|
| JF-4 | 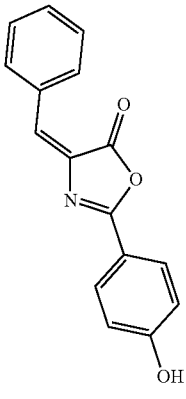 [SMILES: O=C1OC(c2ccc(O)cc2)=N/C1=C/c1ccccc1] | 3.22 | 385 | 1.74 | 711 | −5.46 | −2.83 | 1.48 |
| JF-5 | 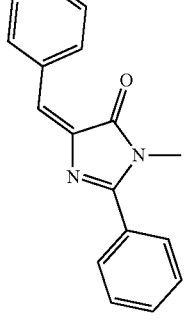 | 3.20 | 387 | 1.68 | 738 | −5.41 | −2.67 | 1.52 |
| JF-6 | 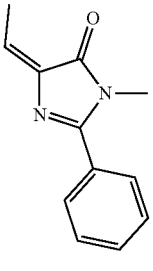 | 3.72 | 334 | 2.21 | 560 | −5.48 | −2.44 | 1.51 |
| JF-7 | 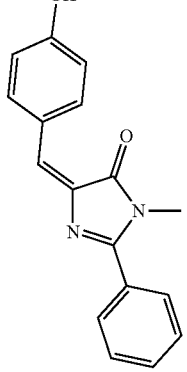 | 3.15 | 393 | 1.67 | 742 | −5.17 | −2.53 | 1.48 |

TABLE 1.1b-continued

DFT calculated properties for azlactone (D) based dye structures.

|  | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| JF-8 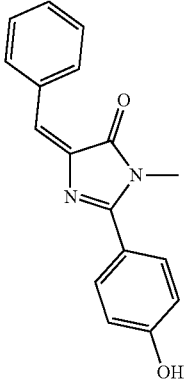 | 3.15 | 393 | 1.67 | 744 | −5.23 | −2.60 | 1.48 |

TABLE 1.1c

DFT calculated properties for mono-substituted Aza-alpha-DIPYR structures.

|  | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| AAD-OMe-5 | 2.81 | 441 | 2.50 | 496 | −5.51 | −1.85 | 0.31 |
| AAD-F-5 | 2.79 | 444 | 2.47 | 503 | −5.73 | −2.11 | 0.32 |
| AAD-OMe-4 | 2.76 | 449 | 2.43 | 511 | −5.53 | −1.94 | 0.33 |
| AAD-F-4 | 2.75 | 450 | 2.41 | 515 | −5.74 | −2.16 | 0.34 |
| AAD-F-1 | 2.74 | 452 | 2.39 | 520 | −5.67 | −2.10 | 0.36 |
| AAD-F-2 | 2.73 | 454 | 2.39 | 518 | −5.70 | −2.16 | 0.34 |
| AAD-F-6 | 2.71 | 457 | 2.34 | 529 | −5.71 | −2.20 | 0.37 |
| AAD-CN-3 | 2.69 | 460 | 2.37 | 524 | −5.99 | −2.49 | 0.33 |
| AAD-F-3 | 2.68 | 462 | 2.34 | 530 | −5.67 | −2.17 | 0.34 |
| AAD-OMe-2 | 2.68 | 463 | 2.37 | 524 | −5.47 | −1.98 | 0.31 |
| AAD-OMe-1 | 2.68 | 463 | 2.35 | 527 | −5.42 | −1.90 | 0.32 |
| AAD-OMe-6 | 2.66 | 466 | 2.31 | 536 | −5.45 | −1.99 | 0.35 |
| AAD-CN-1 | 2.65 | 468 | 2.34 | 531 | −5.87 | −2.40 | 0.31 |
| AAD-CN-4 | 2.64 | 470 | 2.33 | 533 | −5.97 | −2.51 | 0.31 |
| AAD-CN-2 | 2.63 | 471 | 2.33 | 533 | −5.97 | −2.49 | 0.30 |
| AAD-CN-6 | 2.62 | 473 | 2.35 | 527 | −5.97 | −2.48 | 0.27 |
| AAD-OMe-3 | 2.58 | 480 | 2.26 | 548 | −5.40 | −2.01 | 0.32 |
| AAD-CN-5 | 2.46 | 504 | 2.12 | 584 | −5.97 | −2.70 | 0.34 |

TABLE 1.1d

DFT calculated properties for mono-substituted Aza-alpha-DIPYR structures.

| | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| AAD-(OMe)2-5-5 | 2.92 | 425 | 2.67 | 465 | −5.41 | −1.62 | 0.25 |
| AAD-(F)2-5-5 | 2.85 | 434 | 2.56 | 485 | −5.84 | −2.14 | 0.30 |
| AAD-(OMe)2-4-4 | 2.79 | 444 | 2.47 | 502 | −5.45 | −1.81 | 0.33 |
| ADD-(F)2-4-4 | 2.78 | 446 | 2.43 | 510 | −5.86 | −2.26 | 0.35 |
| AAD-(F)2-1-1 | 2.77 | 448 | 2.39 | 518 | −5.72 | −2.13 | 0.37 |
| AAD-(F)2-2-2 | 2.74 | 453 | 2.40 | 516 | −5.78 | −2.25 | 0.34 |
| AAD-(F)2-6-6 | 2.68 | 462 | 2.30 | 540 | −5.80 | −2.34 | 0.39 |
| AAD-(OMe)2-1-1 | 2.68 | 463 | 2.35 | 529 | −5.25 | −1.71 | 0.33 |
| AAD-(CN)2-3-3 | 2.66 | 466 | 2.36 | 525 | −6.35 | −2.89 | 0.30 |
| AAD-(OMe)2-2-2 | 2.65 | 468 | 2.36 | 525 | −5.36 | −1.90 | 0.29 |
| AAD-(F)2-3-3 | 2.64 | 470 | 2.30 | 539 | −5.73 | −2.28 | 0.34 |
| AAD-(CN)2-6-6 | 2.64 | 470 | 2.37 | 523 | −6.28 | −2.79 | 0.27 |
| AAD-(OMe)2-6-6 | 2.64 | 470 | 2.25 | 550 | −5.31 | −1.90 | 0.38 |
| AAD-(CN)2-4-4 | 2.62 | 473 | 2.31 | 536 | −6.31 | −2.87 | 0.31 |
| AAD-(CN)2-1-1 | 2.62 | 473 | 2.35 | 527 | −6.11 | −2.64 | 0.27 |
| AAD-(CN)2-2-2 | 2.62 | 474 | 2.34 | 531 | −6.30 | −2.83 | 0.28 |
| AAD-(OMe)2-3-3 | 2.49 | 498 | 2.19 | 567 | −5.25 | −1.95 | 0.31 |

Figure 4:
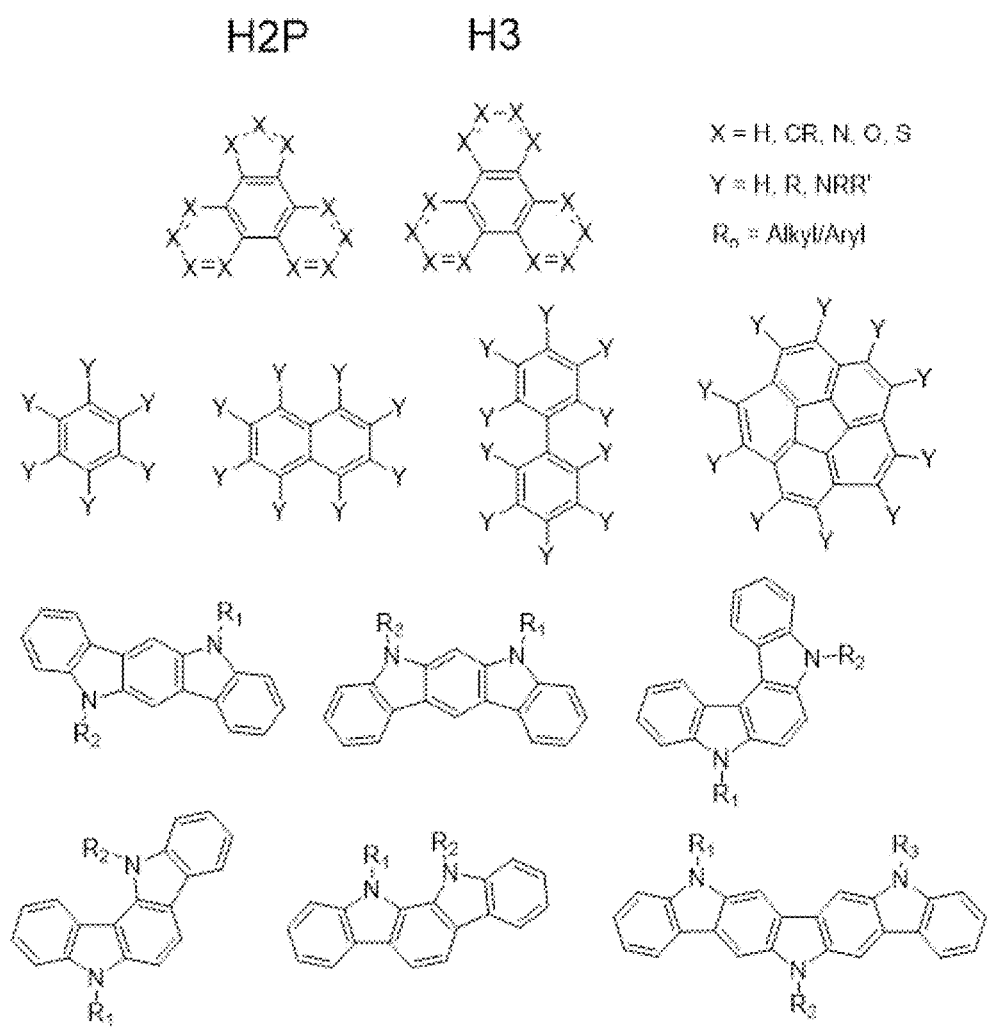
FIG. 4 shows the core structure libraries for host materials according to embodiments disclosed herein.
Figure 5:
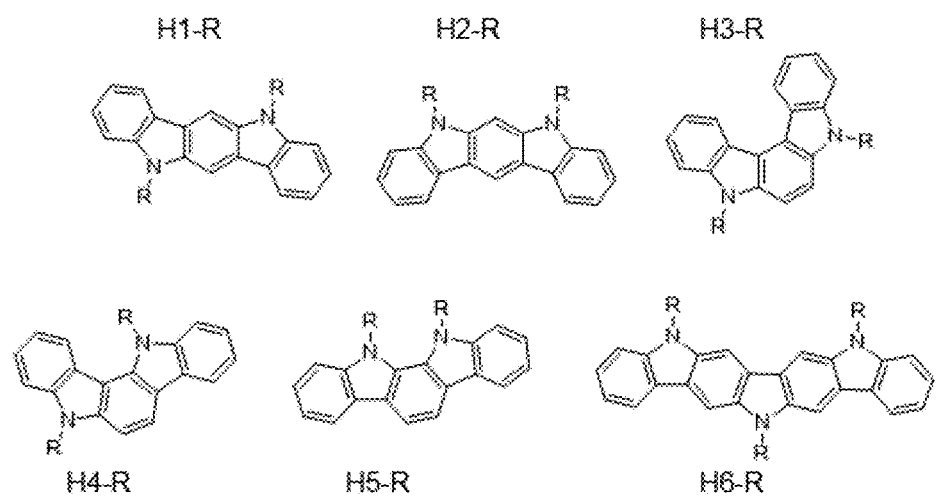
FIG. 5 shows indolo-carbazole systems with mesityl substitutions on the nitrogen atoms according to embodiments disclosed herein.

DFT calculations have also been used to identify several prospective host materials across the library shown in FIG. 4, which satisfy the previously-described criteria. DFT calculations were performed on synthetically tractable sub-libraries of indolo-carbazole based materials, H2Ps, H3s, corannulene based structures among others. Among the indolo-carbazole based structures, several promising candidates with high $\Delta S_1/T_1$ and $T_1$ in the ideal range of 2.4-2.6 eV have been identified and are summarized in Table 2.1a. However, a dramatic red-shifting (~0.3 eV) of the $T_1$ state has been observed in the past in the neat solid for several host materials, primarily in the H2P/H3-based systems. It remains to be seen if this is also the case in the indolo-carbazole systems. One way to mitigate this issue may be to add bulky groups onto the core structure, thus hampering effective stacking of the π cores. Therefore, structures with mesityl substitutions on the nitrogen atoms as shown in FIG. 5 have also been explored as described in further detail herein.

TABLE 2.1a

DFT calculated properties for indolo-carbazole based structures.

| | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| H1-mes | 3.30 | 376 | 2.77 | 448 | −4.80 | −1.37 | 0.53 |
| H2-mes | 3.72 | 333 | 3.06 | 405 | −4.97 | −1.12 | 0.66 |
| H3-mes | 3.41 | 364 | 2.84 | 437 | −4.82 | −1.33 | 0.57 |
| zH4-mes | 3.77 | 329 | 3.30 | 376 | −4.96 | −0.96 | 0.47 |
| H5-mes | 3.64 | 341 | 3.20 | 388 | −4.93 | −1.21 | 0.44 |
| H6-mes | 2.93 | 423 | 2.49 | 498 | −4.60 | −1.53 | 0.44 |
| H1-Me | 3.30 | 376 | 2.65 | 468 | −4.68 | −1.43 | 0.65 |
| H2-Me | 3.73 | 332 | 2.83 | 438 | −4.85 | −1.16 | 0.90 |
| H3-Me | 3.39 | 366 | 2.69 | 461 | −4.69 | −1.40 | 0.70 |
| H4-Me | 3.71 | 334 | 2.94 | 422 | −4.87 | −1.11 | 0.77 |
| H5-Me | 3.62 | 343 | 2.92 | 425 | −5.15 | −1.75 | 0.70 |

Figure 6:
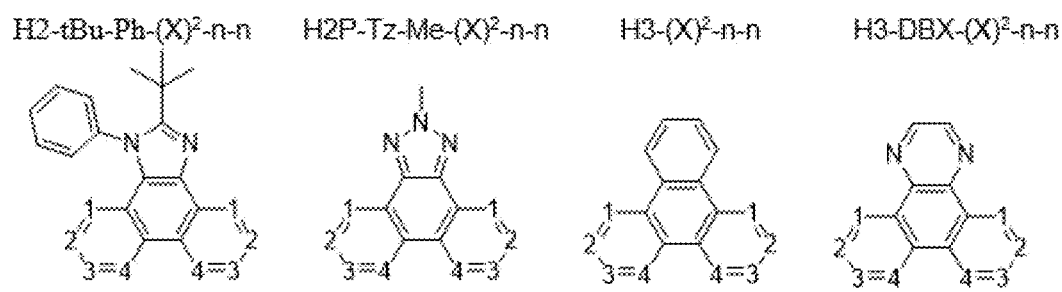
FIG. 6 shows structures of H2P/H3 materials according to embodiments disclosed herein.

It can be seen in Table 2.1b that several of the H2P/H3 materials, which have structures as shown in FIG. 6, have relatively wide $\Delta S_1/T_1$ gaps. While the $T_1$ energies seem to be higher (>2.8 eV in most cases) than what is desired (2.4-2.6 eV), several of these materials exhibit a red-shift of about 0.3 eV on average which would make them viable candidates.

TABLE 2.1b

DFT-calculated properties for H2P/H3 class structures with symmetric Aza substitution patterns.

| | S1 (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| H2P-Im-tBu-Ph | 3.82 | 325 | 2.85 | 435 | −5.22 | −0.75 | 0.97 |
| H2P-Im-tBu-Ph-(N)2-1-1 | 3.73 | 333 | 2.90 | 427 | −5.68 | −1.26 | 0.82 |
| H2P-Im-tBu-Ph-(N)2-2-2 | 3.55 | 349 | 2.88 | 431 | −5.65 | −1.52 | 0.68 |
| H2P-Im-tBu-Ph-(N)2-3-3 | 4.02 | 309 | 2.91 | 426 | −5.94 | −1.30 | 1.11 |
| H2P-Im-tBu-Ph-(N)2-4-4 | 3.79 | 327 | 2.92 | 425 | −5.59 | −1.14 | 0.87 |
| H2P-Tz-Me | 4.15 | 299 | 2.99 | 414 | −5.90 | −1.09 | 1.15 |
| H2P-Tz-Me-(N)2-1-1 | 4.15 | 299 | 2.99 | 414 | −5.90 | −1.09 | 1.15 |
| H2P-Tz-Me-(N)2-2-2 | 4.15 | 299 | 2.99 | 414 | −5.90 | −1.09 | 1.15 |
| H2P-Tz-meth-(N)2-3-3 | 4.15 | 299 | 2.99 | 414 | −5.90 | −1.09 | 1.15 |
| H2P-Tz-meth-(N)2-4-4 | 4.15 | 299 | 2.99 | 414 | −5.90 | −1.09 | 1.15 |
| H3 | 4.01 | 309 | 2.86 | 434 | −5.86 | −0.95 | 1.15 |
| H3-(N)2-1-1 | 4.00 | 310 | 2.93 | 424 | −6.08 | −1.40 | 1.08 |
| H3-(N)2-2-2 | 3.92 | 316 | 2.91 | 426 | −6.32 | −1.77 | 1.01 |
| H3-(N)2-3-3 | 4.03 | 307 | 2.92 | 425 | −6.39 | −1.65 | 1.11 |
| H3-(N)2-4-4 | 3.97 | 312 | 2.94 | 422 | −6.21 | −1.33 | 1.04 |
| H3-DBX | 3.74 | 331 | 2.88 | 431 | −6.15 | −1.73 | 0.86 |
| H3-DBX-(N)2-1-1 | 3.54 | 350 | 2.90 | 427 | −6.55 | −1.83 | 0.64 |
| H3-DBX-(N)2-2-2 | 3.51 | 354 | 2.97 | 418 | −6.64 | −2.23 | 0.54 |
| H3-DBX-(N)2-3-3 | 3.70 | 335 | 2.94 | 421 | −6.65 | −2.30 | 0.76 |
| H3-DBX-(N)2-4-4 | 3.76 | 330 | 2.98 | 416 | −6.65 | −2.01 | 0.79 |

Figure 7:
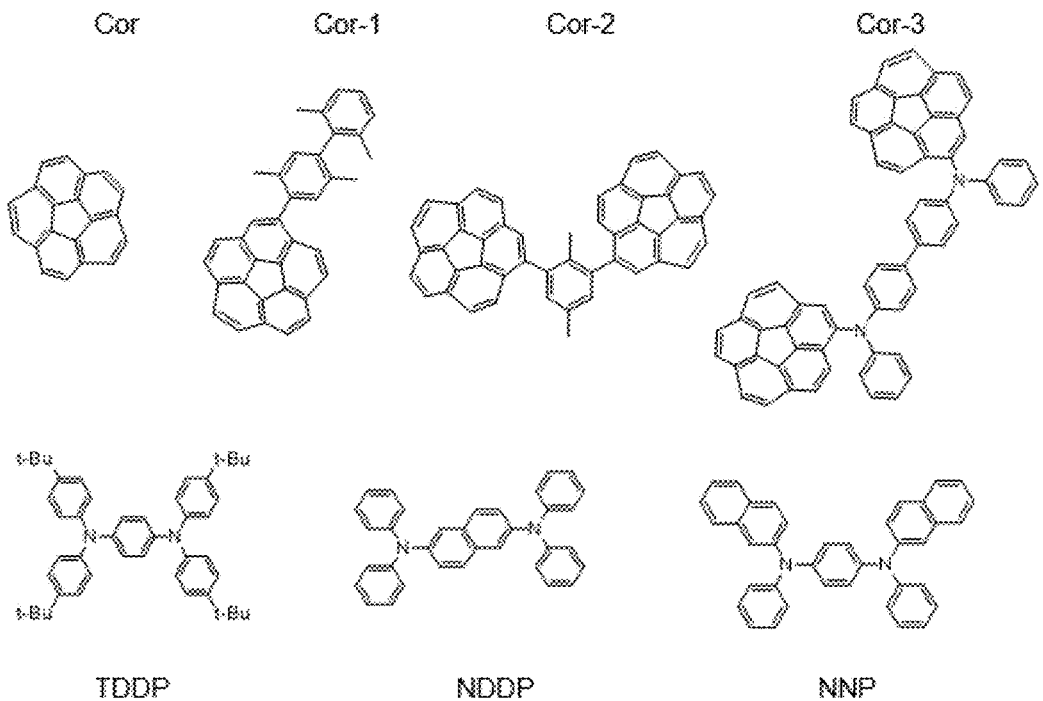
FIG. 7 shows structures of triarylamine-based materials according to embodiments disclosed herein.

Other classes of material considered herein include corannulene and triaryl amine based structures. The corannulene core may aid efficient charge transport making them very attractive. Triarylamine based materials have been shown to have good hole transport properties and are also routinely used as host and hole transport materials. It can be seen in Table 2.1c that several of these structures, shown in FIG. 7, do have wide $\Delta S_1/T_1$ gaps and $T_1$ energies in the desired range.

TABLE 2.1c

DFT calculated properties for corannulene based structures and triarylamine structures.

| | $S_1$ (eV) | $S_1$ (nm) | $T_1$ (eV) | $T_1$ (nm) | HOMO (eV) | LUMO (eV) | $\Delta S_1/T_1$ (eV) |
|---|---|---|---|---|---|---|---|
| Cor | 3.54 | 350 | 2.66 | 466 | −5.77 | −1.92 | 0.88 |
| Cor-1 | 3.50 | 354 | 2.62 | 473 | −5.61 | −1.91 | 0.88 |
| Cor-2 | 3.46 | 358 | 2.59 | 479 | −5.67 | −1.91 | 0.87 |
| Cor-3 | 2.75 | 451 | 2.38 | 521 | −4.61 | −1.85 | 0.37 |
| TDDP | 3.49 | 355 | 2.85 | 435 | −4.26 | −0.69 | 0.64 |
| NDDP | 3.10 | 400 | 2.37 | 523 | −4.44 | −1.45 | 0.73 |
| NNP | 3.17 | 391 | 2.49 | 498 | −4.42 | −1.32 | 0.68 |

Synthesis and Study of fl-Dopants with Small $S_1$, $T_1$ Gap

By screening a number of blue fl emitters and estimating their respective $S_1$, $T_1$, HOMO, and LUMO energies the best candidates of emitters suitable for hybrid WOLED may be identified. Using this information, promising candidates acting as blue fl-dopants with high quantum efficiencies and small singlet-triplet energy gap ($\Delta S_1/T_1$<0.4 eV) have been successfully synthesized and characterized. Their photo-physical and electrochemical properties in both solution and solid matrices have been analyzed as disclosed herein. This combined theoretical/experimental approach allows for rapid identification and targeting of potential candidates that matches the criteria of hybrid blue fl emitters.

Figure 8:
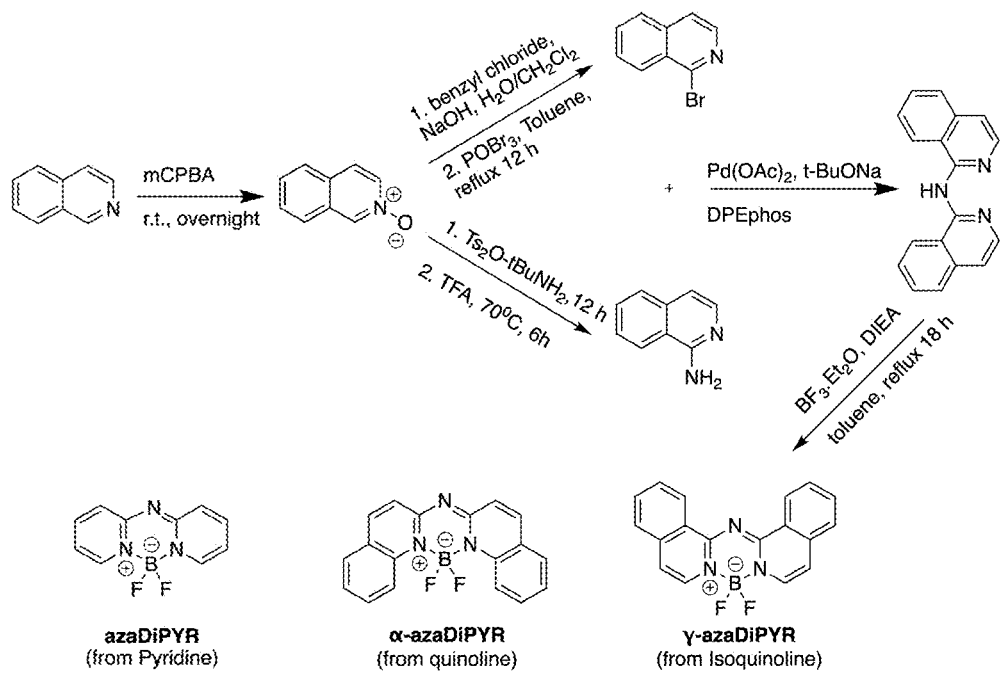
FIG. 8 a procedure to synthesize azaDiPYR derivatives according to embodiments disclosed herein.

In the present work disclosed herein, efforts have focused on synthesizing derivatives of difluoro-boron-azaDiPYR complexes. These complexes were first discovered in the early nineties, but little information is known about their application in OLED devices. Recently, new synthetic procedures of azaDiPYR complexes emerged inspiring a new family of dyes to investigate. FIG. 8 shows the general procedure to successfully synthesize azaDiPYR derivatives in high yields. The target complexes acting as blue fluorescent emitters are azaDiPYR, α-azaDiPYR, and γ-azaDiPYR. These three dyes strongly absorb in the UV-blue part of the spectrum and display blue fluorescence ($\lambda_{em}$=400-470 nm) with high quantum yields in solution and doped in thin films (Φ=42%-86%).

Figure 9A:
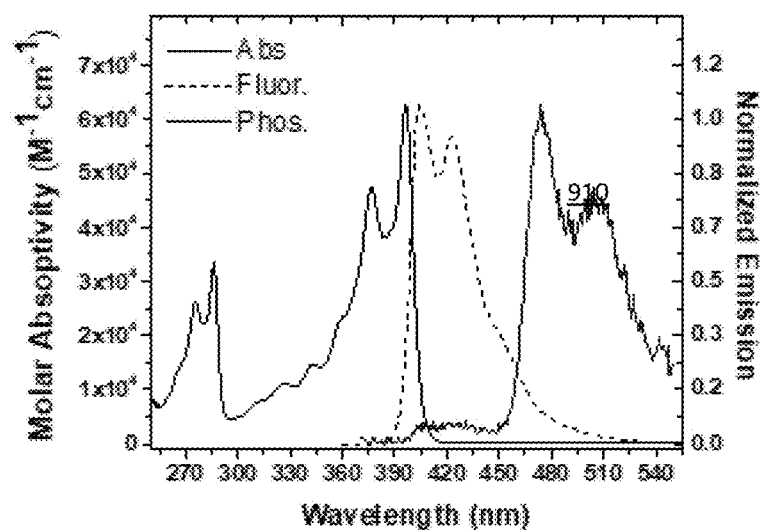
FIGS. 9A and 9B show absorption and emission spectra of azaDiPYR and α-azaDiPYR.
Figure 9B:
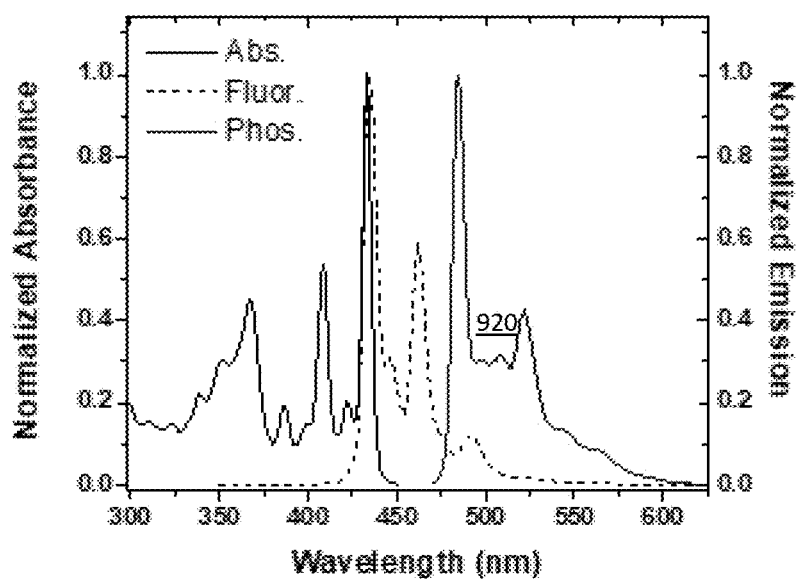

The absorption and emission spectra of azaDiPYR and α-azaDiPYR are shown in FIGS. 9A and 9B. FIG. 9A shows the absorption and normalized emission spectra for azaDiPYR and FIG. 9B shows the same for α-azaDiPYR in MeTHF at room temperature. The gated phosphorescence emission (right-most solid line) was collected at 77 K. Both complexes exhibit strong π to π* absorption bands and intense fluorescence emission in the visible spectrum. The parent azaDiPYR complex has violet-blue fluorescence emission ($\lambda_{em,max}$=405 nm) that is the mirror image of the $S_0$ to $S_1$ transition ($\lambda_{abs, max}$=398 nm). In the UV region, the $S_0$ to $S_2$ transition centered at 270 nm also appears as a vibrational absorption feature. For the α-azaDiPYR, both the absorption and emission profile are red shifted compared to the parent azaDiPYR. This information increases the number of potential candidates of host materials with high HOMO and low LUMO energies that can nest the latter blue emitter complex. The gated phosphorescence emission (shown in solid blue lines 910, 920) taken at low temperatures (77 K) represents the lowest triplet energy ($T_1$).

Table 1.2a compares the singlet and triplet energies for the respective complexes from the calculated methods to the experimental data. The computational data of the singlet-triplet energy gap closely matches the experimental data. The α-azaDiPYR has a small singlet-triplet energy gap of $\Delta S_1/T_1 \leq 0.3$ eV that meets the criteria of developing blue fl-dopants for hybrid WOLED structures and devices, and the parent azaDiPYR has a singlet-triplet energy gap of $\Delta S_1/T_1 \leq 0.5$ eV.

The HOMO and LUMO energies recorded in Table 1.2a were derived from electrochemical data using Ferrocene as an internal standard in acetonitrile solvent.

Figure 10:
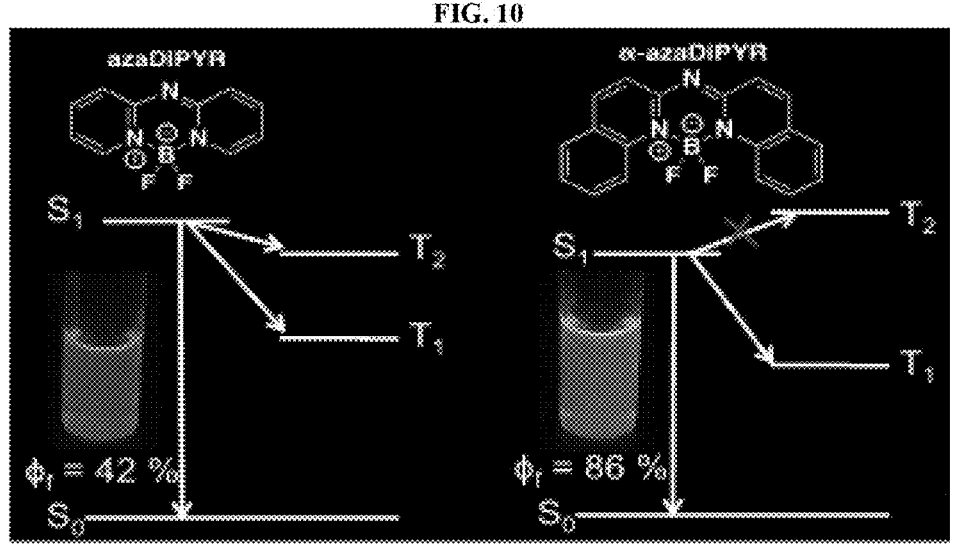
FIG. 10 shows structures and energy level structures for the lowest singlet and triplet states for azaDiPYR and α-azaDiPYR according to embodiments disclosed herein.

From the DFT calculations, it has also been found that the higher quantum yield of α-azaDiPYR ($\Phi_f$=86%) was a result of the relative reordering of the $S_1$ and $T_2$ energies upon benzannulation of the parent structure, which is shown in FIG. 10. The reason the parent azaDiPYR has a lower quantum yield ($\Phi_f$=42%) is because the energy of $T_2$ state is just below the $S_1$ state, enabling fast intersystem crossing that is competitive with fluorescence. All photophysical parameters for azaDiPYR and α-azaDiPYR complexes present in solution and doped in 1 wt % in PMMA films are summarized in Table 1.2b. Notably, the quantum efficiency of α-azaDiPYR remains high in both solution and solid state, maintaining a small singlet-triplet energy gap which is preferable for a blue fluorescent emitter in a hybrid WOLED structure as disclosed herein. FIG. 10 shows a general representation of the lowest singlet and triplet states for azaDiPYR and α-azaDiPYR.

TABLE 1.2a

Theory and experimental data of $S_1$, $T_1$, HOMO, and LUMO energies for azaDiPYR and α-azaDiPYR.

|  | azaDiPYR | | α-azaDiPYR | |
| --- | --- | --- | --- | --- |
|  | eV (calc) | eV (Exp) | eV (calc) | eV (Exp) |
| $S_1$ | 3.16 | 3.11 | 2.78 | 2.86 |
| $T_1$ | 2.65 | 2.64 | 2.39 | 2.56 |
| $\Delta S_1/T_1$ | 0.51 | 0.47 | 0.39 | 0.30 |

TABLE 1.2a-continued

Theory and experimental data of $S_1$, $T_1$, HOMO, and LUMO energies for azaDiPYR and α-azaDiPYR.

|  | azaDiPYR | | α-azaDiPYR | |
| --- | --- | --- | --- | --- |
|  | eV (calc) | eV (Exp) | eV (calc) | eV (Exp) |
| HOMO | −5.34 | −5.88 | −5.62 | −6.67 |
| LUMO | −1.84 | −2.06 | −2.07 | −2.42 |

TABLE 1.2b

Photophysical properties of azaDiPYR and α-azaDiPYR blue fluorescent emitters in solution and solid matrices.

|  |  | MeTHF RT | MeTHF 77K | 1 wt % PMMA at RT |
| --- | --- | --- | --- | --- |
| azaDiPYR | Φ | 0.42 | — | 0.48 |
|  | T (ns) | 2.11 | 2.06 | 2.34 |
|  | $k_r$ (s) | 2 × 10$^8$ | — | 2.05 × 10$^8$ |
|  | $k_{nr}$ (s) | 2.74 × 10$^8$ | — | 2.22 × 10$^8$ |
| α-azaDiPYR | Φ | 0.86 | — | 0.86 |
|  | T (ns) | 3.25 | 2.96 | 3.37 |
|  | $k_r$ (s) | 2.65 × 10$^8$ | — | 2.55 × 10$^8$ |
|  | $k_{nr}$ (s) | 4.31 × 10$^7$ | — | 4.15 × 10$^7$ |

Figure 11:
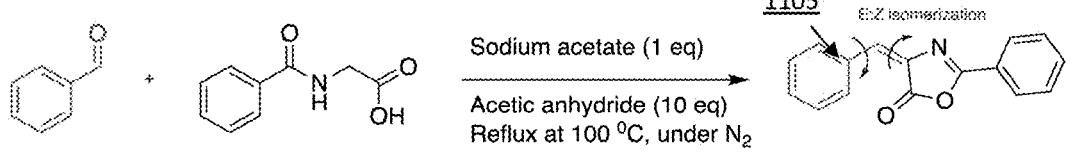
FIG. 11 shows a synthesis of fluorophores according to embodiments disclosed herein.

To further explore other promising candidates of blue fl emitters, the search may be expanded to study compounds with oxazolone core derivatives. The predications from the modeling study disclosed above suggest that the $\Delta S_1/T_1$ gap will be too large for this family of materials. However, those modeling studies allowed the chromophore to relax in its singlet and triplet excited states. The structure change in the triplet excited state was large relative to the ground state, which will not be possible in the solid state. Accordingly, a few of these dyes were prepared to test them experimentally. These compounds are related to the Green Fluorescent Protein (GFP), which are interesting bioluminescent organisms that originate from the jellyfish *Aequorea victoria*. Extracting and stabilizing the oxazolone center from the GFP would give an efficient blue fl emitter with attractive photophysical and electrochemical properties. The synthesis of these fluorophores is summarized in FIG. 11. In principle, it is a condensation reaction that can give the desired product in high yields in the presence of an aldehyde and glycine derivatives.

The oxazolone fluorophore is held in a planar conformation in the interior of the GFP, maintaining favorable photophysics and high quantum efficiency of 60%-80%. In solution, these compounds undergo geometrical distortions in the excited states that deviate from the original planar conformation, leading to low fluorescence quantum yield. The PL quantum yields for these dyes were found to be <10% in all cases. Loss of fluorescence energy is mainly due to the free rotation of the aryl-alkene bond resulting in fast non-radiative decay (shown by the arrow 1105 in FIG. 11). The strategy disclosed herein is to introduce bulky groups around the phenyl ring to increase the steric hindrance and slow down or prevent the free rotation of the aryl group. We will also place the fluorophore in thin film matrix such as PMMA solid to stop the free rotation, resulting in a higher fluorescence quantum yield.

Figure 12:
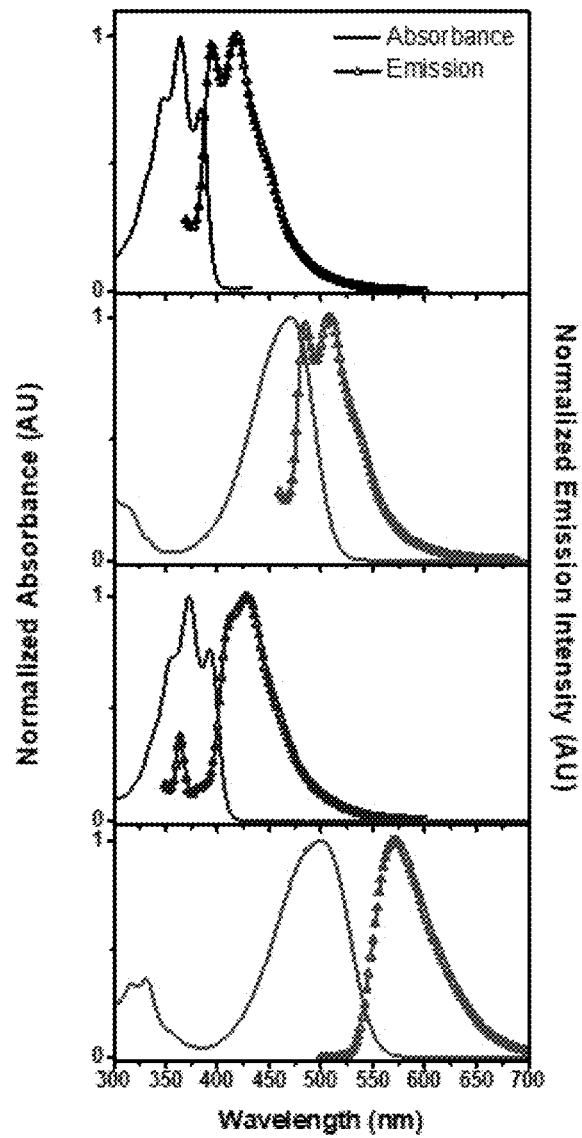
FIG. 12 shows normalized absorption and emission spectra for oxazolone derivatives according to embodiments disclosed herein.

From theoretical modeling, the HOMO is mainly delocalized on the aryl-alkene and the LUMO is on the oxazolone core. In order to lower the singlet-triplet energy gap, we can add functional groups (donating/withdrawing) to minimize the overlap between the HOMO and LUMO, leading to small $\Delta S_1/T_1$. We have synthetically targeted several analogs of oxazolone derivative that would demonstrate this effect, represented in FIG. 12. Compounds with moderately donating groups display an absorption band in the UV region and intense blue fluorescence in the visible spectrum.

We also describe compounds of Formula I.

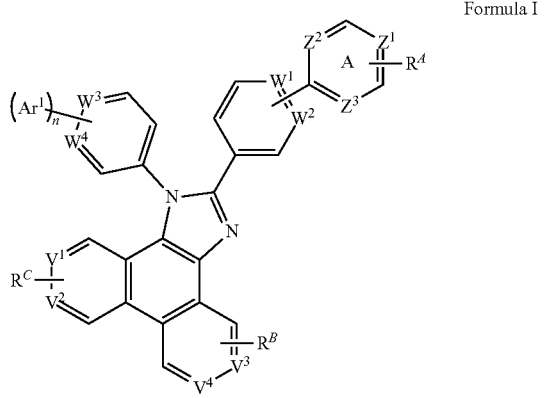

Formula I wherein
- $W^1$ and $W^2$ are independently selected from C, CH, or N; wherein one of $W^1$ or $W^2$ is C that is substituted with Ring A;
- $W^3$ and $W^4$ are independently selected from C, $CR^W$ or N, and n is 0 or 1, wherein if n is 1 then one of $W^3$ or $W^4$ is C that is substituted with $Ar^1$;
- $Z^1$, $Z^2$, and $Z^3$ are independently selected from $CR^A$ or N, and at least one of $Z^1$, $Z^2$, or $Z^3$ is N;
- $V^1$ and $V^2$ are independently selected from $CR^C$ or N;
- $V^3$ and $V^4$ are independently selected from $CR^B$ or N; and
- $Ar^1$ is selected from an optionally substituted aryl, or an optionally substituted heteroaryl;
- $R^W$ is independently selected from the group consisting of hydrogen, deuterium, alkyl, cycloalkyl, alkoxy, aryloxy, amino, silyl, heterocyclic, aryl, heteroaryl, nitrile, isonitrile, and combinations thereof;
- each $R^A$ is independently hydrogen or a substituent selected from the group consisting of deuterium, alkyl, cycloalkyl, alkoxy, aryloxy, amino, silyl, heterocyclic, aryl, heteroaryl, nitrite, isonitrile, and combinations thereof; or optionally, two adjacent $R^A$ join to form a fused aromatic ring, which is optionally substituted;
- $R^B$ and $R^C$ independently represent from mono substitution to the maximum possible number of substitution, or no substitution; and
- each $R^B$ and $R^C$ is independently hydrogen or a substituent selected from the group consisting of deuterium, alkyl, cycloalkyl, alkoxy, aryloxy, amino, silyl, heterocyclic, aryl, heteroaryl, nitrile, isonitrile, and combinations thereof, or optionally, two adjacent $R^B$ or $R^C$ join to form a fused aromatic ring, which is optionally substituted.

In any one select embodiment of the compounds of Formula I, each $R^B$ and $R^C$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

Ring A is selected from pyridine (one of $Z^1$ or $Z^2$ is N, preferably, $Z^1$ is N), or pyrimidine (both $Z^1$ and $Z^2$ are N), or triazine (each of $Z^1$, $Z^2$, and $Z^3$ are N).

In any one of the embodied compounds of Formula I, one of $Z^1$ or $Z^2$ is N, and the other is $CR^A$, which in this case the $R^A$ joins with an adjacent $R^A$ to from a quinazoline ring.

In one embodiment, V is C that is substituted with Ring A, and $W^2$ is CH. In another embodiment, $W^2$ is C that is substituted with Ring A, and $W^1$ is CH.

In any one of the embodied compounds of Formula I, there is particular interest for one $R^A$ to be selected from aryl or heteroaryl, each of which is optionally substituted.

In any one of the embodied compounds of Formula I, n is 1, and $W^3$ is C that is substituted with $Ar^1$. Alternatively, a is 1, and $W^4$ is C that is substituted with $Ar^1$.

In any one of the embodied compounds of Formula I, $Ar^1$ includes a group selected from the group consisting of

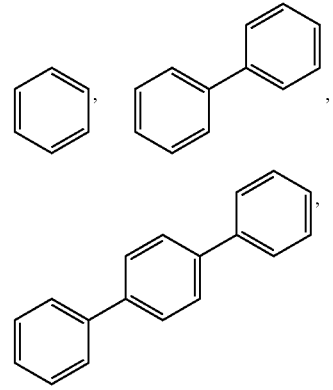

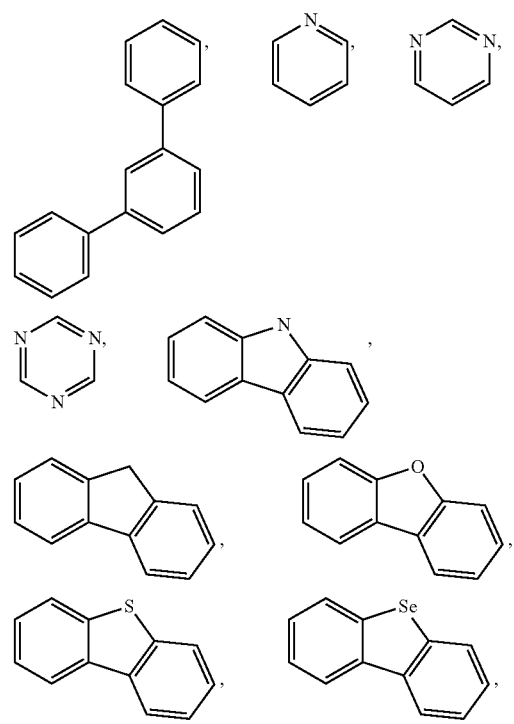

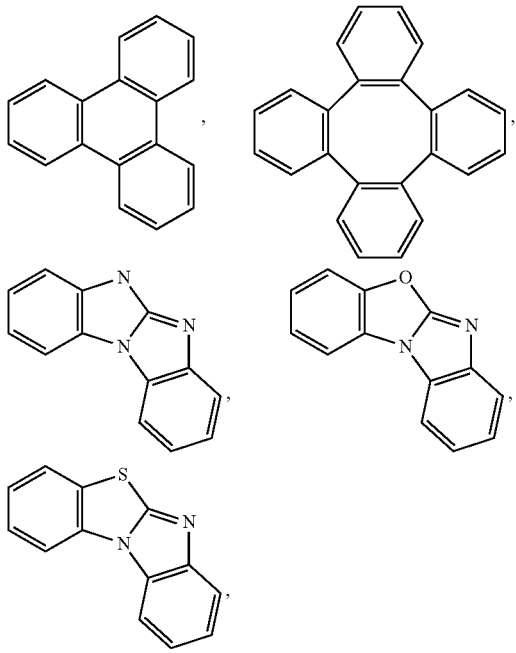

and combinations thereof, or any one aza variant thereof.

In any one of the embodied compounds of Formula I, $Ar^1$ is selected from the group consisting of

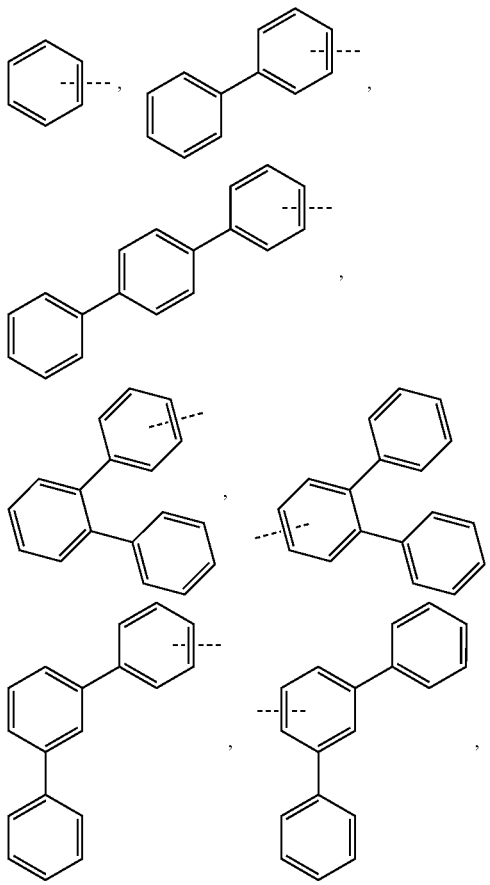

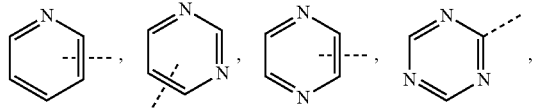

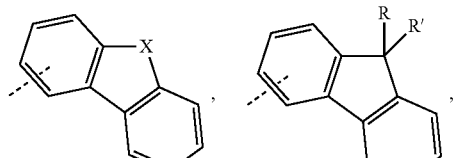

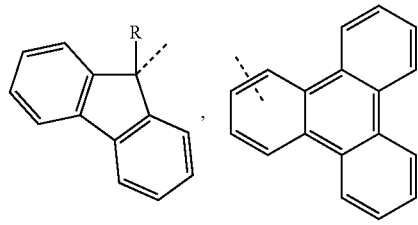

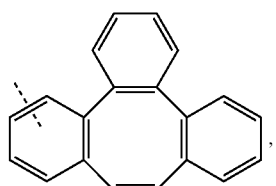

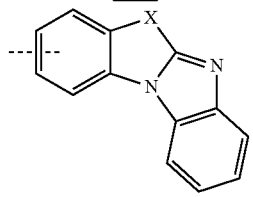 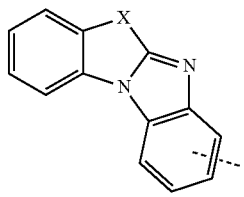

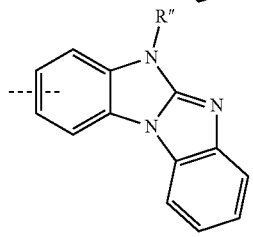 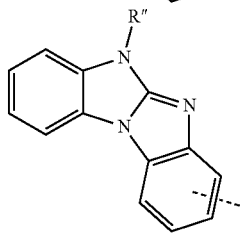

and combinations thereof, or any one aza variant thereof, wherein X is selected from O, S, or Se;

R, R', and R" are independently selected from the group consisting of hydrogen, deuterium, alkyl, cycloalkyl, heteroalkyl, amino, silyl, alkynyl, aryl, heteroaryl, and combinations thereof; and the dotted line represents attachment to $W^3$ or $W^4$.

In any one of the embodied compounds of Formula I, one or two $R^4$ is selected from the group consisting of

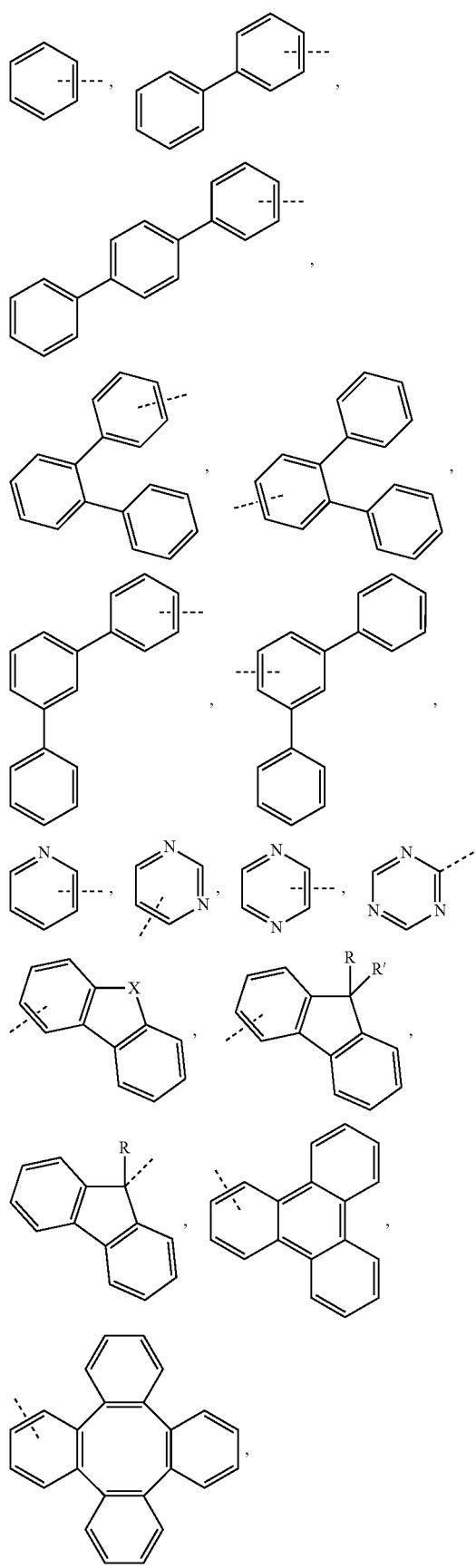

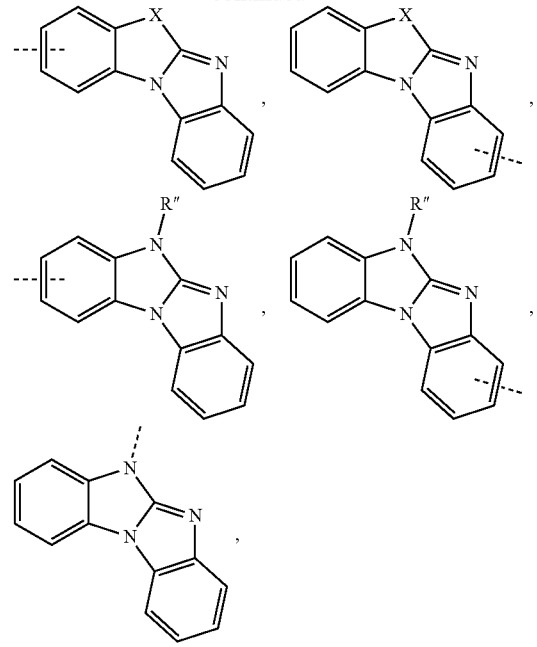

and combinations thereof, or any one aza variant thereof, wherein X is selected from O, S, or Se;

R, R', and R" are independently selected from the group consisting of hydrogen, deuterium, alkyl, cycloalkyl, heteroalkyl, amino, silyl, alkynyl, aryl, heteroaryl, and combinations thereof; and the dotted line represents attachment to Ring A.

Compounds of Formula I of particular interest will have a structural formula selected from the group consisting of

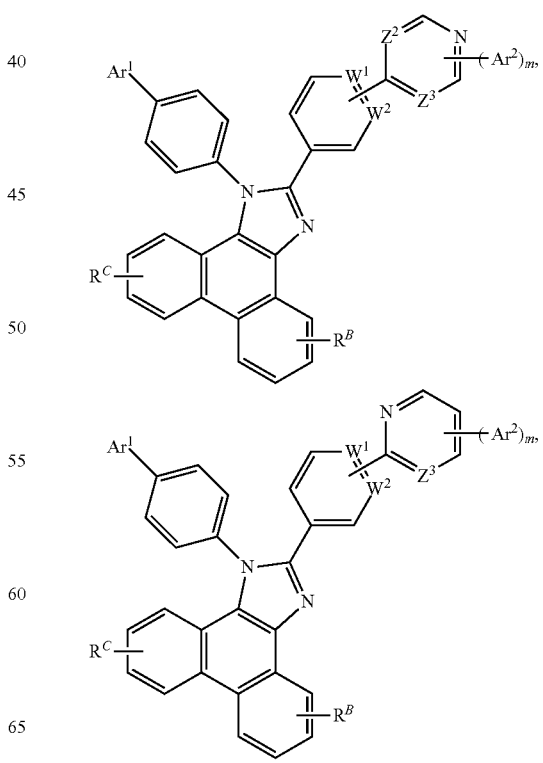

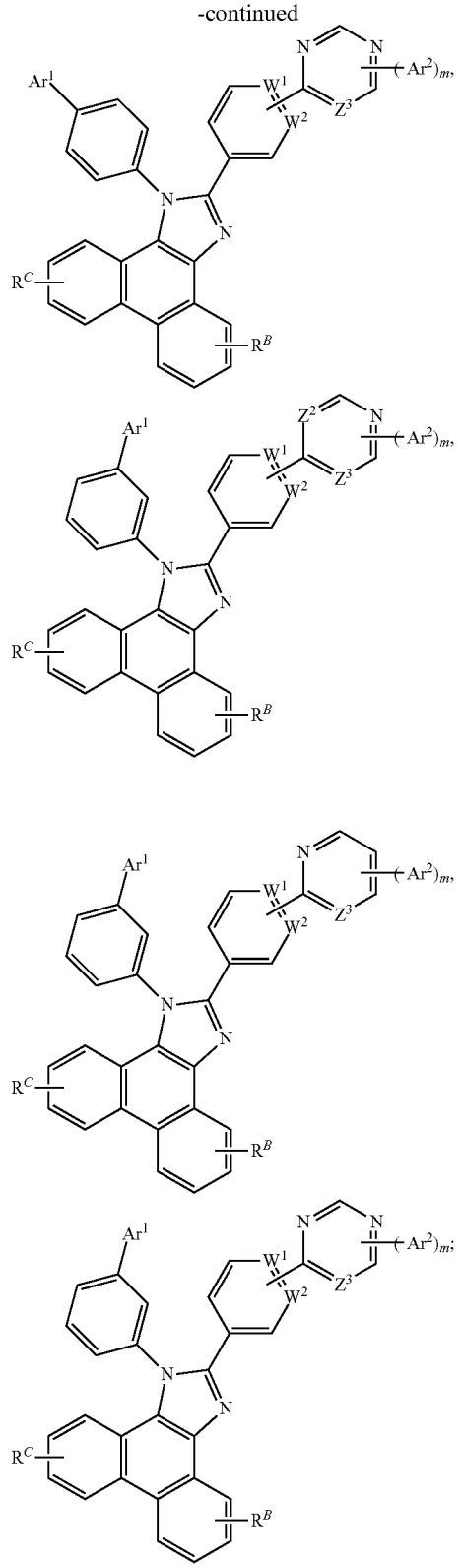
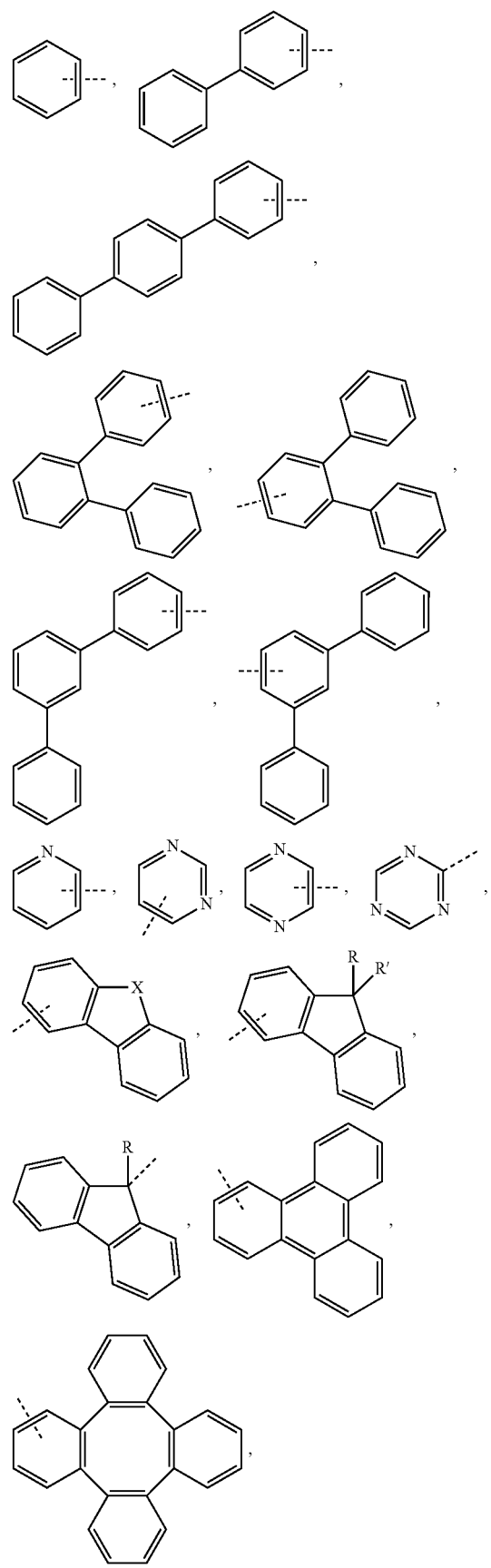
wherein m is 0 or 1, and $Ar^2$ is selected aryl or heteroaryl, each of which is optionally substituted.
In any one of the above structural formula of interest, the aromatic ring system $Ar^2$ is preferably a group selected from the group consisting of -continued

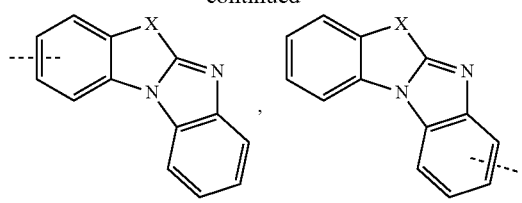

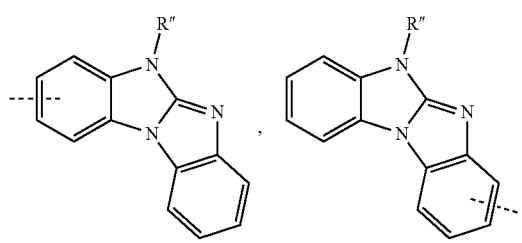

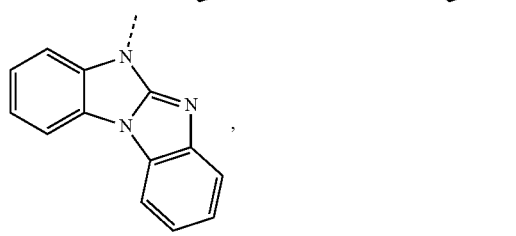

and combinations thereof, or any one aza variant thereof,
wherein X is selected from O, S, or Se;
R, R', and R" are independently selected from the group consisting of hydrogen, deuterium, alkyl, cycloalkyl, heteroalkyl, amino, silyl, alkynyl, aryl, heteroaryl, and combinations thereof; and
the dotted line represents attachment to the Ring A.

The invention is also directed to organic light emitting device (OLED) comprising an anode, a cathode, and an organic layer disposed between the anode and the cathode, the organic layer comprising any one described embodied compound of Formula I.

In one embodiment, the organic layer of the described OLED will be an emissive layer and the compound of Formula I is a host material for a dopant selected from a phosphorescent emissive dopant, a fluorescent emissive dopant, or a TADF emissive dopant.

For example, a phosphorescent emissive dopant of interest is a transition metal complex having at least one ligand or part of the ligand, if the ligand is more than bidentate, selected from the group consisting of

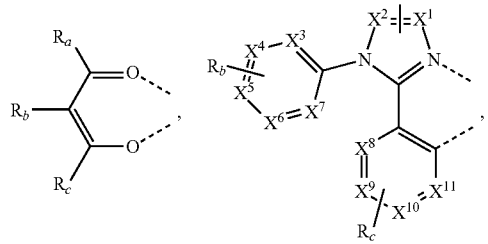

-continued

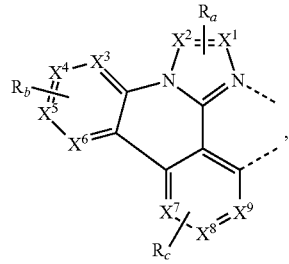

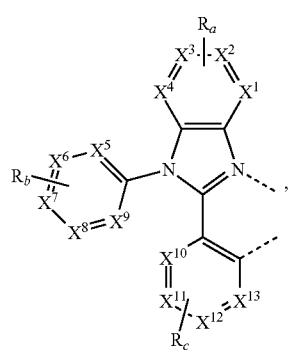

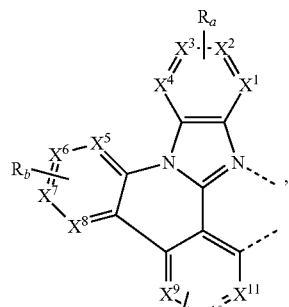

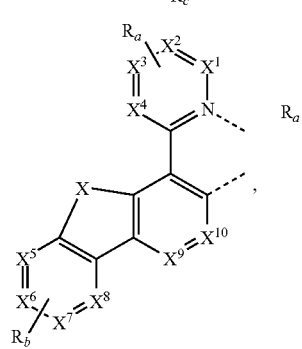

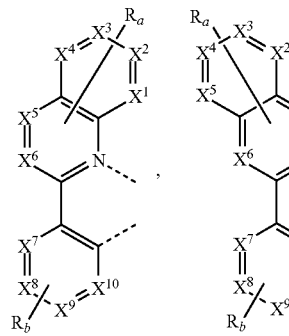

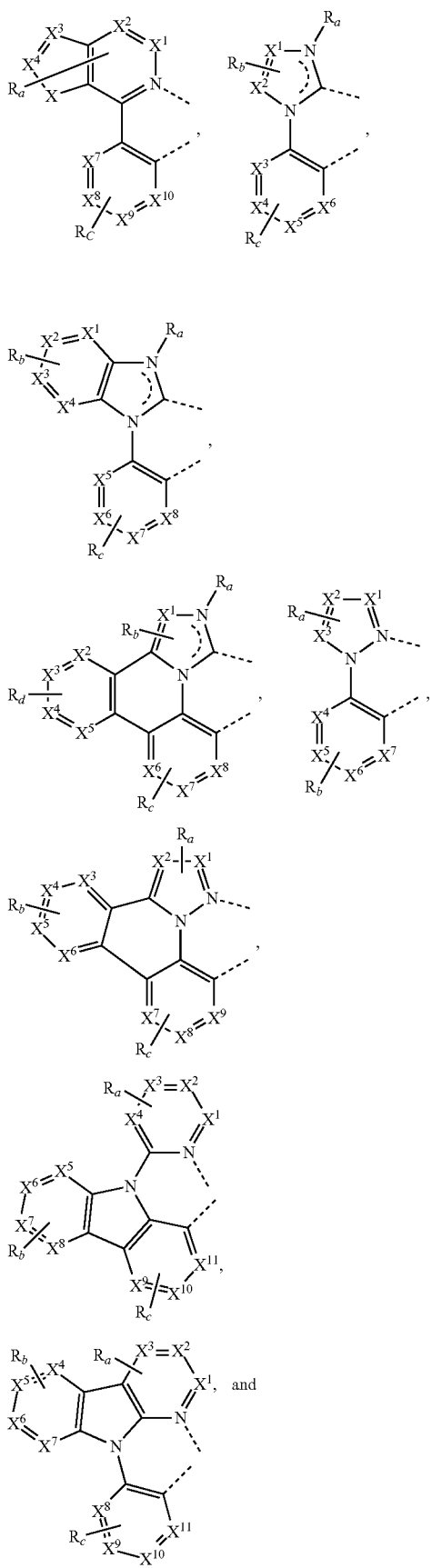

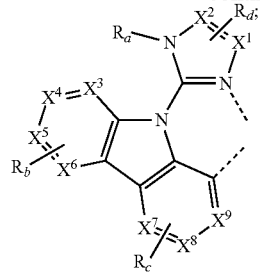

wherein
$X^1$ to $X^{13}$ are independently selected from C or N;
X is selected from the group consisting of BR', NR', PR', O, S, Se, C=O, S=O, $SO_2$, CR'R", SiR'R", and GeR'R"; wherein R' and R" are optionally fused or joined to form a ring;

$R_a$, $R_b$, $R_c$, and $R_d$ may represent from mono substitution to the possible maximum number of substitution, or no substitution;

R' and R", and each $R_a$, $R_b$, $R_c$, and $R_d$ are independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof; or optionally, any two adjacent substituents of $R_a$, $R_b$, $R_c$ and $R_d$ join to form a ring or join to form a multidentate ligand.

Host Materials for fl/ph Hybrid WOLEDs

Potential host materials that can nest the energy levels of blue fluorescent dopant and host the singlet and triplet energy of green, yellow and red phosphorescent emitters have also been identified and analyzed, as well as blue fluorescent emitters with strong blue fluorescence in solid state that can act as host material for green, yellow and red phosphors.

To achieve a high luminous efficacy in a WOLED structure, it typically is desirable for the blue fluorescent emitter to have emission centered around 450 nm (~2.8 eV). Furthermore, the $T_1$ state of the fluorescent emitter generally should be higher than the $T_1$ of the host so the triplets generated on the fluorescent emitter can be transferred to the host matrix which will then be transferred to green, yellow and red phosphors. This limits the $T_1$ state of the blue fluorescent dopant to be around ~2.6 eV and ~2.50 eV for the host material. Using DFT calculations as previously disclosed, promising materials that satisfy these criteria have been selected, synthesized and characterized.

Figure 13:
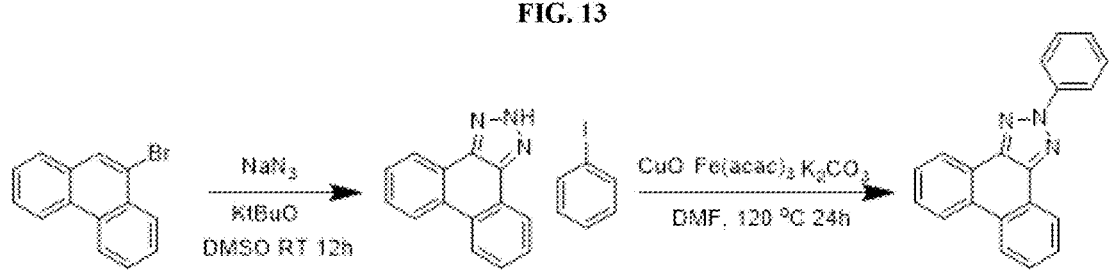
FIG. 13 shows a synthesis of 2-PPT according to embodiments disclosed herein.

As previously indicated, the H2P class of materials show promising properties as host materials. 2-phenyl-2H-phenanthro[9,10-d]triazole (2-PPT) was synthesized and investigated in detail. The preparation of 2-PPT may be carried out in two steps; by benzyne-azide cycloaddition to obtain phenanthro[9,10-d]triazole which is then reacted with iodobenzene via Ullmann coupling to obtain the desired product. The synthesis of 2-PPT is shown in FIG. 13.

Figure 14A:
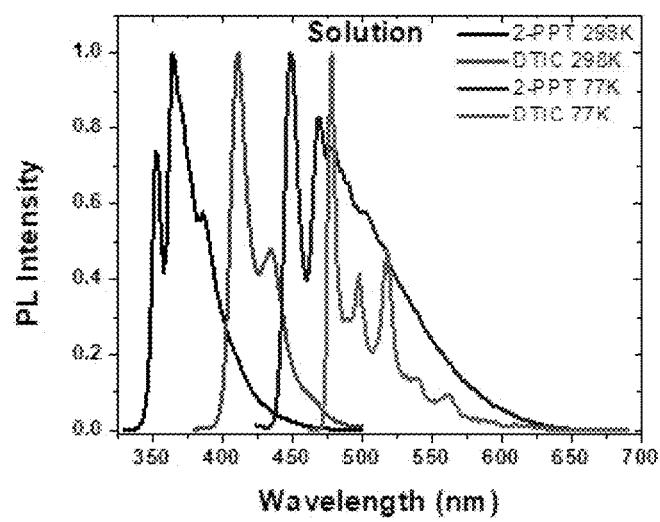
FIGS. 14A and 14B show emission spectra for 2-PPT (298K), DTIC (298K), 2-PPT (77K), and DTIC (77K), respectively, referring to plot peaks left-to-right across the graphs, measured in 2-MeTHF (FIG. 14A) and in the solid state (FIG. 14B) according to embodiments disclosed herein.
Figure 14B:
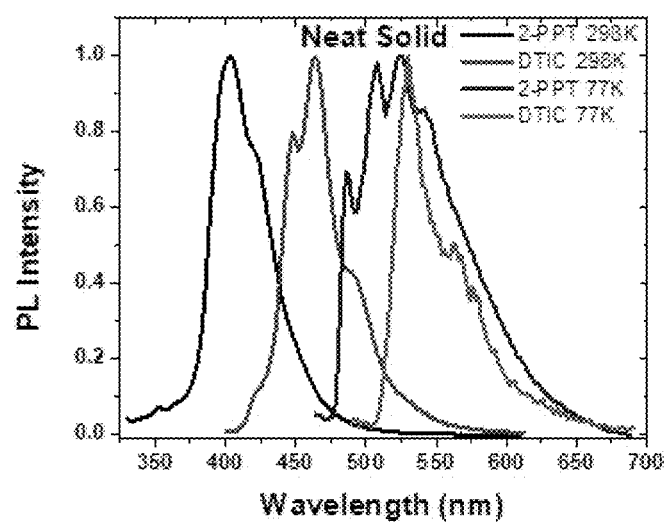

The $S_1$ state of 2-PPT is measured as 3.51 eV which is higher than 2.8 eV of the blue fluorescent dopant satisfying the criterium of high singlet energy. The triplet energy of 2-PPT measured in solution appears to be very high (2.76 eV), but red shifted in solid to 2.59 eV which is low enough for the triplets formed on the blue fluorescent dopant to be transferred to the host and high enough to prevent back energy transfer from the green, yellow and red phosphors to the host, as shown in FIGS. 14A-14B and Table 3a. The LUMO (−1.98 eV) and HOMO (−6.70 eV) levels of 2-PPT are very deep suggesting that it will be electron transporting host. One potential issue with 2-PPT is its low molecular weight which will crystallize on neat film and reduce WOLED lifetime. To mitigate this problem, we dimerize 2-PPT through a meta-bridge phenyl to increase the molecular weight and maintain the photophysical and electrochemical properties.

Another set of potentially-suitable host materials includes indolo carbazoles. From the DFT calculations previously disclosed, H1, H2 and H3 have the right energetics for hosting the emitters in WOLED. One of the indolo-carbazole hosts (H1 with R=phenyl, i.e. DTIC) was synthesized and characterized. The $S_1$ state (3.02 eV) is high enough to host $S_1$ state of the emitters, but the triplet energy in neat solid (2.42 eV) is too low to host green emitter (see FIGS. 14A-B and Table 3a). In addition, the HOMO and LUMO levels are too shallow making charge injection barrier very high. Since the triplet spin density is localized on the bicarbazole backbone of DTIC, the triplet energy cannot be increased by addition of other functional groups. Our alternative to DTIC is to synthesize H2 or H3 analogs since their calculated triplet energy is higher than DTIC.

TABLE 3a

Properties of 2-PPT and DTIC bis 2-PPT

| | $S_1$ (eV) | $T_1$ (eV) THF | $S_1$-$T_1$ (eV) | $T_1$ (eV) Neat Solid | $\Delta T_1$ (eV) | HOMO (eV) | LUMO (eV) |
|---|---|---|---|---|---|---|---|
| 2-PPT | 3.51 | 2.76 | 0.75 | 2.59 | 0.17 | −6.71 | −1.98 |
| DTIC | 3.02 | 2.60 | 0.42 | 2.42 | 0.18 | −4.68 | −1.43 |

Figure 15:
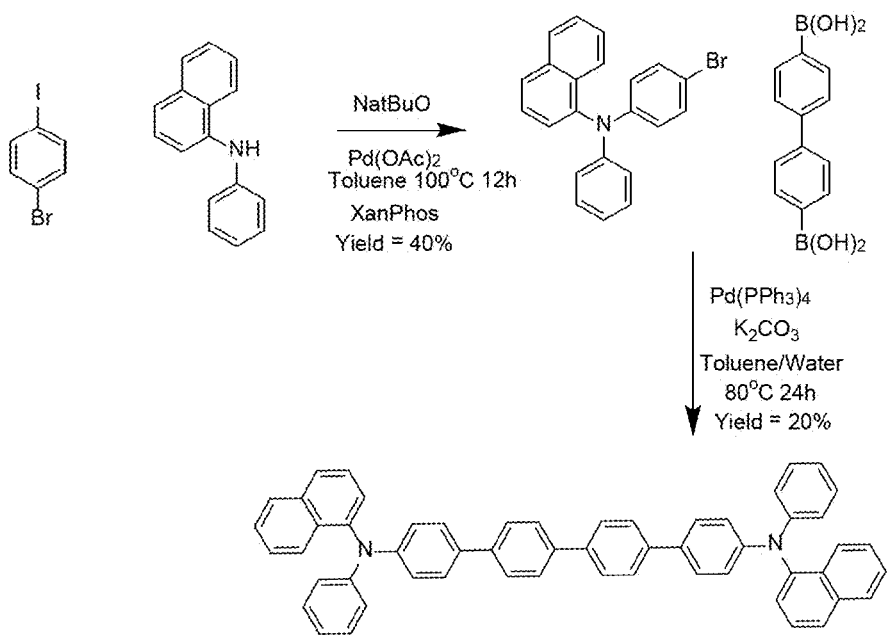
FIG. 15 shows a conventional synthesis for the preparation of 4P-NPD.

A conventional synthesis for the preparation of 4P-NPD is shown in FIG. 15. The challenge with this synthesis is obtaining the N-(4-bromophenyl)-N-phenylnaphthalen-1-amine precursor in large scale in a very pure form, as impurities carried to the next step decomposes the 4P-NPD upon sublimation.

Figure 16:
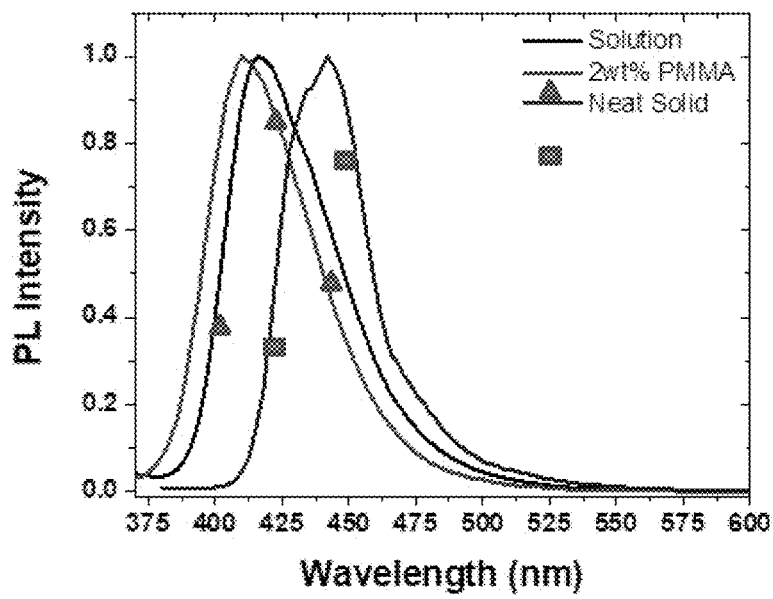
FIG. 16 shows the emission spectra of 4P-NPD according to embodiments disclosed herein.
Figure 17:
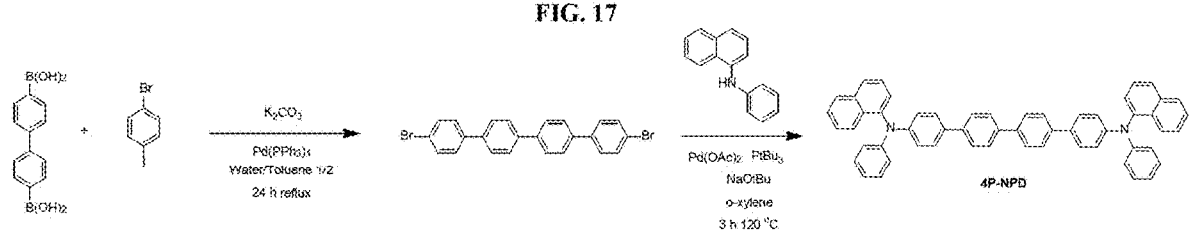
FIG. 17 shows a synthesis of 4P-NPD according to embodiments disclosed herein.

An alternative approach is to make dibroquaterphenyl followed by Ullmann coupling, per the synthesis in FIG. 17. It has been found that dibroquaterphenyl and the byproducts of this reaction were not soluble in common organic solvents, so taking the unpurified precursor yielded 4P-NPD with many byproducts that are hard to separate. Nevertheless, such a process has successfully isolated about 200 mg, sublimed 4P-NPD, and characterize it. The PLQY of 4P-NPD measured previously in the field using comparative method is 92% and this value was confirmed using absolute PLQY measurement as 93%. The emission spectra of 4P-NPD, shown in FIG. 16, is ideal for achieving high luminous efficacy, but the triplet may be too low to host green phosphors in WOLED.

TABLE 3b

| Modelling DTIC analogs | HOMO (eV) | LUMO (eV) | $S_1$ (eV, nm) | f | $T_1$ (eV, nm) | $\Box S_1/T_1$ (eV) |
|---|---|---|---|---|---|---|
| DTIC | −4.85 | −1.03 | 3.28, 378 (3.02, 410)[a] | 0.04 | 2.66, 466 (2.61, 475)[a] | 0.62 (0.41)[a] |

DTIC

TABLE 3b-continued
| Modelling DTIC analogs | | HOMO (eV) | LUMO (eV) | $S_1$ (eV, nm) | f | $T_1$ (eV, nm) | $\Delta S_1/T_1$ (eV) |
|---|---|---|---|---|---|---|---|
| DTIC-TAZ | 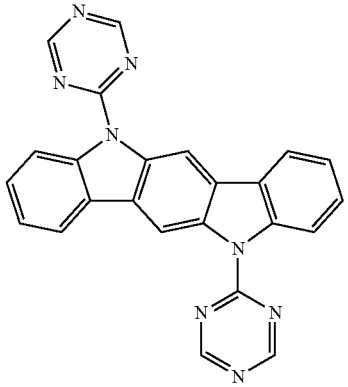<br>DTIC-TAZ | −5.69 | −1.62 | 3.54, 350 | 0.14 | 2.73, 455 | 0.81 |
| DTIC-PhTAZ | | −5.13 | −2.09 | 2.63, 471 | 0.44 | 2.41, 514 | 0.22 |
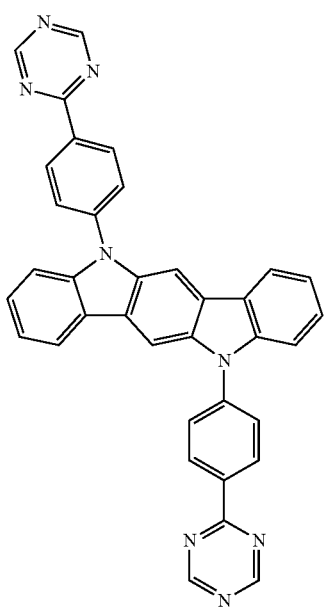
DTIC-PhTAZ TABLE 3b-continued

| Modelling DTIC analogs | HOMO (eV) | LUMO (eV) | S₁ (eV, nm) | f | T₁ (eV, nm) | ΔS₁/T₁ (eV) |
|---|---|---|---|---|---|---|
| DTIC-Phpyrim 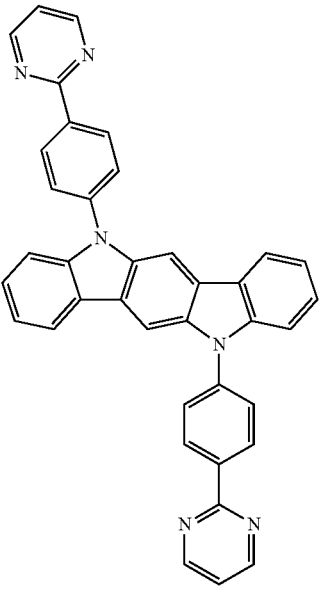 | −4.85 | −1.56 | 2.88, 431 | 0.47 | 2.60, 476 | 0.28 |
| DTIC-coumarin 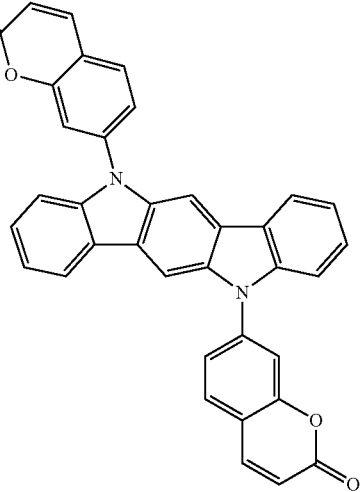 | −5.27 | −2.09 | 2.77, 448 | 0.38 | 2.44, 509 | 0.33 |

Table 3b shows materials that have been modelled and that serve as potential neat blue emitter materials. These compounds have higher oscillator strength than DTIC, which suggests they may have higher PLQY. In addition, the frontiers orbitals are stabilized so charge injection barrier will be lowered. It has been found that DTIC-Phpyrim especially has the right $S_1$ and $T_1$ state and may provide a suitable neat blue fluorescent emitter candidate for WOLED applications.

Host Materials for fl/ph Hybrid WOLEDs

The fl/ph hybrid WOLEDs developed by Y. Sun, et. al in 2006 as previously described involved doping the blue fluorescent dopant at the EML edges and phosphors in the center of the EML. It has been found that the presence or absence of the phosphor did not affect blue emission, indicating that singlets are formed (and trapped) at the EML edges, and triplets subsequently diffused to the center giving green and red emission.

Figure 18:
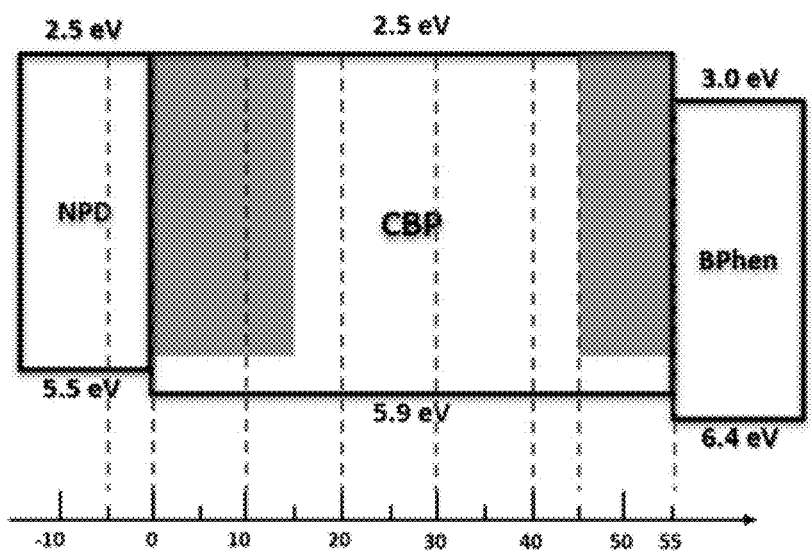
FIG. 18 shows the results of exciton sensor experiments with DCM2 for singlets and PQIr for triplets according to embodiments disclosed herein.

In the present work disclosed herein, experimental techniques have been applied to directly map out the exciton distribution of the EML in this type of device. The relative excitors densities at each position are obtained by inserting thin δ-doped sensors (~1 Å) in the EML and quantifying sensor emission. This method minimizes intervention of the sensor. DCM2 and PQIr were used as sensors in this experiment, for mapping singlets and triplets, respectively. FIG. 18 shows the results of exciton sensor experiments with DCM2 for singlets and PQIr for triplets. The dashed lines indicate sensor positions and the shaded regions indicate blue-doped regions.

The singlet profile shown in FIG. 18 clearly shows that excitons are formed at the EML/ETL interface at low current, and are additionally formed at the HTL/EML interface at higher currents. This successfully represents the prediction made by Y. Sun, et al in 2006. Triplets, on the other hand, have higher densities in the EML center. This is evident of triplet diffusion, where they are formed simultaneously with singlets and diffuse to the center.

Figure 19A:
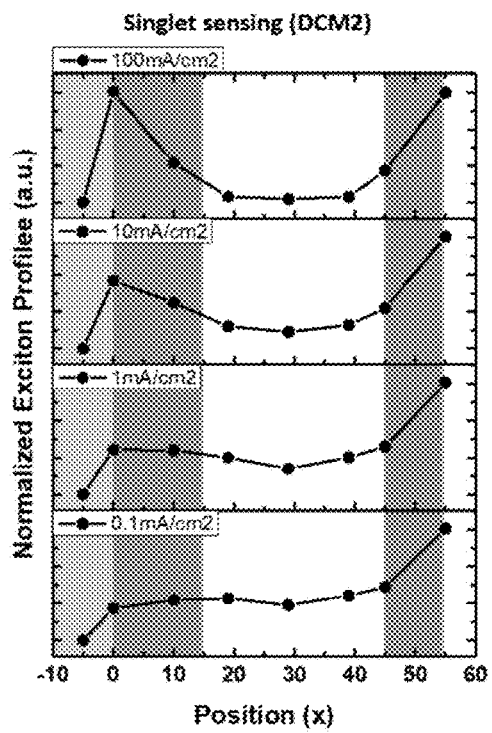
FIGS. 19A, 19B, and 19C show data from exciton sensing experiments according to embodiments disclosed herein.
Figure 19B:
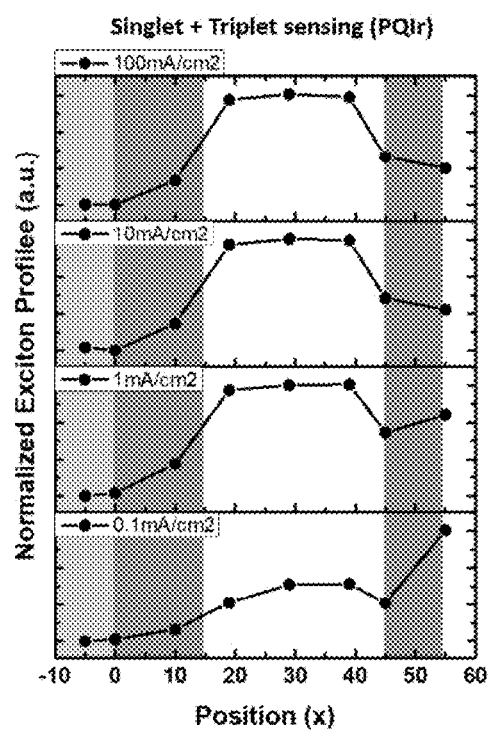
Figure 19C:
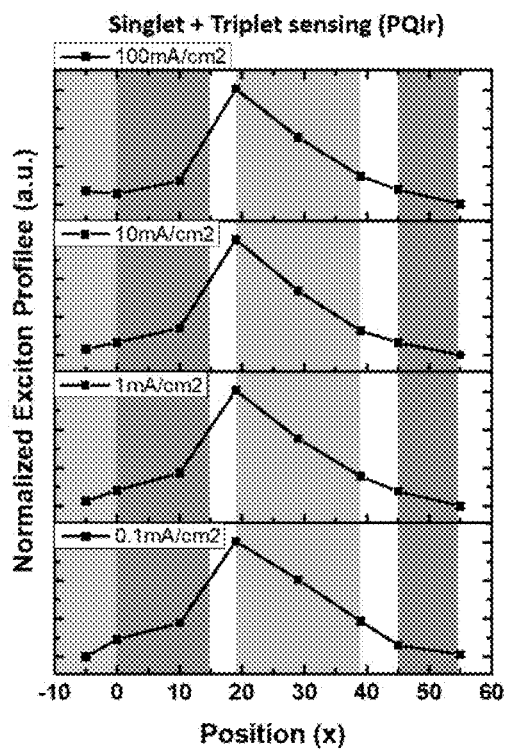

One problem that was found with the prior structure was that phosphors may act as trap site for holes. Y. Sun, et. al previously quantified that 20% of total excitons were formed by direct trapping in phosphors by fitting relative spectra of different dopants to the WOLED spectrum. The analysis disclosed herein reveals that hole trapping effect of phosphors are more significant, indicating that the phosphor doping concentration must be carefully controlled. We have repeated the same sensing experiment with 2 vol % Ir(ppy)$_3$ placed in the EML center. FIGS. 19A-19C show the exciton populations from the sensing experiments. FIGS. 19A and 19B have no phosphor doping (fl-dopant regions shown in center and right-most shaded regions) and FIG. 19C shows the result of adding a 2% Ir(ppy)$_3$ dopant to the center of the EML (shown in the third shaded region from the left at x-position of approximately 20-40). The green shaded region indicates Ir(ppy)$_3$ doping. Unlike the the case with no phosphor, exciton density is highest at the edge of the doped region at all current densities. This shows that holes are trapped by the phosphor and then form excitons when electrons reach the phosphor region edge. This data strongly indicates that a fl/ph hybrid WOLED can be created using this structure.

Figure 20A:
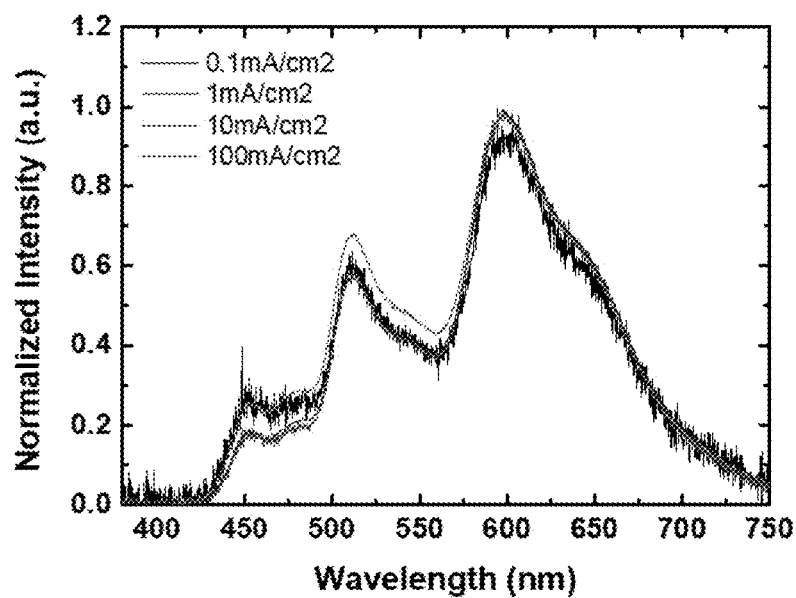
FIG. 20A shows emission spectra for a device according to embodiments disclosed herein.
Figure 20B:
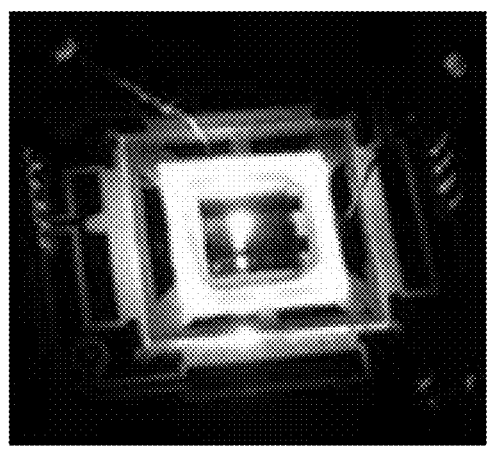
FIG. 20B shows a photograph of the device.
Figure 20C:
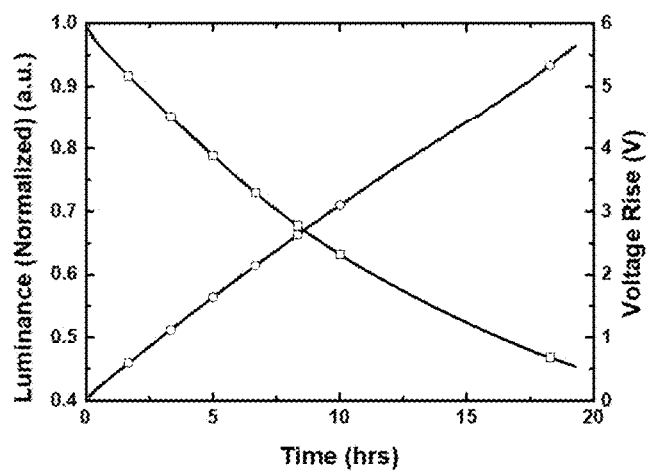
FIG. 20C shows lifetime data for the device.

Using this experimental data, the structure of the WOLED was modified for optimized white emission (CIE=[0.44, 0.42], CRI 88.5, CCT 3150K) and the lifetime was measured. The emission spectra at various current densities are shown in FIG. 20A and the lifetime results are shown in FIG. 20C. FIG. 20B shows a photograph of the experimental device. The device showed relatively poor lifetime at initial luminance of 3000 nits at 10 mA/cm2. This may be explained by poor purity of materials used, unstable ETL (BPhen), or blue dopant fragmentation.

Figure 21:
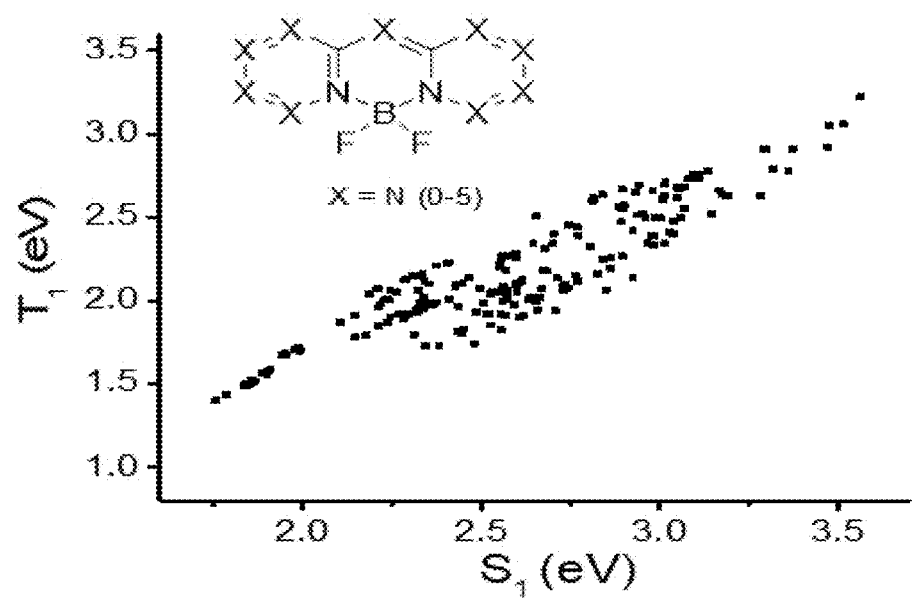
FIG. 21 shows a distribution of design parameters for a DIPYR library according to embodiments disclosed herein.
Figure 22:
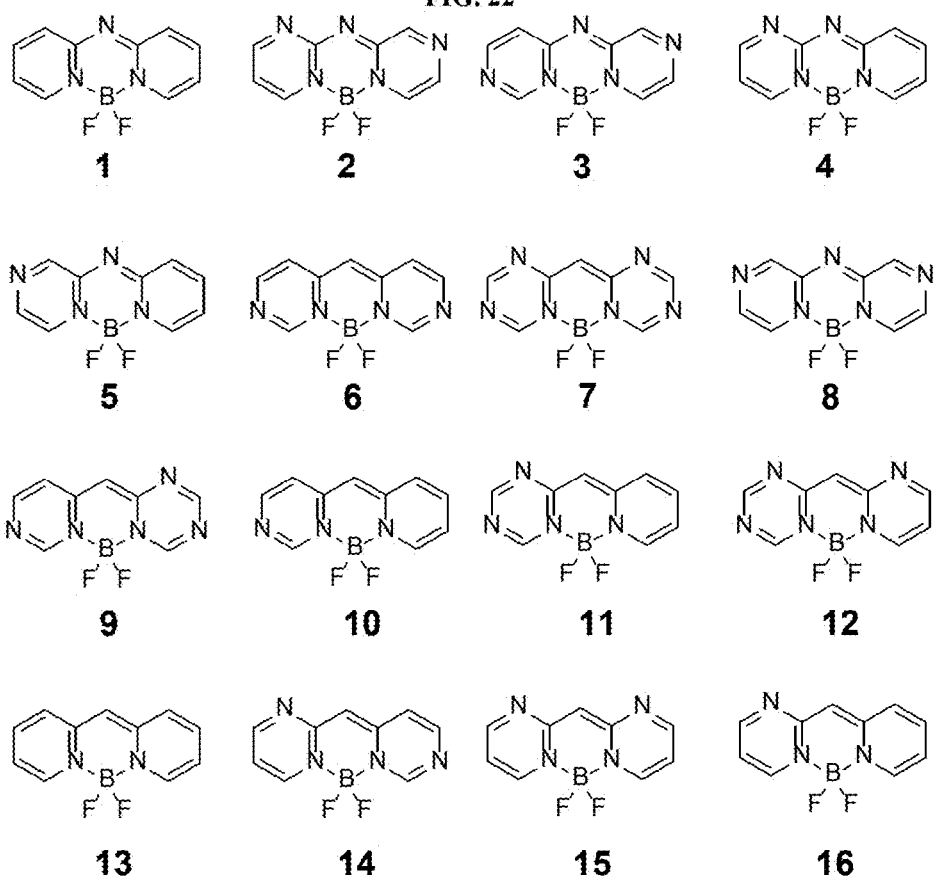
FIG. 22 shows structures for compounds meeting various design criteria according to embodiments disclosed herein.

Further Modelling of Blue Fluorescent Dopants and Host Materials for Hybrid WOLED The effect of aza-substitutions on the DIPYR and α-DIPYR core structures have been further analyzed by means of additional DFT calculations. The calculations were performed at the B3LYP/6-31G level using the Materials Science Suite developed by Schrödinger, LLC. A library containing all possible aza-substitution patterns up to 5 nitrogen substitutions on the positions marked X in FIG. 21 on the DIPYR core structure was developed and DFT calculations (B3LYP/6-31G) were performed on the entire library to assess their candidacy as fluorophores for the hybrid WOLED architecture. The results of the DFT calculations are summarized in FIG. 21. Based on the DFT results, several candidates that satisfy the primary design criteria previously described (i.e. 3.10>$S_1$>2.65 eV and $T_1$>2.18 eV) have been identified. For the screening process, a more relaxed criteria (3.20>$S_1$>2.50 eV and $T_1$>2.10 eV) was employed as insurance against errors associated with the calculations. All candidates that satisfied the relaxed criteria are reported in Table 4, with the corresponding structures shown in FIG. 22. Structures that have N atoms adjacent to other N atoms were screened out as such compounds are synthetically infeasible. In all cases, the $T_2$ state was found to be lower in energy than the $S_1$ state which has been shown to lead to reduction in the photoluminescence quantum yield (PLQY). The DFT calculated $S_1$ energies have been subtracted by 0.44 eV to account for the overestimation due to multi-reference character of the singlet excited states.

TABLE 4

Computed parameters of DIPYR candidates that satisfy the design criteria. All energies are reported in eV.

| | HOMO | LUMO | $S_1$ | $T_1$ | $T_2$ | Osc. ($S_1$) | $\Delta S_1/T_1$ | $\Delta S_1/T_2$ | N-count |
|---|---|---|---|---|---|---|---|---|---|
| 1 | −5.55 | −1.55 | 3.17 | 2.66 | 2.83 | 0.299 | 0.50 | 0.33 | 1 |
| 2 | −6.23 | −2.26 | 3.15 | 2.52 | 2.89 | 0.212 | 0.63 | 0.26 | 3 |
| 3 | −6.36 | −2.41 | 3.14 | 2.52 | 3.01 | 0.257 | 0.62 | 0.13 | 3 |
| 4 | −5.90 | −1.78 | 3.14 | 2.78 | 2.88 | 0.080 | 0.36 | 0.26 | 2 |
| 5 | −5.87 | −2.04 | 3.03 | 2.41 | 2.83 | 0.241 | 0.62 | 0.20 | 2 |
| 6 | −5.80 | −2.07 | 3.01 | 2.34 | 2.84 | 0.307 | 0.67 | 0.18 | 2 |
| 7 | −6.46 | −2.53 | 2.99 | 2.49 | 2.91 | 0.011 | 0.49 | 0.07 | 4 |
| 8 | −6.21 | −2.47 | 2.98 | 2.34 | 2.65 | 0.274 | 0.65 | 0.33 | 3 |
| 9 | −6.12 | −2.29 | 2.92 | 2.42 | 2.85 | 0.045 | 0.51 | 0.07 | 3 |
| 10 | −5.33 | −1.73 | 2.84 | 2.24 | 2.64 | 0.214 | 0.60 | 0.20 | 1 |
| 11 | −5.65 | −1.94 | 2.81 | 2.33 | 2.68 | 0.024 | 0.48 | 0.13 | 2 |
| 12 | −5.96 | −2.18 | 2.77 | 2.39 | 2.67 | 0.032 | 0.38 | 0.10 | 3 |
| 13 | −4.87 | −1.40 | 2.71 | 2.14 | 2.43 | 0.235 | 0.58 | 0.28 | 0 |
| 14 | −5.62 | −1.96 | 2.68 | 2.31 | 2.59 | 0.045 | 0.37 | 0.09 | 2 |
| 15 | −5.46 | −1.82 | 2.60 | 2.28 | 2.44 | 0.016 | 0.32 | 0.16 | 2 |
| 16 | −5.16 | −1.61 | 2.55 | 2.21 | 2.41 | 0.033 | 0.34 | 0.14 | 1 |

Figure 23:
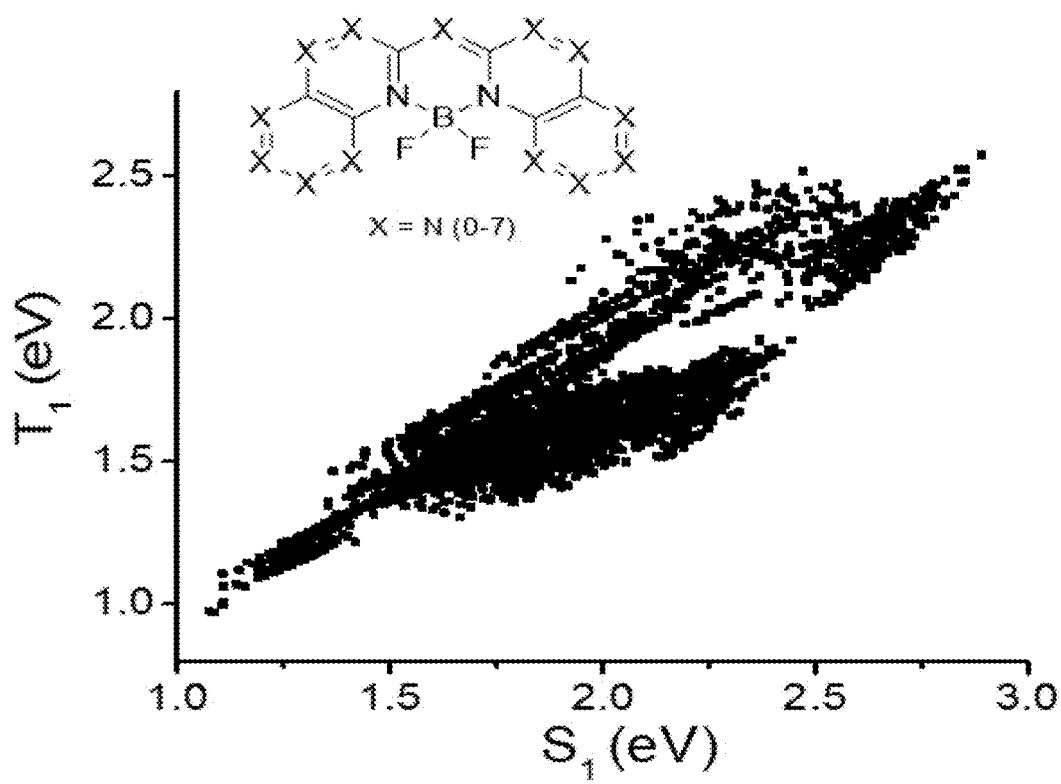
FIG. 23 shows a distribution of design parameters for a α-DIPYR library according to embodiments disclosed herein.

For the α-DIPYR core structure, the library was limited to all possible aza-substitution patterns up to a maximum of 7 nitrogen transmutations in the positions marked 'X' in FIG. 23. The most promising candidates that satisfy the relaxed design criteria (3.20>$S_1$>2.50 eV and $T_1$=2.10 eV) are listed in Table 5. Again, structures that have N atoms adjacent to other N atoms were screened out. In all cases, the $T_2$ state is above the $S_1$ and are hence likely to not suffer from the issue of fluorescence quenching by nonradiative ISC events to which the DIPYR structures are prone. Again, a correction factor of −0.44 eV was applied to the DFT calculated $S_1$ energies to off-set the errors due to multi-reference nature of the singlet excited states in these systems.

TABLE 5

Figure 24:
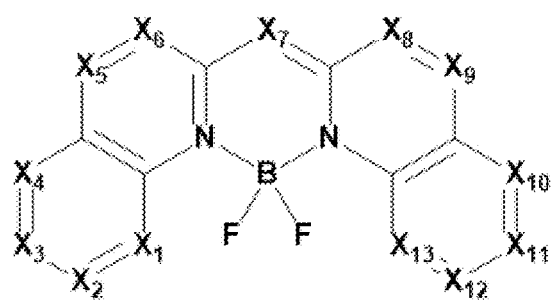
FIG. 24 shows a structure of α-DIPYR candidates according to embodiments disclosed herein.

Computed parameters of α-DIPYR candidates that satisfy the design criteria. ('N' substitution positions follow the numbering scheme above), with the general structure shown in FIG. 24. All energies are reported in eV.

| | N-Positions | HOMO | LUMO | $S_1$ | $T_1$ | $T_2$ | Osc. ($S_1$) | $\Delta S_1/T_1$ | $\Delta S_1/T_2$ | N-count |
|---|---|---|---|---|---|---|---|---|---|---|
| 1 | 7-8-11-6-3 | −6.73 | −2.97 | 2.89 | 2.57 | 3.09 | 0.380 | 0.32 | −0.20 | 5 |
| 2 | 7-8-11-6-1-3 | −6.83 | −3.12 | 2.85 | 2.52 | 3.13 | 0.386 | 0.33 | −0.28 | 6 |
| 3 | 7-8-11-13-6-1-3 | −6.92 | −3.24 | 2.84 | 2.52 | 3.10 | 0.431 | 0.31 | −0.26 | 7 |
| 4 | 7-11-6-3 | −6.48 | −2.79 | 2.84 | 2.52 | 2.94 | 0.424 | 0.32 | −0.11 | 4 |
| 5 | 7-8-6-3 | −6.37 | −2.70 | 2.80 | 2.48 | 3.05 | 0.337 | 0.32 | −0.24 | 4 |
| 6 | 7-11-3 | −6.25 | −2.59 | 2.85 | 2.48 | 2.91 | 0.569 | 0.37 | −0.06 | 3 |

TABLE 5-continued

Computed parameters of α-DIPYR candidates that satisfy the design criteria. ('N' substitution positions follow the numbering scheme above), with the general structure shown in FIG. 24. All energies are reported in eV.

|    | N-Positions       | HOMO  | LUMO  | $S_1$ | $T_1$ | $T_2$ | Osc. ($S_1$) | $\Delta S_1/T_1$ | $\Delta S_1/T_2$ | N-count |
|----|-------------------|-------|-------|------|------|------|-------|------|-------|---|
| 7  | 7-11-13-6-3       | −6.56 | −2.90 | 2.85 | 2.47 | 3.06 | 0.473 | 0.37 | −0.22 | 5 |
| 8  | 7-8-13-6-3        | −6.48 | −2.84 | 2.77 | 2.47 | 3.05 | 0.350 | 0.30 | −0.27 | 5 |
| 9  | 7-8-11-6-4        | −6.57 | −2.92 | 2.78 | 2.47 | 3.03 | 0.354 | 0.32 | −0.25 | 5 |
| 10 | 7-11-6-1-3        | −6.57 | −2.97 | 2.76 | 2.45 | 2.91 | 0.400 | 0.31 | −0.15 | 5 |
| 11 | 7-6-3             | −6.14 | −2.53 | 2.76 | 2.45 | 2.91 | 0.378 | 0.31 | −0.15 | 3 |
| 12 | 7-8-13-6-1-3      | −6.55 | −2.95 | 2.76 | 2.45 | 3.00 | 0.391 | 0.31 | −0.24 | 6 |
| 13 | 7-11-6            | −6.13 | −2.52 | 2.76 | 2.44 | 2.94 | 0.369 | 0.32 | −0.17 | 3 |
| 14 | 7-13-6-3          | −6.22 | −2.62 | 2.78 | 2.44 | 2.99 | 0.438 | 0.34 | −0.21 | 4 |
| 15 | 7-10-6-3          | −6.32 | −2.72 | 2.76 | 2.44 | 2.99 | 0.414 | 0.32 | −0.23 | 4 |
| 16 | 7-8-11-13-6-4     | −6.66 | −3.05 | 2.77 | 2.43 | 3.01 | 0.380 | 0.34 | −0.24 | 6 |
| 17 | 7-11-1-3          | −6.34 | −2.72 | 2.83 | 2.43 | 2.93 | 0.579 | 0.40 | −0.10 | 4 |
| 18 | 7-12-6-3          | −6.38 | −2.76 | 2.77 | 2.43 | 2.97 | 0.349 | 0.34 | −0.20 | 4 |
| 19 | 7-3               | −5.92 | −2.33 | 2.79 | 2.43 | 2.90 | 0.516 | 0.36 | −0.11 | 2 |
| 20 | 7-8-6             | −6.04 | −2.44 | 2.73 | 2.43 | 2.98 | 0.307 | 0.31 | −0.24 | 3 |
| 21 | 7-11-13-1-3       | −6.41 | −2.83 | 2.81 | 2.42 | 2.98 | 0.604 | 0.39 | −0.18 | 5 |
| 22 | 7-8-6-1-3         | −6.45 | −2.86 | 2.75 | 2.41 | 3.02 | 0.335 | 0.34 | −0.27 | 5 |
| 23 | 7-8-12-6-3        | −6.60 | −2.98 | 2.75 | 2.41 | 3.00 | 0.249 | 0.33 | −0.26 | 5 |
| 24 | 7-10-12-6-3       | −6.59 | −2.98 | 2.78 | 2.41 | 3.01 | 0.383 | 0.36 | −0.23 | 5 |
| 25 | 7-11-6-4          | −6.32 | −2.76 | 2.71 | 2.41 | 2.91 | 0.360 | 0.30 | −0.20 | 4 |
| 26 | 7-11-6-1          | −6.23 | −2.69 | 2.69 | 2.41 | 2.92 | 0.351 | 0.28 | −0.23 | 4 |
| 27 | 7-13-3            | −6.01 | −2.44 | 2.77 | 2.40 | 2.92 | 0.535 | 0.36 | −0.16 | 3 |
| 28 | 7-11-4            | −6.09 | −2.53 | 2.76 | 2.40 | 2.92 | 0.524 | 0.36 | −0.16 | 3 |
| 29 | 7-11-13-6-1       | −6.30 | −2.76 | 2.72 | 2.40 | 2.94 | 0.409 | 0.32 | −0.22 | 5 |
| 30 | 7-8-6-4           | −6.23 | −2.67 | 2.70 | 2.40 | 2.95 | 0.315 | 0.30 | −0.25 | 4 |
| 31 | 7-13-6-1-3        | −6.30 | −2.77 | 2.70 | 2.40 | 2.96 | 0.413 | 0.31 | −0.26 | 5 |
| 32 | 7-9-11-6-3        | −6.76 | −3.14 | 2.80 | 2.40 | 2.88 | 0.448 | 0.41 | −0.08 | 5 |
| 33 | 7-6               | −5.82 | −2.27 | 2.69 | 2.40 | 2.90 | 0.333 | 0.30 | −0.21 | 2 |
| 34 | 7-8-13-6-1        | −6.21 | −2.67 | 2.69 | 2.39 | 2.90 | 0.355 | 0.29 | −0.22 | 5 |
| 35 | 7-8-11-6-2-4      | −6.83 | −3.24 | 2.70 | 2.39 | 2.78 | 0.000 | 0.30 | −0.08 | 6 |
| 36 | 7-8-11-13-6-2-4   | −6.91 | −3.33 | 2.65 | 2.39 | 2.75 | 0.000 | 0.26 | −0.11 | 7 |
| 37 | 7-12-3            | −6.16 | −2.58 | 2.76 | 2.39 | 2.91 | 0.428 | 0.37 | −0.15 | 3 |
| 38 | 7-11-13-6         | −6.21 | −2.62 | 2.77 | 2.39 | 2.98 | 0.423 | 0.39 | −0.21 | 4 |
| 39 | 7                 | −5.62 | −2.07 | 2.73 | 2.39 | 2.88 | 0.476 | 0.34 | −0.15 | 1 |
| 40 | 7-8-13-6-4        | −6.31 | −2.77 | 2.69 | 2.39 | 2.91 | 0.343 | 0.30 | −0.22 | 5 |
| 41 | 7-8-10-6-4        | −6.41 | −2.87 | 2.69 | 2.38 | 2.91 | 0.338 | 0.31 | −0.22 | 5 |
| 42 | 7-11-13-6-4       | −6.40 | −2.84 | 2.74 | 2.38 | 2.95 | 0.419 | 0.36 | −0.20 | 5 |
| 43 | 7-8-6-1           | −6.12 | −2.58 | 2.68 | 2.38 | 2.94 | 0.308 | 0.30 | −0.26 | 4 |
| 44 | 7-8-11-13-6-1-4   | −6.76 | −3.24 | 2.66 | 2.38 | 2.71 | 0.000 | 0.28 | −0.05 | 7 |
| 45 | 7-10-6            | −5.99 | −2.46 | 2.69 | 2.38 | 2.93 | 0.368 | 0.31 | −0.23 | 3 |
| 46 | 7-8-12-6-1-3      | −6.68 | −3.10 | 2.73 | 2.38 | 2.94 | 0.300 | 0.36 | −0.21 | 6 |
| 47 | 7-13-1-3          | −6.08 | −2.55 | 2.75 | 2.37 | 2.94 | 0.562 | 0.37 | −0.19 | 4 |
| 48 | 7-12-6            | −6.06 | −2.50 | 2.71 | 2.37 | 2.93 | 0.319 | 0.34 | −0.22 | 3 |
| 49 | 7-10-6-1-3        | −6.40 | −2.89 | 2.69 | 2.37 | 2.99 | 0.385 | 0.32 | −0.30 | 5 |
| 50 | 7-13-6            | −5.89 | −2.35 | 2.71 | 2.37 | 2.92 | 0.395 | 0.34 | −0.21 | 3 |
| 51 | 7-9-11-6-1-3      | −6.83 | −3.29 | 2.74 | 2.36 | 2.82 | 0.432 | 0.37 | −0.09 | 6 |
| 52 | 7-12-6-1-3        | −6.46 | −2.93 | 2.70 | 2.36 | 2.99 | 0.332 | 0.34 | −0.30 | 5 |
| 53 | 7-8-11-6-1-4      | −6.68 | −3.17 | 2.67 | 2.36 | 2.76 | 0.323 | 0.31 | −0.09 | 6 |
| 54 | 7-9-11-13-6-3     | −6.86 | −3.24 | 2.65 | 2.36 | 2.82 | 0.000 | 0.29 | −0.17 | 6 |
| 55 | 7-11-2-4          | −6.35 | −2.81 | 2.74 | 2.36 | 2.91 | 0.432 | 0.38 | −0.17 | 4 |
| 56 | 7-6-1-3           | −6.22 | −2.72 | 2.66 | 2.36 | 2.89 | 0.342 | 0.31 | −0.23 | 4 |
| 57 | 7-9-11-13-6-1-3   | −6.93 | −3.37 | 2.53 | 2.36 | 2.73 | 0.000 | 0.17 | −0.20 | 7 |
| 58 | 7-11-6-2          | −6.35 | −2.82 | 2.66 | 2.36 | 2.89 | 0.240 | 0.31 | −0.23 | 4 |
| 59 | 7-11-13-4         | −6.17 | −2.64 | 2.75 | 2.35 | 2.97 | 0.544 | 0.39 | −0.22 | 4 |
| 60 | 7-1-3             | −6.00 | −2.46 | 2.76 | 2.35 | 2.91 | 0.521 | 0.40 | −0.16 | 3 |
| 61 | 7-13-6-1          | −5.97 | −2.49 | 2.64 | 2.35 | 2.88 | 0.367 | 0.29 | −0.24 | 4 |
| 62 | 7-10-13-6-3       | −6.41 | −2.89 | 2.73 | 2.35 | 2.94 | 0.456 | 0.37 | −0.21 | 5 |
| 63 | 7-4               | −5.78 | −2.27 | 2.70 | 2.35 | 2.89 | 0.479 | 0.35 | −0.19 | 2 |
| 64 | 7-8-6-2           | −6.26 | −2.72 | 2.67 | 2.35 | 2.91 | 0.224 | 0.31 | −0.24 | 4 |
| 65 | 7-13-6-4          | −6.07 | −2.57 | 2.67 | 2.35 | 2.88 | 0.380 | 0.32 | −0.21 | 4 |
| 66 | 7-10-13-6-1-3     | −6.50 | −3.01 | 2.69 | 2.35 | 2.86 | 0.453 | 0.34 | −0.17 | 6 |
| 67 | 7-8-12-6-4        | −6.45 | −2.92 | 2.67 | 2.35 | 2.87 | 0.261 | 0.32 | −0.20 | 5 |
| 68 | 7-11-5-3          | −6.53 | −2.96 | 2.78 | 2.35 | 2.87 | 0.535 | 0.43 | −0.09 | 4 |
| 69 | 7-6-4             | −5.99 | −2.52 | 2.63 | 2.35 | 2.89 | 0.318 | 0.28 | −0.26 | 3 |
| 70 | 7-12-6-4          | −6.24 | −2.73 | 2.66 | 2.35 | 2.91 | 0.314 | 0.32 | −0.24 | 4 |
| 71 | 7-8-13-6-2        | −6.34 | −2.82 | 2.67 | 2.34 | 2.85 | 0.278 | 0.32 | −0.19 | 5 |
| 72 | 7-10-12-6         | −6.25 | −2.71 | 2.70 | 2.34 | 2.93 | 0.344 | 0.36 | −0.23 | 4 |
| 73 | 7-10-6-4          | −6.17 | −2.69 | 2.64 | 2.34 | 2.89 | 0.352 | 0.30 | −0.25 | 4 |
| 74 | 7-2               | −5.84 | −2.32 | 2.70 | 2.34 | 2.88 | 0.396 | 0.36 | −0.18 | 2 |
| 75 | 7-12-1-3          | −6.23 | −2.69 | 2.75 | 2.34 | 2.97 | 0.457 | 0.41 | −0.22 | 4 |
| 76 | 7-13-1            | −5.76 | −2.27 | 2.69 | 2.34 | 2.89 | 0.522 | 0.35 | −0.19 | 3 |
| 77 | 7-11-13-2-4       | −6.43 | −2.90 | 2.74 | 2.34 | 2.93 | 0.475 | 0.40 | −0.19 | 5 |
| 78 | 7-1               | −5.69 | −2.18 | 2.70 | 2.34 | 2.91 | 0.486 | 0.36 | −0.21 | 2 |
| 79 | 7-8-13-6-2-4      | −6.56 | −3.05 | 2.65 | 2.34 | 2.79 | 0.278 | 0.32 | −0.13 | 6 |

TABLE 5-continued

Computed parameters of α-DIPYR candidates that satisfy the design criteria. ('N' substitution positions follow the numbering scheme above), with the general structure shown in FIG. 24. All energies are reported in eV.

|  | N-Positions | HOMO | LUMO | $S_1$ | $T_1$ | $T_2$ | Osc. ($S_1$) | $\Delta S_1/T_1$ | $\Delta S_1/T_2$ | N-count |
|---|---|---|---|---|---|---|---|---|---|---|
| 80 | 7-11-13-6-2 | −6.43 | −2.90 | 2.70 | 2.34 | 2.89 | 0.298 | 0.36 | −0.19 | 5 |
| 81 | 7-10-12-6-1 | −6.33 | −2.84 | 2.66 | 2.34 | 2.88 | 0.343 | 0.32 | −0.22 | 5 |
| 82 | 7-10-6-1 | −6.07 | −2.61 | 2.62 | 2.34 | 2.91 | 0.340 | 0.28 | −0.29 | 4 |
| 83 | 7-9-11-6 | −6.42 | −2.86 | 2.74 | 2.33 | 2.90 | 0.399 | 0.41 | −0.16 | 4 |
| 84 | 7-10-4 | −5.95 | −2.47 | 2.68 | 2.33 | 2.90 | 0.490 | 0.35 | −0.22 | 3 |
| 85 | 7-10-12-6-4 | −6.44 | −2.93 | 2.68 | 2.33 | 2.89 | 0.349 | 0.34 | −0.21 | 5 |
| 86 | 7-12-6-1 | −6.13 | −2.65 | 2.64 | 2.33 | 2.91 | 0.304 | 0.30 | −0.28 | 4 |
| 87 | 7-13-4 | −5.85 | −2.37 | 2.69 | 2.33 | 2.90 | 0.504 | 0.36 | −0.21 | 3 |
| 88 | 7-9-11-6-1 | −6.50 | −2.99 | 2.68 | 2.33 | 2.85 | 0.385 | 0.35 | −0.17 | 5 |
| 89 | 7-6-1 | −5.90 | −2.45 | 2.60 | 2.33 | 2.91 | 0.305 | 0.27 | −0.31 | 3 |
| 90 | 7-12-4 | −6.01 | −2.51 | 2.69 | 2.33 | 2.90 | 0.416 | 0.36 | −0.21 | 3 |
| 91 | 7-11-13-5-3 | −6.59 | −3.06 | 2.76 | 2.33 | 2.84 | 0.557 | 0.43 | −0.08 | 5 |
| 92 | 7-8-10-6-2-4 | −6.67 | −3.17 | 2.64 | 2.32 | 2.79 | 0.256 | 0.31 | −0.16 | 6 |
| 93 | 7-13-2 | −5.91 | −2.41 | 2.70 | 2.32 | 2.90 | 0.433 | 0.37 | −0.20 | 3 |
| 94 | 7-9-11-6-4 | −6.60 | −3.08 | 2.70 | 2.32 | 2.86 | 0.395 | 0.38 | −0.16 | 5 |
| 95 | 7-12-2 | −6.08 | −2.56 | 2.70 | 2.32 | 2.90 | 0.353 | 0.38 | −0.20 | 3 |
| 96 | 7-11-6-2-4 | −6.56 | −3.10 | 2.60 | 2.32 | 2.80 | 0.239 | 0.29 | −0.19 | 5 |
| 97 | 7-8-12-6-2 | −6.48 | −2.97 | 2.65 | 2.31 | 2.81 | 0.213 | 0.33 | −0.16 | 5 |
| 98 | 7-8-6-2-4 | −6.47 | −2.99 | 2.61 | 2.31 | 2.81 | 0.216 | 0.30 | −0.19 | 5 |
| 99 | 7-11-13-1-4 | −6.27 | −2.81 | 2.69 | 2.31 | 2.87 | 0.546 | 0.38 | −0.18 | 5 |
| 100 | 7-9-11-13-6-1 | −6.59 | −3.08 | 2.61 | 2.31 | 2.80 | 0.000 | 0.30 | −0.19 | 6 |
| 101 | 7-8-13-6-1-4 | −6.41 | −2.97 | 2.60 | 2.31 | 2.73 | 0.338 | 0.29 | −0.13 | 6 |
| 102 | 7-13-6-2 | −6.10 | −2.63 | 2.63 | 2.31 | 2.84 | 0.267 | 0.32 | −0.21 | 4 |
| 103 | 7-13-2-4 | −6.10 | −2.62 | 2.68 | 2.31 | 2.87 | 0.438 | 0.37 | −0.19 | 4 |
| 104 | 7-11-1-4 | −6.20 | −2.73 | 2.69 | 2.31 | 2.90 | 0.508 | 0.38 | −0.21 | 4 |
| 105 | 7-11-13-6-1-4 | −6.50 | −3.08 | 2.60 | 2.31 | 2.71 | 0.362 | 0.29 | −0.11 | 6 |
| 106 | 7-11-5-1-3 | −6.62 | −3.08 | 2.69 | 2.31 | 2.86 | 0.000 | 0.38 | −0.17 | 5 |
| 107 | 7-12-6-2 | −6.28 | −2.79 | 2.62 | 2.30 | 2.87 | 0.218 | 0.32 | −0.25 | 4 |
| 108 | 7-9-6-3 | −6.37 | −2.87 | 2.69 | 2.30 | 2.84 | 0.398 | 0.39 | −0.15 | 4 |
| 109 | 7-8-10-12-6-2-4 | −6.92 | −3.43 | 2.64 | 2.30 | 2.76 | 0.249 | 0.34 | −0.12 | 7 |
| 110 | 7-10-6-2 | −6.21 | −2.75 | 2.60 | 2.30 | 2.86 | 0.243 | 0.30 | −0.26 | 4 |
| 111 | 7-9-13-6-3 | −6.48 | −2.96 | 2.72 | 2.30 | 2.97 | 0.451 | 0.42 | −0.25 | 5 |
| 112 | 7-10-13-6-1 | −6.17 | −2.73 | 2.63 | 2.30 | 2.83 | 0.410 | 0.33 | −0.20 | 5 |
| 113 | 7-6-2 | −6.03 | −2.58 | 2.58 | 2.30 | 2.88 | 0.211 | 0.28 | −0.30 | 3 |
| 114 | 7-2-4 | −6.03 | −2.56 | 2.67 | 2.30 | 2.89 | 0.388 | 0.37 | −0.22 | 3 |
| 115 | 7-13-5-3 | −6.27 | −2.77 | 2.71 | 2.30 | 2.86 | 0.520 | 0.41 | −0.15 | 4 |
| 116 | 7-8-12-6-2-4 | −6.70 | −3.21 | 2.63 | 2.30 | 2.78 | 0.221 | 0.33 | −0.16 | 6 |
| 117 | 7-10-12-6-2 | −6.48 | −2.99 | 2.64 | 2.30 | 2.84 | 0.255 | 0.35 | −0.20 | 5 |
| 118 | 7-9-10-6-3 | −6.58 | −3.07 | 2.71 | 2.30 | 2.97 | 0.436 | 0.41 | −0.26 | 5 |
| 119 | 7-12-2-4 | −6.27 | −2.78 | 2.68 | 2.30 | 2.90 | 0.362 | 0.38 | −0.22 | 4 |
| 120 | 7-10-2-4 | −6.21 | −2.74 | 2.67 | 2.30 | 2.89 | 0.417 | 0.37 | −0.23 | 4 |
| 121 | 7-5-3 | −6.20 | −2.69 | 2.72 | 2.29 | 2.87 | 0.489 | 0.43 | −0.15 | 3 |
| 122 | 7-9-11-13-6-4 | −6.70 | −3.17 | 2.68 | 2.29 | 2.86 | 0.000 | 0.39 | −0.17 | 6 |
| 123 | 7-10-12-2-4 | −6.47 | −2.99 | 2.68 | 2.29 | 2.87 | 0.384 | 0.39 | −0.19 | 5 |
| 124 | 7-10-5-3 | −6.38 | −2.88 | 2.71 | 2.29 | 2.88 | 0.506 | 0.42 | −0.17 | 4 |
| 125 | 7-8-10-6-1-4 | −6.52 | −3.09 | 2.59 | 2.29 | 2.77 | 0.320 | 0.31 | −0.18 | 6 |
| 126 | 7-9-11-13-6 | −6.50 | −2.96 | 2.73 | 2.28 | 2.90 | 0.000 | 0.45 | −0.16 | 5 |
| 127 | 7-9-13-6-1-3 | −6.54 | −3.09 | 2.66 | 2.28 | 2.89 | 0.443 | 0.38 | −0.23 | 6 |
| 128 | 7-9-11-6-2 | −6.64 | −3.14 | 2.66 | 2.28 | 2.83 | 0.288 | 0.38 | −0.16 | 5 |
| 129 | 7-11-6-1-4 | −6.43 | −3.03 | 2.56 | 2.28 | 2.77 | 0.320 | 0.28 | −0.20 | 5 |
| 130 | 7-12-5-3 | −6.44 | −2.93 | 2.72 | 2.28 | 2.87 | 0.430 | 0.44 | −0.15 | 4 |
| 131 | 7-10-13-6 | −6.08 | −2.63 | 2.66 | 2.28 | 2.89 | 0.413 | 0.38 | −0.23 | 4 |
| 132 | 7-10-13-6-4 | −6.26 | −2.82 | 2.64 | 2.28 | 2.84 | 0.415 | 0.36 | −0.20 | 5 |
| 133 | 7-13-6-2-4 | −6.31 | −2.88 | 2.57 | 2.28 | 2.81 | 0.251 | 0.29 | −0.24 | 5 |
| 134 | 7-8-10-13-6-2-4 | −6.76 | −3.33 | 2.60 | 2.28 | 2.73 | 0.306 | 0.33 | −0.13 | 7 |
| 135 | 7-10-12-6-2-4 | −6.69 | −3.24 | 2.60 | 2.27 | 2.78 | 0.247 | 0.32 | −0.19 | 6 |
| 136 | 7-10-12-5-3 | −6.64 | −3.14 | 2.71 | 2.27 | 2.84 | 0.446 | 0.43 | −0.14 | 5 |
| 137 | 7-9-12-6-3 | −6.63 | −3.12 | 2.69 | 2.27 | 2.95 | 0.337 | 0.42 | −0.26 | 5 |
| 138 | 7-8-10-13-6-1-4 | −6.61 | −3.22 | 2.57 | 2.27 | 2.68 | 0.360 | 0.30 | −0.11 | 7 |
| 139 | 7-9-10-12-6-3 | −6.86 | −3.34 | 2.58 | 2.27 | 2.74 | 0.000 | 0.32 | −0.16 | 6 |
| 140 | 7-11-5 | −6.16 | −2.69 | 2.68 | 2.27 | 2.84 | 0.478 | 0.42 | −0.15 | 3 |
| 141 | 7-13-5-1-3 | −6.36 | −2.89 | 2.65 | 2.27 | 2.83 | 0.000 | 0.38 | −0.18 | 5 |
| 142 | 7-8-6-1-4 | −6.32 | −2.92 | 2.56 | 2.27 | 2.78 | 0.281 | 0.30 | −0.22 | 5 |
| 143 | 7-13-1-4 | −5.95 | −2.54 | 2.63 | 2.27 | 2.85 | 0.506 | 0.36 | −0.22 | 4 |
| 144 | 7-9-11-6-2-4 | −6.85 | −3.40 | 2.61 | 2.27 | 2.76 | 0.279 | 0.35 | −0.15 | 6 |
| 145 | 7-12-6-2-4 | −6.48 | −3.06 | 2.56 | 2.26 | 2.80 | 0.211 | 0.30 | −0.24 | 5 |
| 146 | 7-9-6 | −6.06 | −2.60 | 2.64 | 2.26 | 2.85 | 0.367 | 0.38 | −0.20 | 3 |
| 147 | 7-8-12-6-1-4 | −6.54 | −3.13 | 2.58 | 2.26 | 2.76 | 0.279 | 0.32 | −0.18 | 6 |
| 148 | 7-9-10-6-1-3 | −6.64 | −3.20 | 2.65 | 2.26 | 2.92 | 0.421 | 0.39 | −0.27 | 6 |
| 149 | 7-9-11-13-6-2-4 | −6.94 | −3.46 | 2.58 | 2.26 | 2.73 | 0.000 | 0.32 | −0.15 | 7 |
| 150 | 7-11-5-1 | −6.26 | −2.79 | 2.69 | 2.25 | 2.90 | 0.508 | 0.44 | −0.21 | 4 |
| 151 | 7-10-6-2-4 | −6.41 | −3.02 | 2.53 | 2.25 | 2.81 | 0.233 | 0.28 | −0.28 | 5 |
| 152 | 7-10-13-6-2 | −6.30 | −2.87 | 2.61 | 2.25 | 2.78 | 0.320 | 0.36 | −0.17 | 5 |

TABLE 5-continued

Computed parameters of α-DIPYR candidates that satisfy the design criteria. ('N' substitution positions follow the numbering scheme above), with the general structure shown in FIG. 24. All energies are reported in eV.

| | N-Positions | HOMO | LUMO | $S_1$ | $T_1$ | $T_2$ | Osc. ($S_1$) | $\Delta S_1/T_1$ | $\Delta S_1/T_2$ | N-count |
|---|---|---|---|---|---|---|---|---|---|---|
| 153 | 7-9-11-5-3 | −6.80 | −3.31 | 2.73 | 2.25 | 2.80 | 0.526 | 0.47 | −0.07 | 5 |
| 154 | 7-9-11-13-6-1-4 | −6.78 | −3.38 | 2.51 | 2.25 | 2.66 | 0.000 | 0.25 | −0.16 | 7 |
| 155 | 7-11-5-4 | −6.35 | −2.89 | 2.68 | 2.25 | 2.89 | 0.501 | 0.43 | −0.21 | 4 |
| 156 | 7-9-11-13-6-2 | −6.72 | −3.22 | 2.66 | 2.25 | 2.83 | 0.000 | 0.40 | −0.18 | 6 |
| 157 | 7-9-10-6 | −6.25 | −2.79 | 2.65 | 2.25 | 2.92 | 0.395 | 0.40 | −0.26 | 4 |
| 158 | 7-9-10-12-6-1-3 | −6.93 | −3.46 | 2.51 | 2.25 | 2.69 | 0.000 | 0.26 | −0.18 | 7 |
| 159 | 7-9-13-6-1 | −6.22 | −2.80 | 2.61 | 2.25 | 2.85 | 0.401 | 0.37 | −0.23 | 5 |
| 160 | 7-11-13-5-1 | −6.32 | −2.88 | 2.67 | 2.25 | 2.90 | 0.541 | 0.43 | −0.23 | 5 |
| 161 | 7-9-6-1-3 | −6.43 | −3.02 | 2.61 | 2.25 | 2.81 | 0.371 | 0.36 | −0.20 | 5 |
| 162 | 7-10-12-5-1-3 | −6.72 | −3.24 | 2.64 | 2.24 | 2.83 | 0.000 | 0.40 | −0.19 | 6 |
| 163 | 7-13-6-1-4 | −6.16 | −2.82 | 2.52 | 2.24 | 2.74 | 0.324 | 0.27 | −0.22 | 5 |
| 164 | 7-10-5-1-3 | −6.46 | −2.99 | 2.70 | 2.24 | 2.89 | 0.518 | 0.46 | −0.19 | 5 |
| 165 | 7-6-2-4 | −6.23 | −2.86 | 2.51 | 2.24 | 2.83 | 0.206 | 0.26 | −0.32 | 4 |
| 166 | 7-10-13-2-4 | −6.29 | −2.89 | 2.63 | 2.24 | 2.83 | 0.448 | 0.39 | −0.20 | 5 |
| 167 | 7-12-1-4 | −6.11 | −2.70 | 2.63 | 2.24 | 2.87 | 0.426 | 0.39 | −0.24 | 4 |
| 168 | 7-9-10-13-6-3 | −6.70 | −3.22 | 2.54 | 2.24 | 2.63 | 0.000 | 0.30 | −0.09 | 6 |
| 169 | 7-10-12-6-1-4 | −6.53 | −3.16 | 2.55 | 2.24 | 2.76 | 0.312 | 0.31 | −0.21 | 6 |
| 170 | 7-9-13-6 | −6.15 | −2.69 | 2.67 | 2.24 | 2.92 | 0.410 | 0.43 | −0.25 | 4 |
| 171 | 7-9-6-4 | −6.23 | −2.82 | 2.59 | 2.24 | 2.82 | 0.351 | 0.35 | −0.22 | 4 |
| 172 | 7-9-13-6-4 | −6.33 | −2.89 | 2.64 | 2.24 | 2.87 | 0.408 | 0.40 | −0.23 | 5 |
| 173 | 7-9-11-6-1-4 | −6.69 | −3.32 | 2.56 | 2.24 | 2.74 | 0.346 | 0.32 | −0.18 | 6 |
| 174 | 7-10-1-4 | −6.04 | −2.65 | 2.62 | 2.24 | 2.88 | 0.481 | 0.38 | −0.26 | 4 |
| 175 | 7-9-10-6-4 | −6.43 | −3.01 | 2.62 | 2.24 | 2.86 | 0.386 | 0.38 | −0.25 | 5 |
| 176 | 7-10-13-5-3 | −6.46 | −3.05 | 2.65 | 2.24 | 2.82 | 0.508 | 0.41 | −0.17 | 5 |
| 177 | 7-1-4 | −5.88 | −2.49 | 2.61 | 2.24 | 2.90 | 0.457 | 0.38 | −0.28 | 3 |
| 178 | 7-5-1-3 | −6.29 | −2.81 | 2.70 | 2.24 | 2.86 | 0.487 | 0.47 | −0.16 | 4 |
| 179 | 7-9-10-6-1 | −6.32 | −2.92 | 2.59 | 2.24 | 2.84 | 0.378 | 0.36 | −0.25 | 5 |
| 180 | 7-12-5-1-3 | −6.52 | −3.04 | 2.70 | 2.23 | 2.87 | 0.000 | 0.46 | −0.18 | 5 |
| 181 | 7-5 | −5.86 | −2.42 | 2.64 | 2.23 | 2.84 | 0.451 | 0.41 | −0.20 | 2 |
| 182 | 7-11-13-5-4 | −6.41 | −2.98 | 2.67 | 2.23 | 2.90 | 0.529 | 0.44 | −0.23 | 5 |
| 183 | 7-11-13-5 | −6.21 | −2.79 | 2.66 | 2.23 | 2.83 | 0.494 | 0.43 | −0.17 | 4 |
| 184 | 7-9-6-1 | −6.12 | −2.74 | 2.56 | 2.23 | 2.81 | 0.340 | 0.33 | −0.25 | 4 |
| 185 | 7-10-13-5-1-3 | −6.55 | −3.14 | 2.57 | 2.23 | 2.75 | 0.000 | 0.34 | −0.18 | 6 |
| 186 | 7-9-11-5-1-3 | −6.89 | −3.42 | 2.57 | 2.23 | 2.76 | 0.000 | 0.34 | −0.19 | 6 |
| 187 | 7-9-12-6-1-3 | −6.68 | −3.25 | 2.63 | 2.23 | 2.93 | 0.337 | 0.40 | −0.30 | 6 |
| 188 | 7-9-12-6 | −6.31 | −2.85 | 2.64 | 2.23 | 2.93 | 0.321 | 0.42 | −0.28 | 4 |
| 189 | 7-11-5-2 | −6.41 | −2.95 | 2.66 | 2.22 | 2.89 | 0.382 | 0.43 | −0.23 | 4 |
| 190 | 7-10-13-1-4 | −6.14 | −2.79 | 2.59 | 2.22 | 2.78 | 0.509 | 0.37 | −0.19 | 5 |
| 191 | 7-12-6-1-4 | −6.33 | −2.99 | 2.51 | 2.22 | 2.78 | 0.277 | 0.29 | −0.26 | 5 |
| 192 | 7-10-5 | −6.02 | −2.62 | 2.62 | 2.22 | 2.83 | 0.461 | 0.40 | −0.21 | 3 |
| 193 | 7-13-5 | −5.91 | −2.51 | 2.62 | 2.22 | 2.82 | 0.472 | 0.40 | −0.20 | 3 |
| 194 | 7-9-12-6-4 | −6.49 | −3.06 | 2.61 | 2.22 | 2.88 | 0.322 | 0.40 | −0.27 | 5 |
| 195 | 7-13-5-1 | −6.00 | −2.60 | 2.63 | 2.22 | 2.87 | 0.506 | 0.41 | −0.24 | 4 |
| 196 | 7-9-10-12-6-1 | −6.59 | −3.16 | 2.58 | 2.22 | 2.75 | 0.000 | 0.36 | −0.17 | 6 |
| 197 | 7-12-5 | −6.08 | −2.66 | 2.63 | 2.21 | 2.82 | 0.401 | 0.42 | −0.19 | 3 |
| 198 | 7-11-5-2-4 | −6.62 | −3.18 | 2.64 | 2.21 | 2.79 | 0.000 | 0.42 | −0.15 | 5 |
| 199 | 7-9-10-12-6-4 | −6.71 | −3.27 | 2.61 | 2.21 | 2.77 | 0.000 | 0.40 | −0.16 | 6 |
| 200 | 7-13-5-4 | −6.10 | −2.70 | 2.63 | 2.21 | 2.86 | 0.495 | 0.41 | −0.23 | 4 |
| 201 | 7-9-10-12-6 | −6.52 | −3.07 | 2.65 | 2.21 | 2.80 | 0.000 | 0.44 | −0.14 | 5 |
| 202 | 7-9-13-6-2 | −6.37 | −2.95 | 2.61 | 2.21 | 2.80 | 0.317 | 0.40 | −0.19 | 5 |
| 203 | 7-9-6-2 | −6.27 | −2.88 | 2.56 | 2.21 | 2.78 | 0.258 | 0.35 | −0.23 | 4 |
| 204 | 7-9-12-6-1 | −6.36 | −2.96 | 2.58 | 2.21 | 2.85 | 0.320 | 0.38 | −0.27 | 5 |
| 205 | 7-9-10-6-2 | −6.47 | −3.07 | 2.58 | 2.21 | 2.81 | 0.294 | 0.38 | −0.22 | 5 |
| 206 | 7-5-4 | −6.04 | −2.64 | 2.62 | 2.20 | 2.88 | 0.458 | 0.42 | −0.26 | 3 |
| 207 | 7-10-5-4 | −6.21 | −2.82 | 2.62 | 2.20 | 2.89 | 0.477 | 0.42 | −0.27 | 4 |
| 208 | 7-12-5-4 | −6.28 | −2.86 | 2.63 | 2.20 | 2.89 | 0.421 | 0.43 | −0.25 | 4 |
| 209 | 7-9-10-13-6-1 | −6.43 | −3.04 | 2.50 | 2.20 | 2.60 | 0.000 | 0.30 | −0.10 | 6 |
| 210 | 7-9-13-6-2-4 | −6.57 | −3.19 | 2.56 | 2.20 | 2.77 | 0.295 | 0.36 | −0.21 | 6 |
| 211 | 7-10-5-1 | −6.12 | −2.71 | 2.63 | 2.20 | 2.91 | 0.486 | 0.43 | −0.28 | 4 |
| 212 | 7-5-1 | −5.95 | −2.54 | 2.63 | 2.20 | 2.89 | 0.463 | 0.43 | −0.26 | 3 |
| 213 | 7-11-13-5-2 | −6.46 | −3.04 | 2.64 | 2.20 | 2.91 | 0.408 | 0.44 | −0.27 | 5 |
| 214 | 7-12-5-1 | −6.17 | −2.76 | 2.63 | 2.19 | 2.90 | 0.427 | 0.44 | −0.27 | 4 |
| 215 | 7-10-12-5-1 | −6.37 | −2.96 | 2.63 | 2.19 | 2.86 | 0.445 | 0.43 | −0.23 | 5 |
| 216 | 7-10-12-5 | −6.27 | −2.88 | 2.60 | 2.19 | 2.80 | 0.401 | 0.41 | −0.20 | 4 |
| 217 | 7-10-12-5-4 | −6.47 | −3.07 | 2.62 | 2.19 | 2.85 | 0.431 | 0.43 | −0.23 | 5 |
| 218 | 7-9-10-12-6-2 | −6.75 | −3.32 | 2.60 | 2.19 | 2.76 | 0.000 | 0.41 | −0.16 | 6 |
| 219 | 7-9-12-6-2 | −6.52 | −3.12 | 2.58 | 2.19 | 2.82 | 0.252 | 0.40 | −0.23 | 5 |
| 220 | 7-11-5-1-4 | −6.47 | −3.07 | 2.57 | 2.19 | 2.65 | 0.000 | 0.38 | −0.08 | 5 |
| 221 | 7-9-10-13-6-4 | −6.55 | −3.15 | 2.57 | 2.19 | 2.65 | 0.000 | 0.38 | −0.09 | 6 |
| 222 | 7-9-10-6-2-4 | −6.67 | −3.32 | 2.53 | 2.18 | 2.77 | 0.274 | 0.35 | −0.24 | 6 |
| 223 | 7-9-10-12-6-2-4 | −6.96 | −3.56 | 2.54 | 2.18 | 2.71 | 0.000 | 0.35 | −0.18 | 7 |
| 224 | 7-9-13-5-3 | −6.53 | −3.13 | 2.65 | 2.18 | 2.81 | 0.510 | 0.47 | −0.17 | 5 |
| 225 | 7-5-2 | −6.09 | −2.69 | 2.61 | 2.18 | 2.87 | 0.359 | 0.43 | −0.26 | 3 |

TABLE 5-continued

Computed parameters of α-DIPYR candidates that satisfy the design criteria. ('N' substitution positions follow the numbering scheme above), with the general structure shown in FIG. 24. All energies are reported in eV.

| | N-Positions | HOMO | LUMO | $S_1$ | $T_1$ | $T_2$ | Osc. ($S_1$) | $\Delta S_1/T_1$ | $\Delta S_1/T_2$ | N-count |
|---|---|---|---|---|---|---|---|---|---|---|
| 226 | 7-13-5-2 | −6.15 | −2.76 | 2.60 | 2.18 | 2.86 | 0.394 | 0.42 | −0.26 | 4 |
| 227 | 7-9-13-6-1-4 | −6.41 | −3.11 | 2.50 | 2.18 | 2.70 | 0.354 | 0.33 | −0.20 | 6 |
| 228 | 7-9-10-13-6 | −6.36 | −2.96 | 2.60 | 2.18 | 2.67 | 0.000 | 0.42 | −0.08 | 5 |
| 229 | 7-10-5-2 | −6.27 | −2.87 | 2.60 | 2.18 | 2.90 | 0.378 | 0.42 | −0.29 | 4 |
| 230 | 7-9-5-3 | −6.44 | −3.04 | 2.64 | 2.17 | 2.79 | 0.471 | 0.46 | −0.15 | 4 |
| 231 | 7-12-5-2 | −6.33 | −2.92 | 2.61 | 2.17 | 2.89 | 0.333 | 0.44 | −0.28 | 4 |
| 232 | 7-13-5-2-4 | −6.36 | −2.97 | 2.61 | 2.17 | 2.79 | 0.415 | 0.44 | −0.18 | 5 |
| 233 | 7-9-11-5-4 | −6.63 | −3.24 | 2.64 | 2.17 | 2.82 | 0.501 | 0.47 | −0.18 | 5 |
| 234 | 7-10-13-5-1 | −6.20 | −2.86 | 2.58 | 2.17 | 2.80 | 0.502 | 0.41 | −0.22 | 5 |
| 235 | 7-9-12-6-2-4 | −6.73 | −3.36 | 2.53 | 2.17 | 2.77 | 0.239 | 0.36 | −0.24 | 6 |
| 236 | 7-9-13-5-1-3 | −6.61 | −3.23 | 2.52 | 2.17 | 2.71 | 0.000 | 0.35 | −0.20 | 6 |
| 237 | 7-10-12-5-2 | −6.52 | −3.13 | 2.60 | 2.17 | 2.86 | 0.346 | 0.43 | −0.26 | 5 |
| 238 | 7-9-10-13-6-2-4 | −6.79 | −3.42 | 2.50 | 2.17 | 2.60 | 0.000 | 0.33 | −0.10 | 7 |
| 239 | 7-10-12-5-2-4 | −6.74 | −3.34 | 2.60 | 2.16 | 2.76 | 0.000 | 0.44 | −0.16 | 6 |
| 240 | 7-12-5-2-4 | −6.54 | −3.14 | 2.61 | 2.16 | 2.79 | 0.348 | 0.45 | −0.18 | 5 |
| 241 | 7-9-10-13-6-2 | −6.58 | −3.20 | 2.55 | 2.16 | 2.64 | 0.000 | 0.39 | −0.09 | 6 |
| 242 | 7-10-5-2-4 | −6.48 | −3.10 | 2.60 | 2.16 | 2.81 | 0.395 | 0.44 | −0.21 | 5 |
| 243 | 7-9-10-12-6-1-4 | −6.79 | −3.46 | 2.50 | 2.16 | 2.68 | 0.000 | 0.34 | −0.18 | 7 |
| 244 | 7-13-5-1-4 | −6.21 | −2.87 | 2.53 | 2.16 | 2.63 | 0.000 | 0.38 | −0.10 | 5 |
| 245 | 7-5-2-4 | −6.30 | −2.92 | 2.59 | 2.16 | 2.84 | 0.368 | 0.44 | −0.24 | 4 |
| 246 | 7-10-13-5-4 | −6.29 | −2.97 | 2.57 | 2.15 | 2.80 | 0.488 | 0.42 | −0.23 | 5 |
| 247 | 7-10-13-5 | −6.10 | −2.79 | 2.55 | 2.15 | 2.79 | 0.457 | 0.40 | −0.24 | 4 |
| 248 | 7-9-11-5-2-4 | −6.91 | −3.51 | 2.55 | 2.15 | 2.72 | 0.000 | 0.40 | −0.17 | 6 |
| 249 | 7-9-12-5-3 | −6.69 | −3.30 | 2.62 | 2.15 | 2.81 | 0.394 | 0.47 | −0.19 | 5 |
| 250 | 7-9-11-13-5-4 | −6.71 | −3.34 | 2.60 | 2.14 | 2.78 | 0.000 | 0.45 | −0.18 | 6 |
| 251 | 7-10-12-5-1-4 | −6.58 | −3.22 | 2.54 | 2.14 | 2.63 | 0.000 | 0.39 | −0.09 | 6 |
| 252 | 7-10-13-5-2-4 | −6.56 | −3.22 | 2.56 | 2.14 | 2.73 | 0.000 | 0.43 | −0.17 | 6 |
| 253 | 7-9-5-1-3 | −6.50 | −3.14 | 2.62 | 2.13 | 2.78 | 0.476 | 0.48 | −0.16 | 5 |
| 254 | 7-10-5-1-4 | −6.32 | −2.99 | 2.58 | 2.13 | 2.68 | 0.473 | 0.45 | −0.09 | 5 |
| 255 | 7-12-5-1-4 | −6.38 | −3.03 | 2.58 | 2.13 | 2.66 | 0.000 | 0.44 | −0.08 | 5 |
| 256 | 7-10-13-5-2 | −6.34 | −3.02 | 2.55 | 2.13 | 2.80 | 0.402 | 0.42 | −0.24 | 5 |
| 257 | 7-5-1-4 | −6.15 | −2.82 | 2.57 | 2.12 | 2.70 | 0.445 | 0.45 | −0.12 | 4 |
| 258 | 7-9-13-5-1 | −6.26 | −2.94 | 2.58 | 2.12 | 2.81 | 0.506 | 0.45 | −0.24 | 5 |
| 259 | 7-9-5 | −6.10 | −2.77 | 2.56 | 2.12 | 2.77 | 0.445 | 0.45 | −0.21 | 3 |
| 260 | 7-9-12-5-1-3 | −6.76 | −3.39 | 2.58 | 2.12 | 2.78 | 0.000 | 0.47 | −0.19 | 6 |
| 261 | 7-9-5-4 | −6.28 | −2.96 | 2.56 | 2.11 | 2.79 | 0.458 | 0.45 | −0.23 | 4 |
| 262 | 7-9-13-5-4 | −6.37 | −3.05 | 2.57 | 2.11 | 2.83 | 0.491 | 0.46 | −0.25 | 5 |
| 263 | 7-9-5-1 | −6.17 | −2.85 | 2.56 | 2.10 | 2.80 | 0.465 | 0.46 | −0.24 | 4 |
| 264 | 7-9-10-5-4 | −6.48 | −3.16 | 2.57 | 2.10 | 2.84 | 0.478 | 0.46 | −0.27 | 5 |

Developing blue fluorescent (fl) dopants using aza-substituted DiPYR core with high quantum efficiencies and small singlet-triplet energy gap ($\Delta S_1/T_1 < 0.4$ eV).

By screening a library of blue fluorescent emitters and estimating their respective $S_1$, $T_1$, HOMO, and LUMO energies, the best candidates of emitters suitable for a hybrid WOLED can be identified. Using this information, promising candidates acting as blue fl dopants with high quantum efficiencies and small singlet-triplet energy gap ($\Delta S_1/T_1 < 0.4$ eV) have been successfully synthesized and characterized. Their photophysical and electrochemical properties in both solution and solid matrices have been analyzed as presented herein. This combined theoretical/experimental approach allowed us to rapidly target potential candidates that matches the criteria of hybrid blue fluorescent ("fl") emitters.

Figure 25:
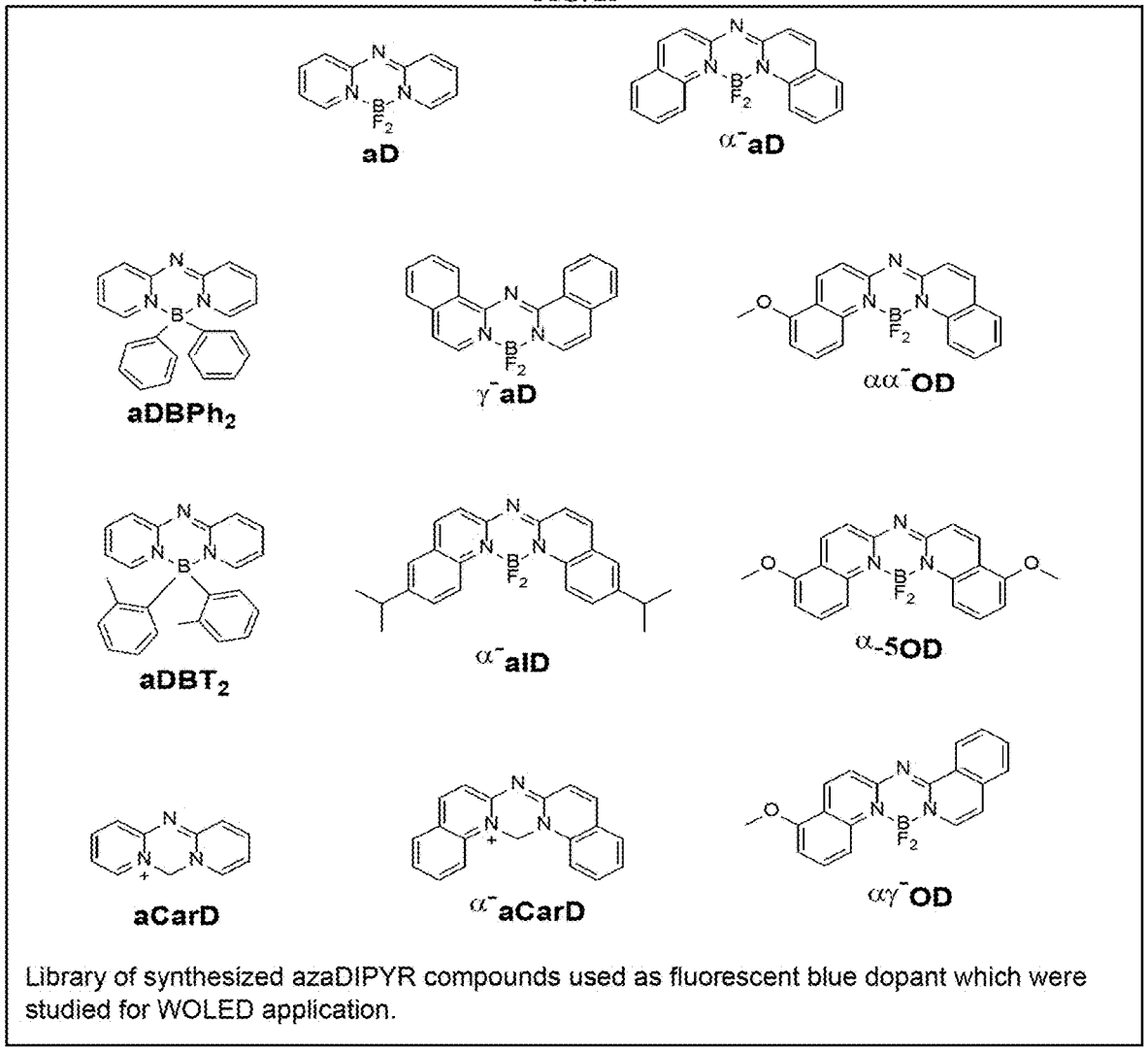
FIG. 25 shows structures of complexes selected as blue emitters according to embodiments disclosed herein.

In the present work, our efforts were focused on synthesizing derivatives of difluoro-boron-azaDiPYR complexes. Boyer and coworkers first discovered these complexes in the early nineties, but little information is known about their application in OLED devices. Recently, new synthetic procedures of aza-substituted DiPYR complexes emerged inspiring a new family of dyes to investigate. The target complexes acting as blue emitters are shown in FIG. 25. These dyes strongly absorb in the UV-blue part of the spectrum and display blue fluorescence ($\lambda_{em}$=400-470 nm) with high quantum yields in solution and when doped in thin films ($\Phi$=42%-86%).

Figure 26:
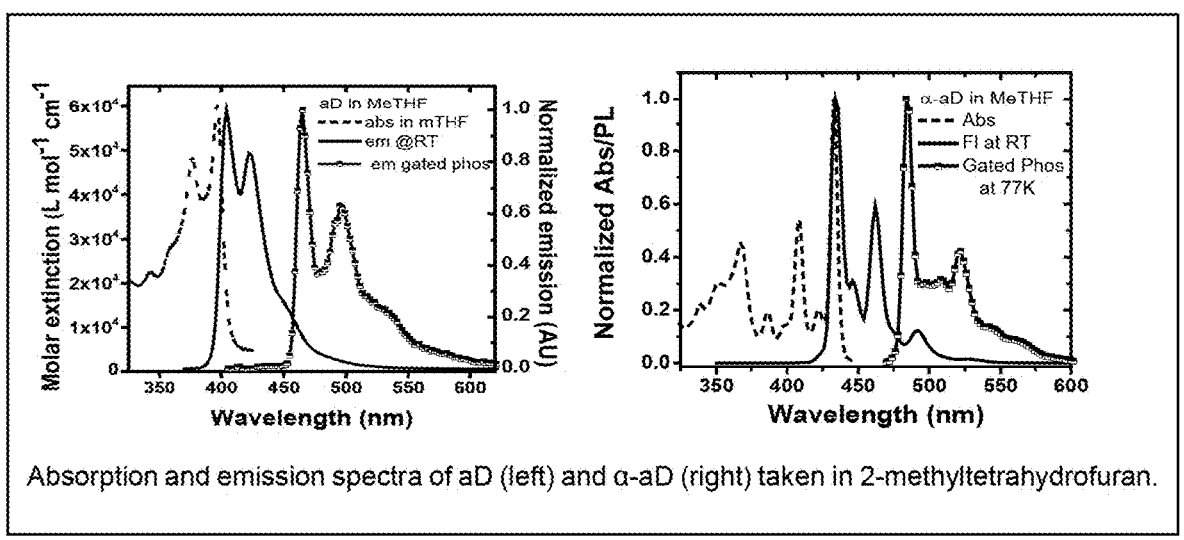
FIG. 26 shows absorption and emission spectra of aD and α-aD taken in 2-methyltetrahydrofuran according to embodiments disclosed herein.

The absorption and emission spectra of the parent aD and the benzannulated derivatives such as α-aD and others are shown in FIG. 26, These complexes exhibit strong π to π* absorption bands and intense fluorescence emission in the visible spectrum. The parent aD complex has violet-blue fluorescence emission ($\lambda_{em, max}$=405 nm) that is the mirror image of the $S_0$ to $S_1$ transition ($\lambda_{abs, max}$=398 nm). In the UV region of the absorption spectra, the $S_0$ to $S_2$ transition centered at 270 nm also appears as a vibrational absorption feature. For the benzannulated derivatives such as α-aD, both the absorption and emission profile are red shifted compared to the parent aD. This information increases the number of potential candidates of Host materials with high HOMO and low LUMO energies that can nest the latter blue emitter complex. The gated phosphorescence emission (shown in half-filled boxed lines in FIG. 27 taken at low temperatures (77 K) after 500 μs delay time represents the lowest triplet energy ($T_1$).

Table 6 compares the singlet and triplet energies for the respective complexes from the calculated methods to the experimental data. Clearly, the computational data of the singlet-triplet energy gap closely matches the experimental data. The α-aD has a small singlet-triplet energy gap of $\Delta S_1/T_1 \leq 0.3$ eV that meets the criteria of developing blue fl dopants for hybrid WOLED, and the parent aD has a singlet-triplet energy gap of $\Delta S_1/T_1 \leq 0.5$ eV. The HOMO and LUMO energies recorded in Table 7 were derived from electrochemical data using Ferrocene as an internal standard in acetonitrile solvent. From the DFT calculations, we were able to understand that the higher quantum yield of α-aD ($\Phi_f$=86%) in solution was a result of the relative reordering of the $S_1$ and $T_2$ energies upon benzaimulation of the parent structure. The reason the parent aD has a lower quantum yield ($\Phi_f$=42%) is because the energy of $T_2$ states is just below the $S_1$ state, enabling fast intersystem crossing that is competitive with fluorescence. All photophysical parameters for the unsubstituted DiPYR derivative aD and the benzannulated derivatives like α-aD complexes present in solution and doped in 1 wt % in PMMA films are summarized in Table 8. Note that the quantum efficiency of α-aD remains high in both solution and solid state ($\Phi_f$=86%), maintaining a small singlet-triplet energy gap necessary for blue fl emitter in the hybrid WOLED.

The experimental HOMO energies of γ-aD (6.14 eV) and α-aD (6.21 eV) deviated from the calculated HOMO energies by 0.63-0.7 eV. Common hosts such as mCBP, CBP, DPEPO have shallower HOMO energies which doesn't nest these fl-dopants. As a result, excimer formation is observed when doped in these different host materials. From DFT modelling, our data suggests that by decorating the aza-DiPYR compounds with electron donating functional groups in specific positions, we can destabilize the HOMO energy thus making it shallower. Following this approach, not only the HOMO/LUMO energies will be suitable to be hosted in host materials but we can also maintain the high quantum yield and the small singlet-triplet energy gap ($\Delta S_1/T_1<0.3$ eV) necessary used for developing blue fl dopant materials for hybrid WOLED.

TABLE 6

Singlet and Triplet energies deduced from calculations and experimental data for aza-substituted DiPYRs

| | Calculated results[a] | | | Experimental results[b] | | |
|---|---|---|---|---|---|---|
| | $S_1$ (eV/nm) | $T_1$ (eV/nm) | $\Delta E(S_1/T_1)$ | $S_1$ (eV/nm) | $T_1$ (eV/nm) | $\Delta E(S_1/T_1)$ |
| aD | 3.16 (392 nm) | 2.65 (468 nm) | 0.51 | 3.11 (398 nm) | 2.64 (469 nm) | 0.47 |
| aDBPh$_2$ | 2.86 (433 nm) | 2.51 (493 nm) | 0.35 | 2.89 eV (429 nm) | 2.68 eV (463 nm) | 0.21 |
| aDBT$_2$ | 2.65 eV (467 nm) | 2.37 eV (523 nm) | 0.28 | 2.82 eV (440 nm) | — | — |
| α-aD | 2.78 (446 nm) | 2.39 (518 nm) | 0.39 | 2.86 (434 nm) | 2.56 (484 nm) | 0.30 |
| γ-aD | 2.78 (446 nm) | 2.39 (518 nm) | 0.39 | 2.87 (432 nm) | 2.57 (482 nm) | 0.30 |
| α-aID | 2.65 (467 nm) | 2.34 (529 nm) | 0.31 | 2.79 (444 nm) | 2.51 (494 nm) | 0.28 |
| α-5OD | 2.79 (444 nm) | 2.47 (502 nm) | 0.32 | 2.77 (447 nm) | 2.51 (493 nm) | 0.26 |
| αα-OD | 2.77 (447 nm) | 2.43 (510 nm) | 0.34 | 2.81 (442 nm) | 2.53 (490 nm) | 0.28 |
| αγ-OD | 2.78 (446 nm) | 2.43 (510 nm) | 0.35 | 2.84 (437 nm) | 2.46 (503 nm) | 0.38 |

[a] TD-DFT B3LYP/6-311G**

[b] Singlets are extrapolated from peak max of Fl (298 K) and Triplets from gated phos (77 K) in 2-MeTHF.

Figure 27:
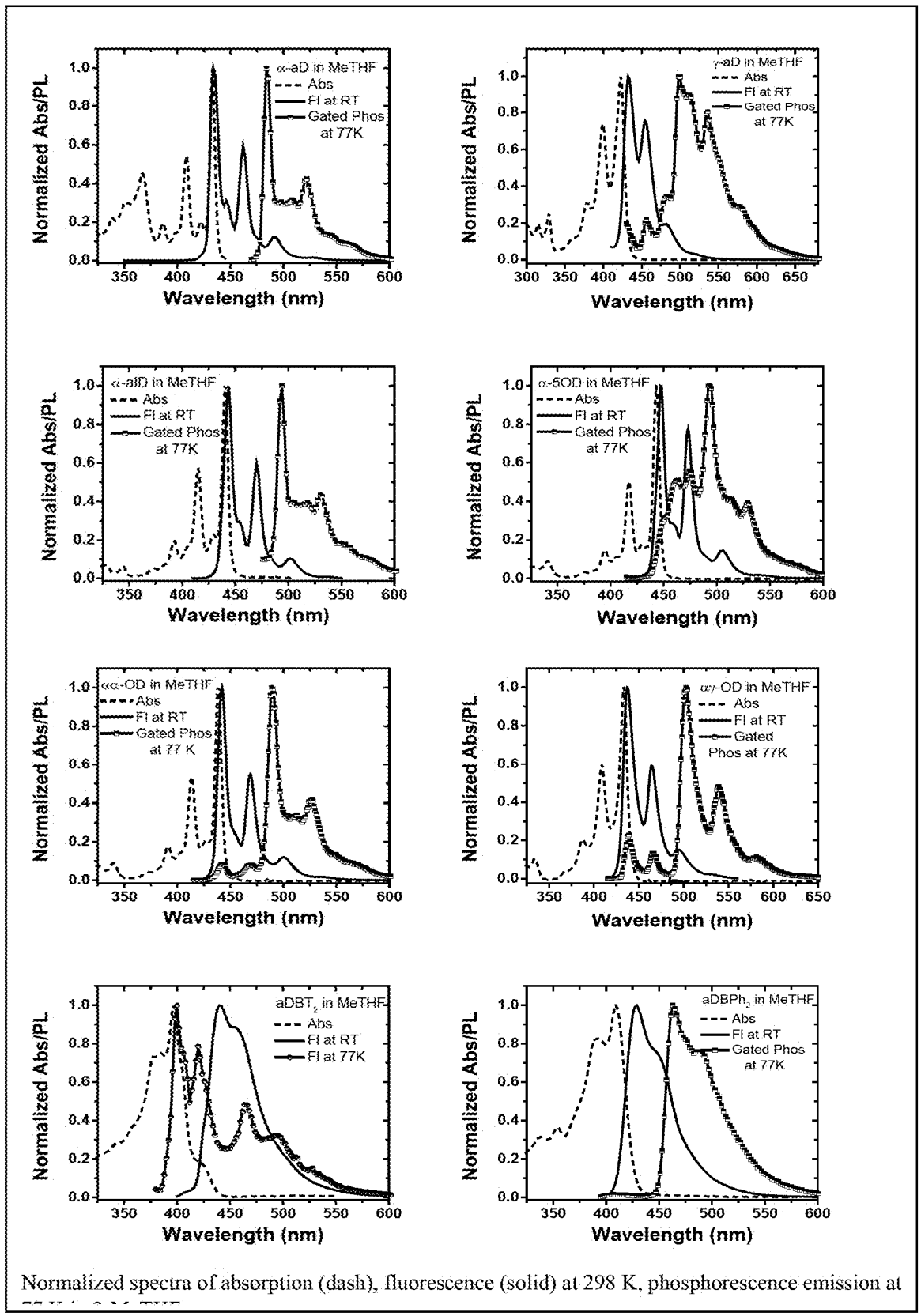
FIG. 27 shows normalized spectra of absorption, fluorescence at 298 K, and phosphorescence emission at 77 K in 2-MeTHF according to embodiments disclosed herein.

The photophysical characterizations are shown in FIG. 27. Each spectrum shows the absorption and emission profile for the respective aza-substituted DiPYRs in 2-methyltetrahydrofuran (MeTHF). All compounds have a small stoke shift gap between the absorption and emission. The singlet energies were extrapolated from the peak maximum of the fluorescence emission taken at room temperature, and the triplet energies were deduced from the gated phosphorescence emission taken at 77 K after 500 μs pulse-delay time from excitation. It's noteworthy to mention that the excited state lifetime of the singlet-state fluorescence is about 2 to 4 ns, and the triplet-state phosphorescence is long-lived (milliseconds). The quantum yield for these newly synthesized aza-substituted DiPYRs have maintained the high quantum yield ($\Phi_f \geq 0.85$) like the parent α-aD with radiative decays of $10^8$ s$^{-1}$ and non-radiative decays of $10^7$ s$^{-1}$.

TABLE 7

Photophysical properties of blue fl dopant emitters in 2-MeTHF.

| | $\Phi_n$ | τ (ns) | $k_r$ (s$^{-1}$) | $k_{nr}$ (s$^{-1}$) |
|---|---|---|---|---|
| aD | 0.42 | 2.11 | $2 \times 10^8$ | $2.74 \times 10^8$ |
| α-aD | 0.86 | 3.25 | $2.65 \times 10^8$ | $4.31 \times 10^7$ |
| γ-aD | 0.87 | 3.16 | $2.75 \times 10^8$ | $4.11 \times 10^7$ |
| α-aID | 0.87 | 3.82 | $2.27 \times 10^8$ | $3.40 \times 10^7$ |
| α-5OD | 0.84 | 3.48 | $2.41 \times 10^8$ | $4.60 \times 10^7$ |
| αα-OD | 0.84 | 3.28 | $2.56 \times 10^8$ | $4.89 \times 10^7$ |
| αγ-OD | 0.90 | 2.81 | $3.20 \times 10^8$ | $3.56 \times 10^7$ |
| aDBT$_2$ | 0.22 | 2.35 | $0.93 \times 10^8$ | $3.32 \times 10^8$ |
| aDBPh$_2$ | 0.30 | 2.08 | $1.44 \times 10^8$ | $3.37 \times 10^8$ |
| aCarD | 0.42 | 2.11 | $2.00 \times 10^8$ | $2.09 \times 10^7$ |
| α-aCarD | 0.76 | 6.74 | $1.13 \times 10^8$ | $0.35 \times 10^7$ |

$\Phi_{fl}$: Quantum Yield
τ: excited state lifetime
$k_r$: radiative decay
$k_{nr}$: nonradiative decay Table 6 summarizes the singlet and triplet energy gaps deduced from the calculated and experimental values. The newly synthesized aza-substituted DiPYRs have a small singlet-triplet energy gaps ($\Delta S_1/T_1 \leq 0.4$ eV) with a triplet energy above 2.50 eV making them suitable as blue dopant materials that can shuttle triplet excitons to green and red phosphors in WOLED. However, the αγ-OD compound has a triplet energy of 2.46 eV, making it difficult to transfer triplets to green phosphors (2.5 eV), but might be suitable for yellow and red emitters. The quantum yield for these compounds remained high ($\Phi_f \geq 0.85$) in solution (MeTHF) as well as in a polymer matrix such as PMMA. All these derivatives are still to be tested in in blue OLEDs and hybrid WOLED. Our data suggests that the symmetric methoxy DiPYR (α-5OD) blue fl dopant (triplet energy above 2.51 eV) with shallower HOMO/LUMO energies (-5.92 eV/- 2.38 eV) will be suitable to be hosted in the new host materials shown from the previous report.

Since the synthesis of the substituted α-aD core took 6-7 steps to make, it is worth considering other substitution sites which may effectively provide us a similar destabilization of the HOMO energy while increasing the steric bulk of the molecule to minimize any potential self-quenching when doped at high concentrations. Additional compounds were synthesized where —BF$_2$, was replaced with —B(Ph)$_2$ or —B(Tolyl)$_2$, named aDBPh$_2$ and aDBT$_2$ respectively. Their photophysical spectra are shared in FIG. 27. As shown in Table 6, the HOMO of aDBPh$_2$ obtained from electrochem is -5.62 eV, which is shallower than the -6.21 eV value of α-aD. The triplet of aDBPh2 is also well above 2.50 eV, making them suitable as blue dopant materials that can shuttle triplet excitons to green and red phosphors in WOLED. However, the fast nonradiative rates and low quantum yields of aDBT$_2$ and aDBPh$_2$ compared to aD, suggests that the deactivation pathway observed in aD is enhanced by the addition of the bulky groups. A tactic we are using to circumvent this problem is by substituting bulky groups on the boron atom of the α-aD core. As we learned from the aD and α-aD core structures, the benzannulation should destabilize the T2 enough to minimize the contribution of intersystem, crossing as a nonradiative decay pathway. It is expected that, by adding phenyl groups or tolyl groups to the boron atom of α-aD, a comparable oxidation potential to that of aDBPh$_2$, but with quantum yield and lifetime values comparable to α-aD is achievable.

Figure 28:
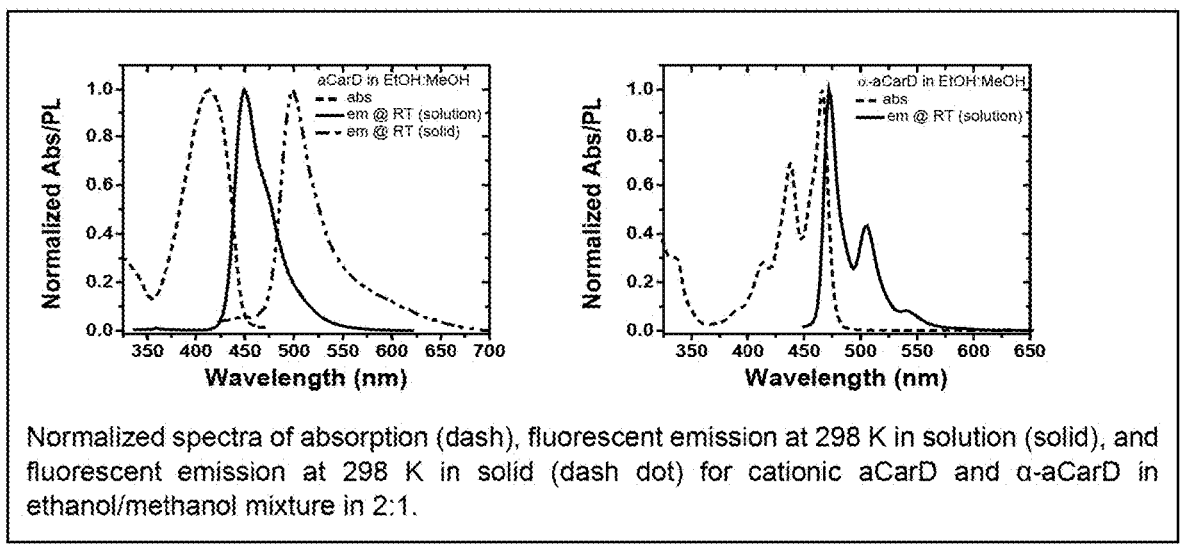
FIG. 28 shows normalized spectra of absorption, fluorescent emission at 298 K in solution, and fluorescent emission at 298 K in solid for cationic aCarD and α-aCarD according to embodiments disclosed herein.

Additionally, cationic derivatives of the azaDIPYR core have been synthesized as shown in FIG. 28 which has emission wavelength red-shifted by 30-50 nm to its boron counterpart. Although the cationic derivatives may not be the best system for WOLED applications, making neutral derivatives by introducing groups such as carboxylic acid substituents in the structure. The deprotonation of the carboxylic acid proton produces an overall neutral structure which will have a reasonable oxidation and reduction potentials as fluorescent blue dopants.

Figure 29:
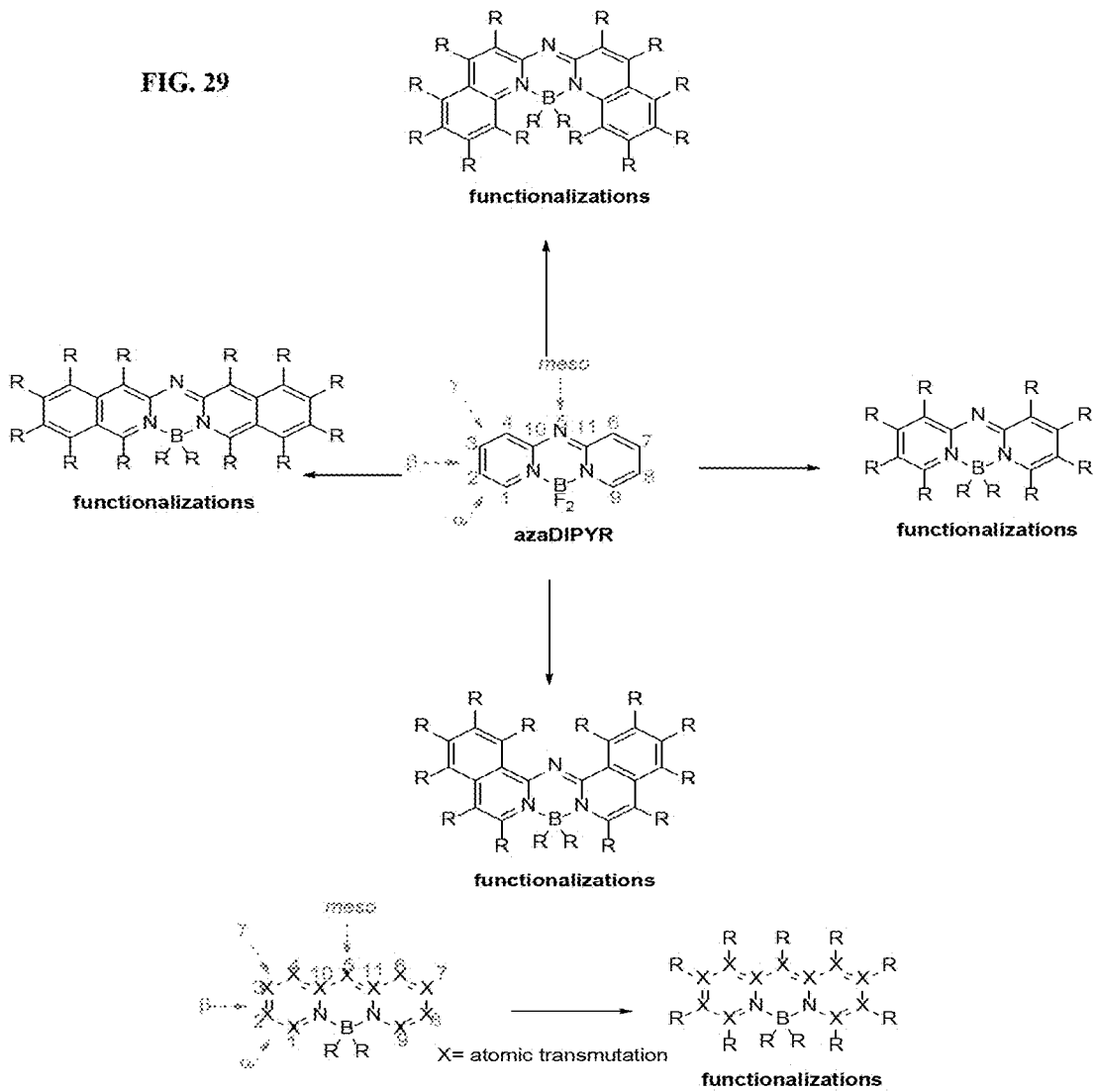
FIG. 29 shows example structures of the azaDIPYR core modified either by substitution with electron donor or withdrawing group according to embodiments disclosed herein.

Techniques to modify the azaDIPYR, α-azaDIPYR, and g-azaDIPYR core, which are the foundations upon which the modeling and photophysical descriptions are built, have been disclosed herein. Subsequently, a series of modifications to the basic structures are disclosed. In all cases, any —CH— position may be functionalized as —CR—, where —R is an alkyl, aryl, donor, or acceptor group, is a deuterated or otherwise isotopically functionalized atom, or is another atom, either a metal or main group element. This also includes benzannulation and applies to any —CH— position in any of the derivatives outlined herein. Any X shown in FIG. 29 represents any atomic transmutation in the core structure that may be of interest including but not limited to multiple nitrogen atoms in the core structure.

Substituted azaDIPYR/DIPYR Dyes

The azaDIPYR core based on the device data disclosed herein are interesting material which has photophysical properties to BODIPY but are synthetically more accessible to modify. The azaDIPYR family are great candidates to use as blue fluorescent dopants for WOLED. As shown from our data from the molecules illustrated in FIG. 27 that tuning the HOMO/LUMO energies can be achieved by addition of substituents or asymmetry to the core structure. Development of blue fluorophores from the core azaDIPYR and α-azaDIPYR can be expanded with other electron donating, electron donating and other substituents in addition to the methoxy, isopropyl, tolyl and phenyl groups. The Boron atom in the core structure can also be replaced with other metals.

Additionally, by tactful placement of electron-withdrawing/electron-donating groups, design parameters can be tuned as indicated by the DFT results summarized in Table 8.

TABLE 8

Figure 30:
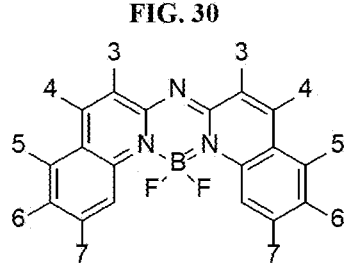
FIG. 30 shows structures for α-aD derivatives according to embodiments disclosed herein.

DFT (B3LYP/6-31G**) calculated properties for α-aD derivatives. (The candidates are named based on the nature and site of substitution following the scheme in FIG. 30)

| | $S_1$ (eV) | $S_1$ (nm) | $T_1$ (eV) | $T_1$ (nm) | $\Delta S_1/T_1$ (eV) | HOMO (eV) | LUMO (eV) |
|---|---|---|---|---|---|---|---|
| α-aD | 2.73 | 454 | 2.39 | 519 | 0.34 | −5.62 | −2.07 |
| OMe | | | | | | | |
| α-aD-(OMe)$_2$-3 | 2.64 | 470 | 2.25 | 550 | 0.38 | −5.31 | −1.90 |
| α-aD-(OMe)$_2$-4 | 2.92 | 425 | 2.67 | 465 | 0.25 | −5.41 | −1.62 |
| α-aD-(OMe)$_2$-5 | 2.79 | 444 | 2.47 | 502 | 0.33 | −5.45 | −1.81 |
| α-aD-(OMe)$_2$-6 | 2.49 | 498 | 2.19 | 567 | 0.31 | −5.25 | −1.95 |
| α-aD-(OMe)$_2$-7 | 2.65 | 468 | 2.36 | 525 | 0.29 | −5.36 | −1.90 |
| Mes | | | | | | | |
| α-aD-(Mes)$_2$-3 | 2.70 | 459 | 2.38 | 521 | 0.32 | −5.58 | −2.04 |
| α-aD-(Mes)$_2$-4 | 2.71 | 457 | 2.41 | 515 | 0.30 | −5.52 | −1.96 |
| α-aD-(Mes)$_2$-5 | 2.71 | 458 | 2.40 | 517 | 0.31 | −5.55 | −2.01 |
| α-aD-(Mes)$_2$-6 | 2.66 | 466 | 2.36 | 525 | 0.30 | −5.58 | −2.07 |
| α-aD-(Mes)$_2$-7 | 2.63 | 472 | 2.38 | 522 | 0.25 | −5.55 | −2.07 |
| CN | | | | | | | |
| α-aD-(CN)$_2$-3 | 2.64 | 470 | 2.37 | 523 | 0.27 | −6.28 | −2.79 |
| α-aD-(CN)$_2$-4 | 2.38 | 521 | 2.04 | 608 | 0.34 | −6.30 | −3.14 |
| α-aD-(CN)$_2$-5 | 2.62 | 473 | 2.31 | 536 | 0.31 | −6.31 | −2.87 |
| α-aD-(CN)$_2$-6 | 2.66 | 466 | 2.36 | 525 | 0.30 | −6.35 | −2.89 |
| α-aD-(CN)$_2$-7 | 2.62 | 474 | 2.34 | 531 | 0.28 | −6.30 | −2.83 |
| F | | | | | | | |
| α-aD-(F)$_2$-3 | 2.68 | 462 | 2.30 | 540 | 0.39 | −5.80 | −2.34 |
| α-aD-(F)$_2$-4 | 2.85 | 434 | 2.56 | 485 | 0.30 | −5.84 | −2.14 |
| α-aD-(F)$_2$-5 | 2.78 | 446 | 2.43 | 510 | 0.35 | −5.86 | −2.26 |
| α-aD-(F)$_2$-6 | 2.64 | 470 | 2.30 | 539 | 0.34 | −5.73 | −2.28 |
| α-aD-(F)$_2$-7 | 2.74 | 453 | 2.40 | 516 | 0.34 | −5.78 | −2.25 |

Figure 31:
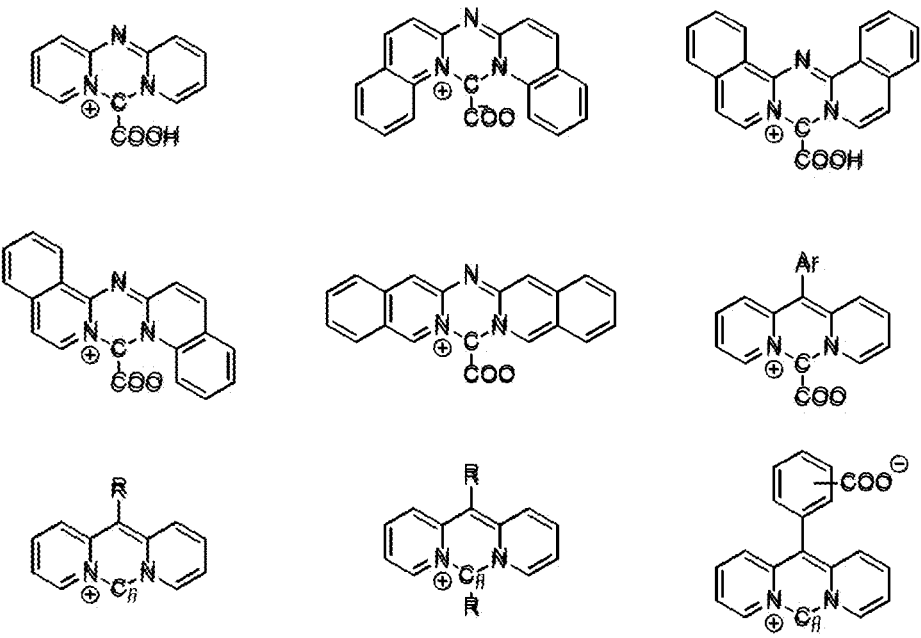
FIG. 31 shows structures of carDIPYR compounds according to embodiments disclosed herein.

Carbon-coordinated azaDIPYRs (acarDIPYRs): Boron has been shown to be an excellent coordinating atom for DIPYRs and BODIPYs, forming stable pseudo-aromatic fluorophores with high photoluminescent quantum yields. We have also shown that carbon can be used in lieu of a metal or main group element to produce bright emission in the solution and solid states. The resulting unsubstituted dye carDIPYR is cationic, with a delocalized positive charge shared between both nitrogens. The counteranion can be exchanged with for suitable anion (for example halogens, such as iodide and bromide, have been used, as, has PF6-) to meet specific application requirements. We have shown in FIG. 27, that we had successfully characterized a cationic derivative of azaDIPYR (aCarD) and α-azaCARDIPYR (α-aCarD). We are interested in these cationic species, but more specifically the neutral derivatives of these systems which are shown in FIG. 31. Similar substitution patterns can be applied to the ones mentioned in the substituted azaDIPYR/DIPYR dyes section.

Host Materials for fl/ph Hybrid WOLEDs

Using the data and techniques disclosed herein, it is also possible to identify and prepare host materials that can nest the energy levels of blue fluorescent dopant and host the singlet and triplet energy of green, yellow and red phosphorescent emitters. Blue fluorescent emitters with strong blue fluorescence in the solid-state that can act as host material for green, yellow and red phosphors are also presented in this section.

Figure 32:
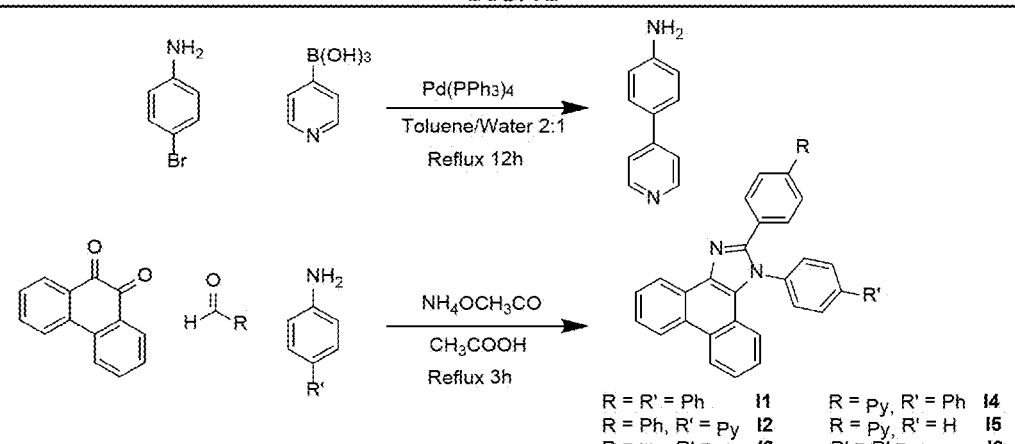
FIG. 32 shows synthesis of phenanthro[9,10-d]imidazoles according to embodiments disclosed herein.
Figure 33:
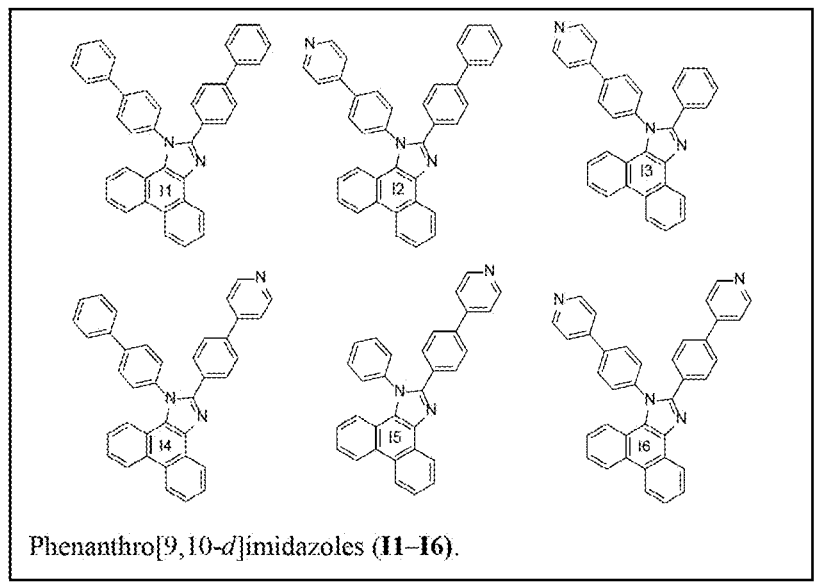
FIG. 33 shows structures of Phenanthro[9,10-d]imidazoles (I1-I6) according to embodiments disclosed herein.

We have identified phenanthro[9,10-d]imidazoles as potential materials that can serve these two purposes. Based on our modeling studies, we selected and synthesized six phenanthro[9,10-d]imidazoles, i.e. I1-I6 (using Schemes 3a, 3b shown in FIGS. 32 and 33, respectively), also identified as "H2P" compounds previously, which have the potential for use as hosts, dopants and neat fluorescent emitters for hybrid-fluorescent white organic light emitting diode (WOLED). The materials are obtained in high yields (>80%) and are purified by filtration followed by sublimation.

Figure 34:
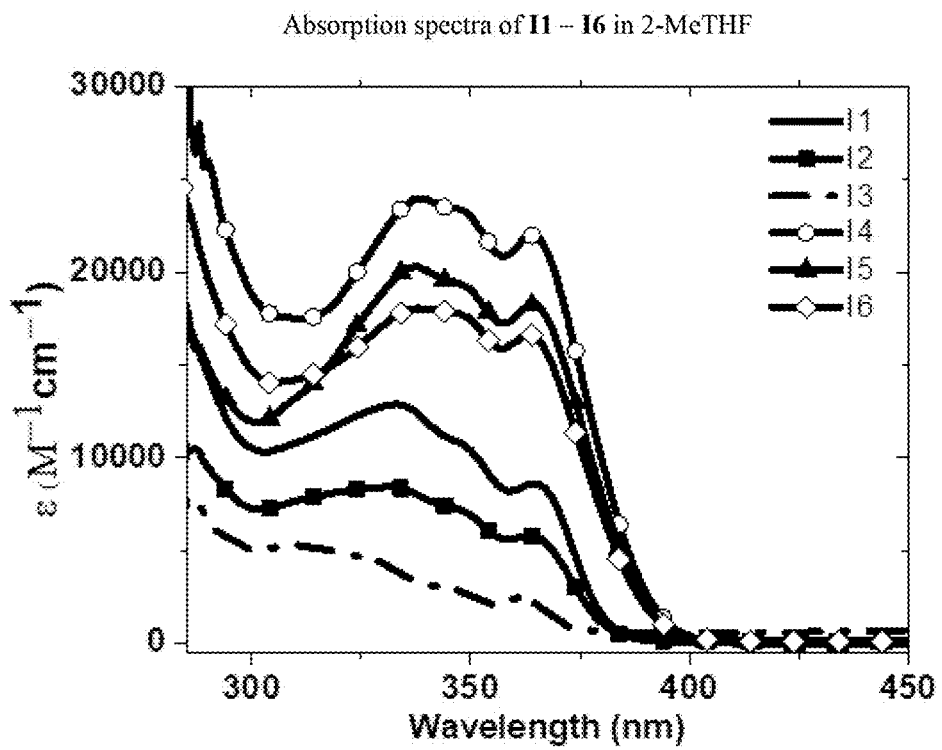
FIG. 34 shows the absorption spectra of compounds I1-I6 in 2-MeTHF according to embodiments disclosed herein.
Figure 35:
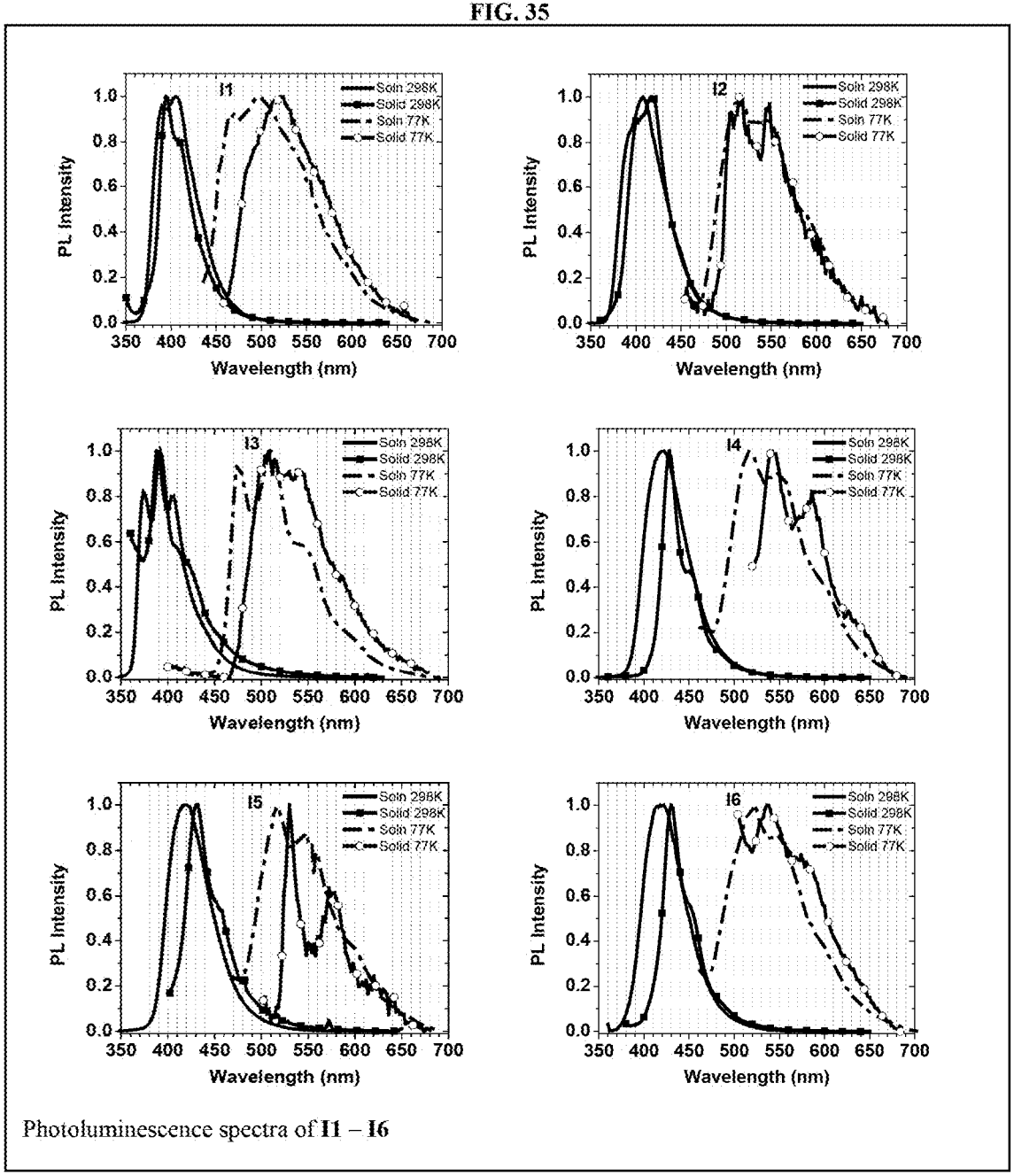
FIG. 35 shows the photoluminescence spectra of I1-I6 according to embodiments disclosed herein.

All the materials absorb in the range 310-380 nm with moderate extinction coefficients ($>10^4 M^{-1} cm^{-1}$) (FIG. 34). The emission spectra in 2-MeTHf of I1-I3 blue-shifted relative to the emission spectra of I4-I6 (FIG. 35). I1, I4, I5, and I6 have near unity photoluminescence quantum yield (PLQY), whereas I2 and I3 have PLQT less than 20% in 2-MeTHF (Table 9). To check the potential use of these materials as neat fluorescent emitters, we studied photophysical properties of these materials in neat films and solid powder. I1, I4, I5, and I6 retained high PLQY as neat films (Table 9), with their emission spectra red-shifted in neat film and solid relative to their energies in solution. Furthermore, the fluorescent spectrum of I4, I5, and I6 broadened and have the same onset with a widely used neat fluorescent emitter for hybrid WOLED (4P-NPD).

TABLE 9

Photophysical Properties of 1-I6

| | $S_1$ (Soln) | $S_1$ (Solid) | $T_1$ (Soln) | $T_1$ (Solid) | PLQY (%)[a] | PLQY (%)[b] |
|---|---|---|---|---|---|---|
| I1 | 373 | 377 | 441 | 468 | 99 | 95 |
| I2 | 375 | 382 | 477 | 490 | 28 | — |
| I3 | 365 | 370 | 460 | 478 | 28 | — |
| I4 | 390 | 412 | 478 | 520 | 99 | 55 |
| I5 | 390 | 406 | 480 | 520 | 99 | 81 |
| I6 | 386 | 410 | 475 | 495 | 99 | 83 |
| 4P-NPD | 380 | 415 | — | 525 | 69 | 57 |

[a]Measured in 2-MeTHF.
[b]neat film. All $S_1$ and $T_1$ values are in nm

Figure 36:
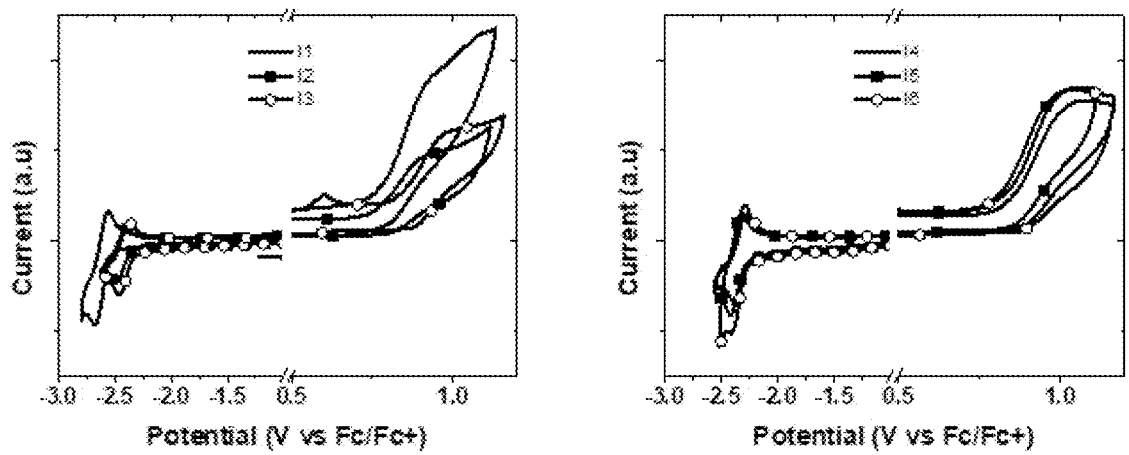
FIG. 36 shows cyclic voltammetry of phenanthro[9,10-d]imidazoles according to embodiments disclosed herein.

The electrochemical properties of these materials are summarized in Table 10. All the materials show irreversible oxidation and reversible reduction (scan rates of 0.1 V/s and 10 V/s). (FIG. 36). Their HOMO and LUMO levels are calculated from their oxidation and reduction potentials, respectively and are similar with small variations.

Because of their appropriate singlet and triplet energies, these materials can serve as host for α-aD. We doped 1 wt % of α-aD into the phenanthro[9,10-d]imidazole hosts and high PLQYs were obtained (>80%).

Prior to fabricating WOLED with these materials as hosts or neat emitter materials, we doped a green (Ir(ppy)$_3$), a yellow (Ir(bt)$_2$acac) and a red (PQIr) phosphor into these host materials (Table 10). The PLQY of the yellow and red phosphors are maintained high (>70%), whereas the efficiency of the green phosphor is low in these host materials. Preliminary results using I2, I4, I5 and I6 as fluorescent neat emitters and as host materials in WOLED are discussed below.

Figure 37:
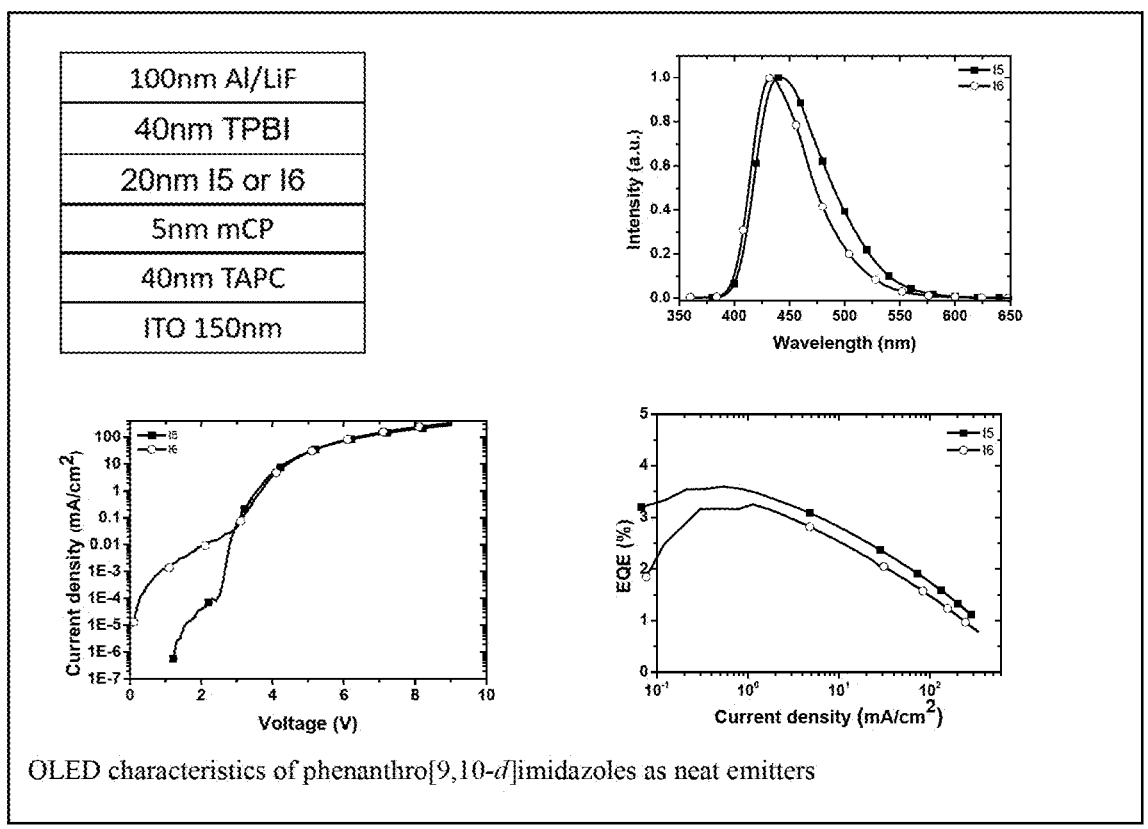
FIG. 37 shows OLED characteristics of phenanthro[9,10-d]imidazoles as neat emitters according to embodiments disclosed herein.
Figure 38:
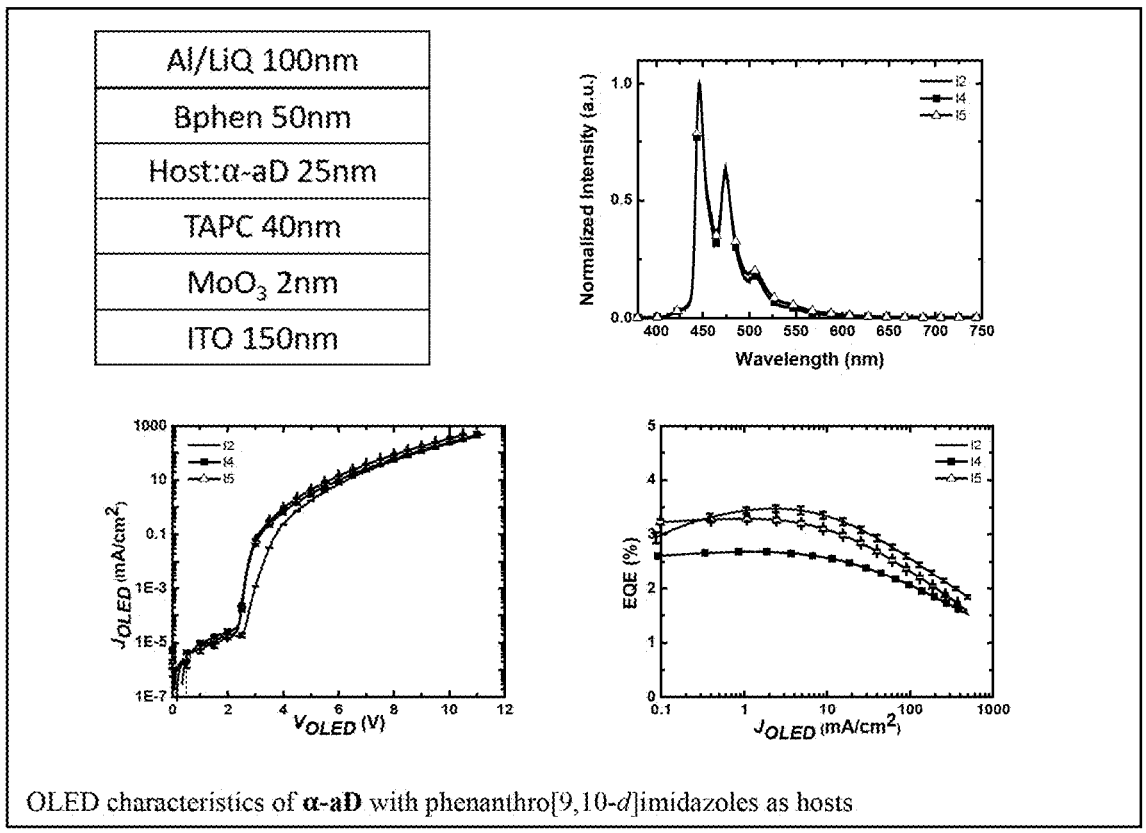
FIG. 38 shows OLED characteristics of α-aD with phenanthro[9,10-d]imidazoles as hosts according to embodiments disclosed herein.

The host materials were utilized to fabricate blue fluorescence monochromatic devices and hybrid-WOLEDs. The first set of monochromatic devices shown in FIG. 37 used either I5 or I6 as neat fluorescence emitter in the emissive layer. The second set, used I2, I4 and I5 as host materials for α-aD (FIG. 38). The EL spectrum of I5 and I6 in the first set of devices agree with their PL spectrum in neat films. Their transport properties and efficiencies are similar, reaching high EQE of 3.5 which is close to the theoretical maximum efficiency of fluorescent emitters (FIG. 37). Similarly, the α-aD based devices achieved high EQE (peak=3.5%) close to the theoretical maximum (FIG. 38). The EL spectrum of α-aD in I2, I4 or I5 host matches its PL spectrum, indicating exciton confinement on the dopant.

Figure 39:
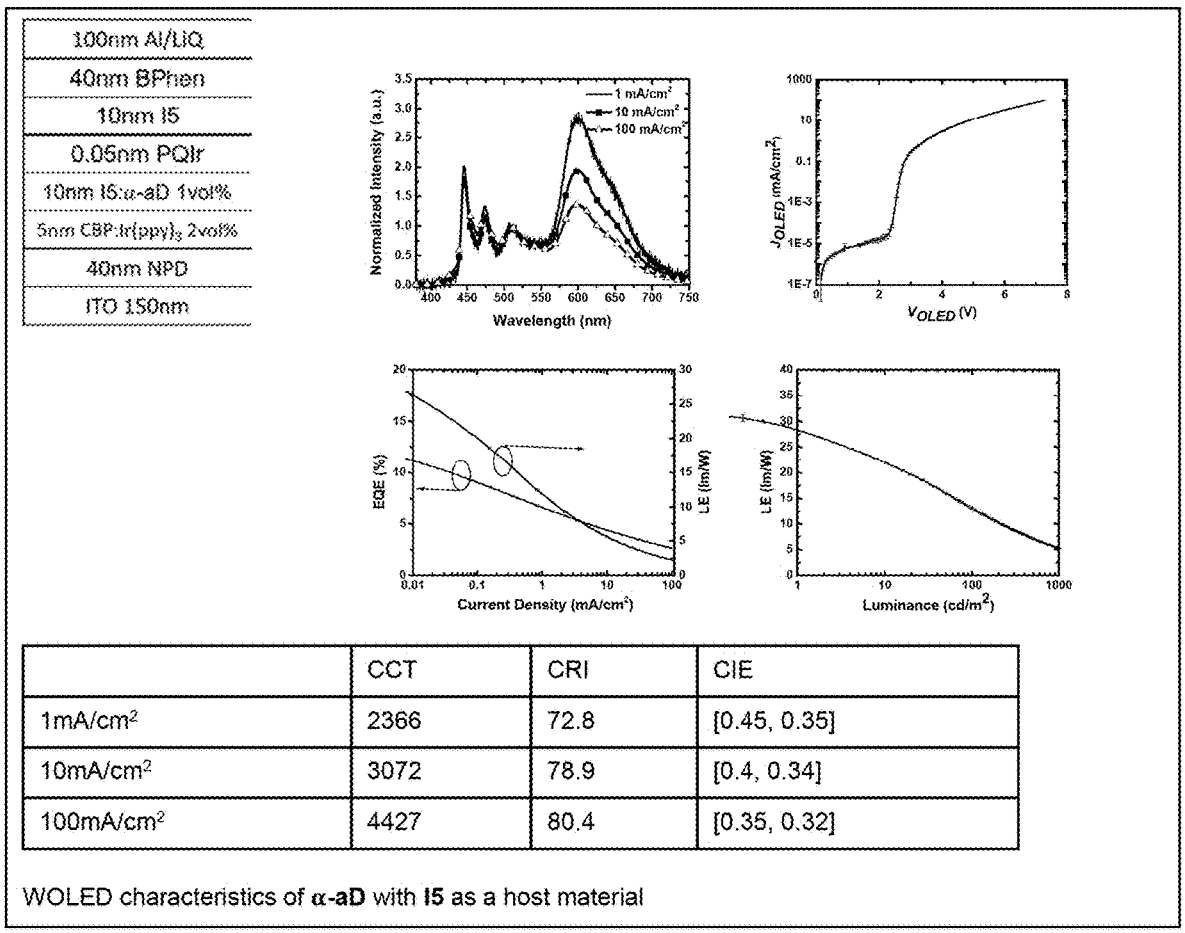
FIG. 39 shows WOLED characteristics of α-aD with I5 as a host material according to embodiments disclosed herein.
Figure 40:
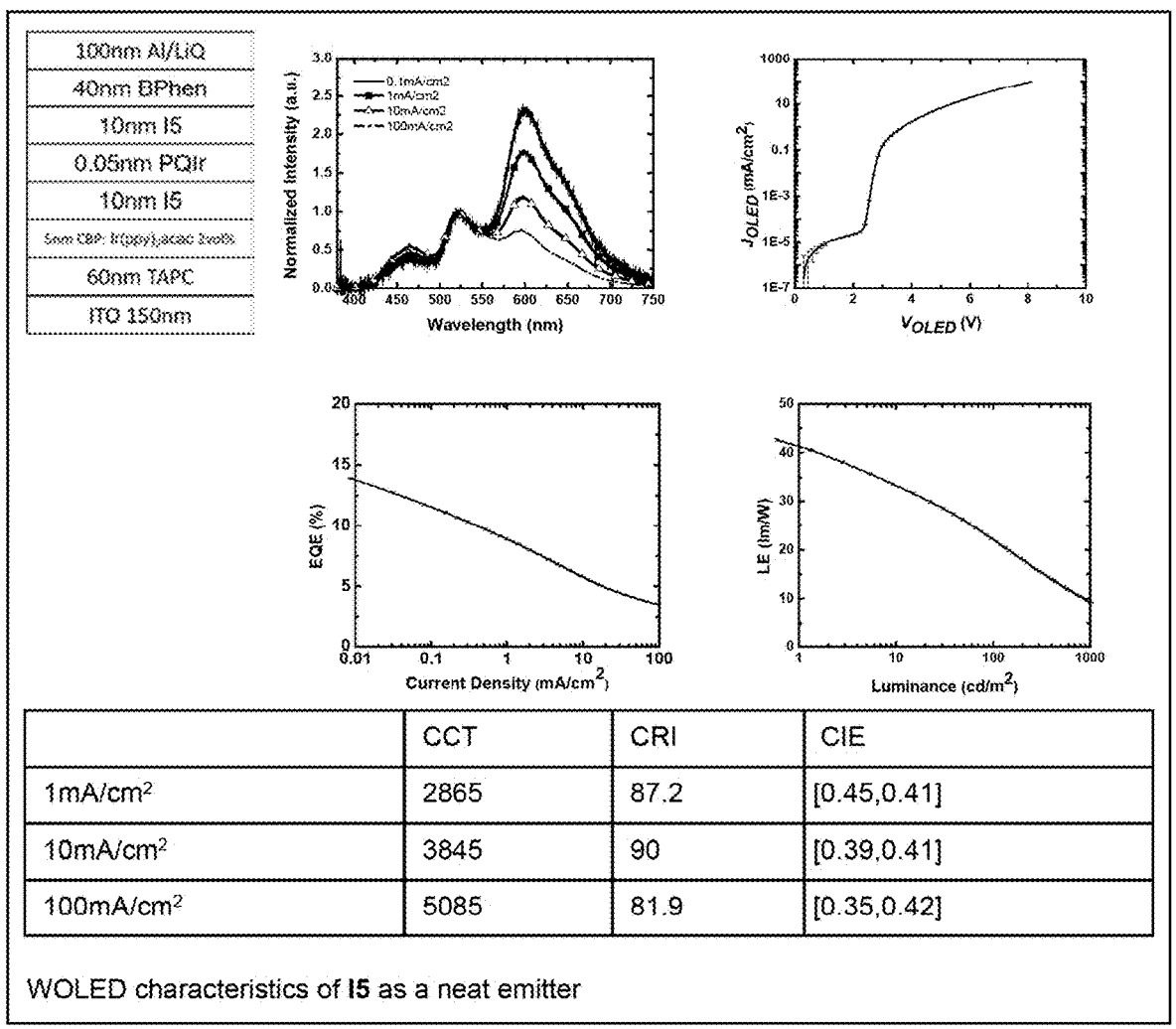
FIG. 40 shows WOLED characteristics of I5 as a neat emitter according to embodiments disclosed herein.

I5 was chosen to fabricate hybrid WOLED since good efficiencies were obtained with I5 as neat fluorescent emitter and as a host in monochromatic devices. We tested different devices with and without –aD to examine the possibility of using I5 as both a neat emitter and a host. The device structure with the best performance is detailed in FIGS. 39, 40, and 41. Device employing I5 as a host for –aD has moderate EQE and luminous efficacy at low current density (FIG. 39). Slightly higher values for EQE and luminous efficacy are obtained with I5 as a neat fluorescent emitter (FIG. 40).

TABLE 10

Electrochemical properties of phenanthro[9,10-d]imidazoles

| | $E_{ox}$ (V)[a] | $E_{red}$ (V)[a] | HOMO[b] | LUMO[b] |
|---|---|---|---|---|
| I1 | +0.86 | −2.61 | −5.81 | −1.70 |
| I2 | +0.87 | −2.44 | −5.82 | −1.89 |
| I3 | +0.90 | −2.44 | −5.86 | −1.89 |
| I4 | +0.91 | −2.32 | −5.87 | −2.03 |
| I5 | +0.91 | −2.35 | −5.87 | −2.00 |
| I6 | +0.96 | −2.36 | −5.94 | −2.00 |

[a]reference to ferrocene
[b]experimental values in eV

TABLE 11

PLQY data of spin coated films of Ir(ppy)$_3$, Ir(bt)$_2$acac, and PQIr in the phenanthro[9,10-d]imidazole hosts

| PLQY | I1 | I2 | I3 | I4 | I5 | I6 |
|---|---|---|---|---|---|---|
| 10 wt % Ir(ppy)$_3$ | 65 | 49 | 56 | 39 | 30 | 36 |
| 10 wt % Ir(bt)$_2$acac | 80 | 66 | 84 | 83 | 80 | 78 |
| 10 wt % PQIr | 70 | 69 | 67 | 64 | 69 | 66 |
| Neat Host | 80 | — | — | 55 | 81 | 83 |

Figure 41:
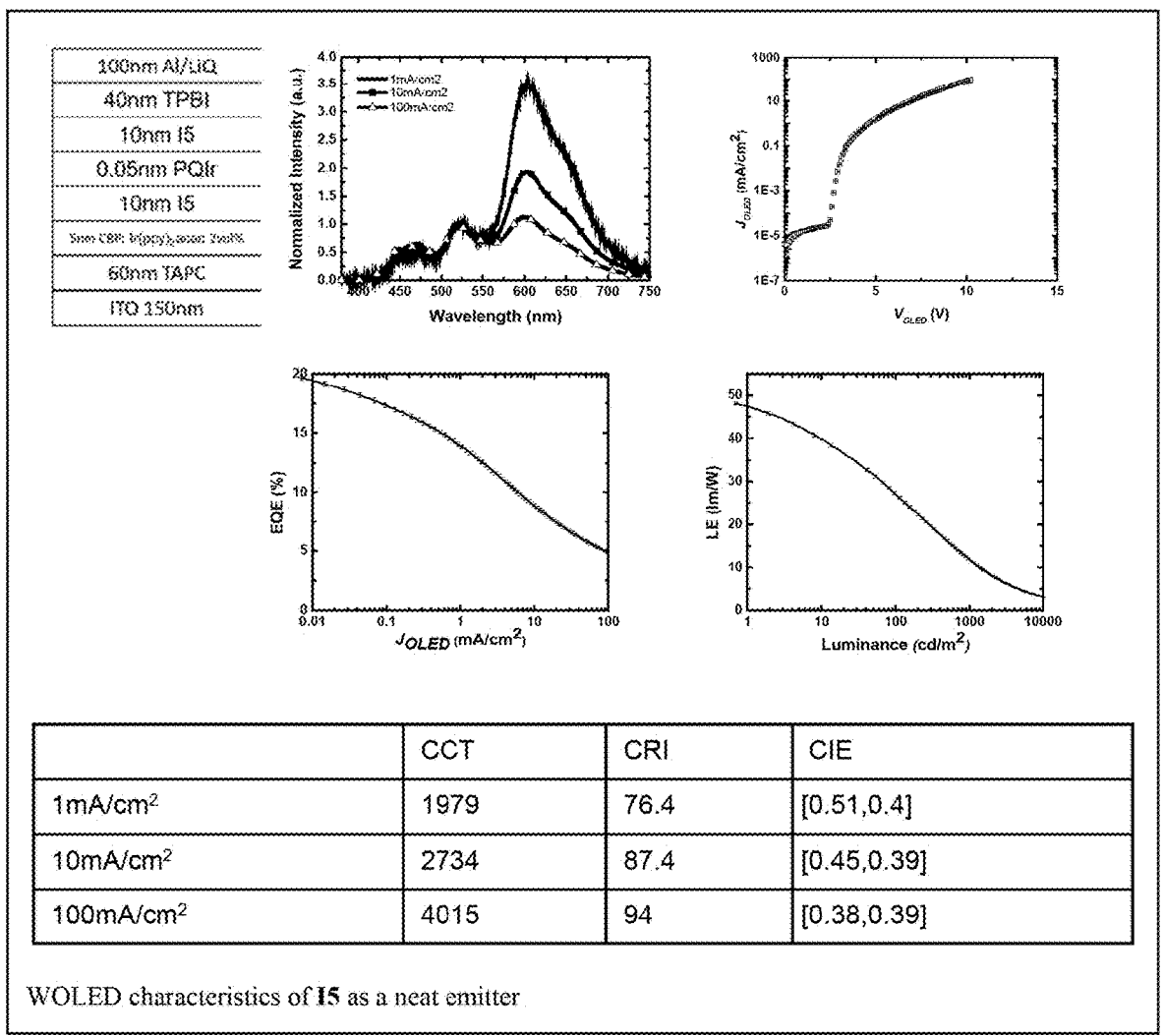
FIG. 41 shows WOLED characteristics of I5 as a neat emitter according to embodiments disclosed herein.
Figure 42:
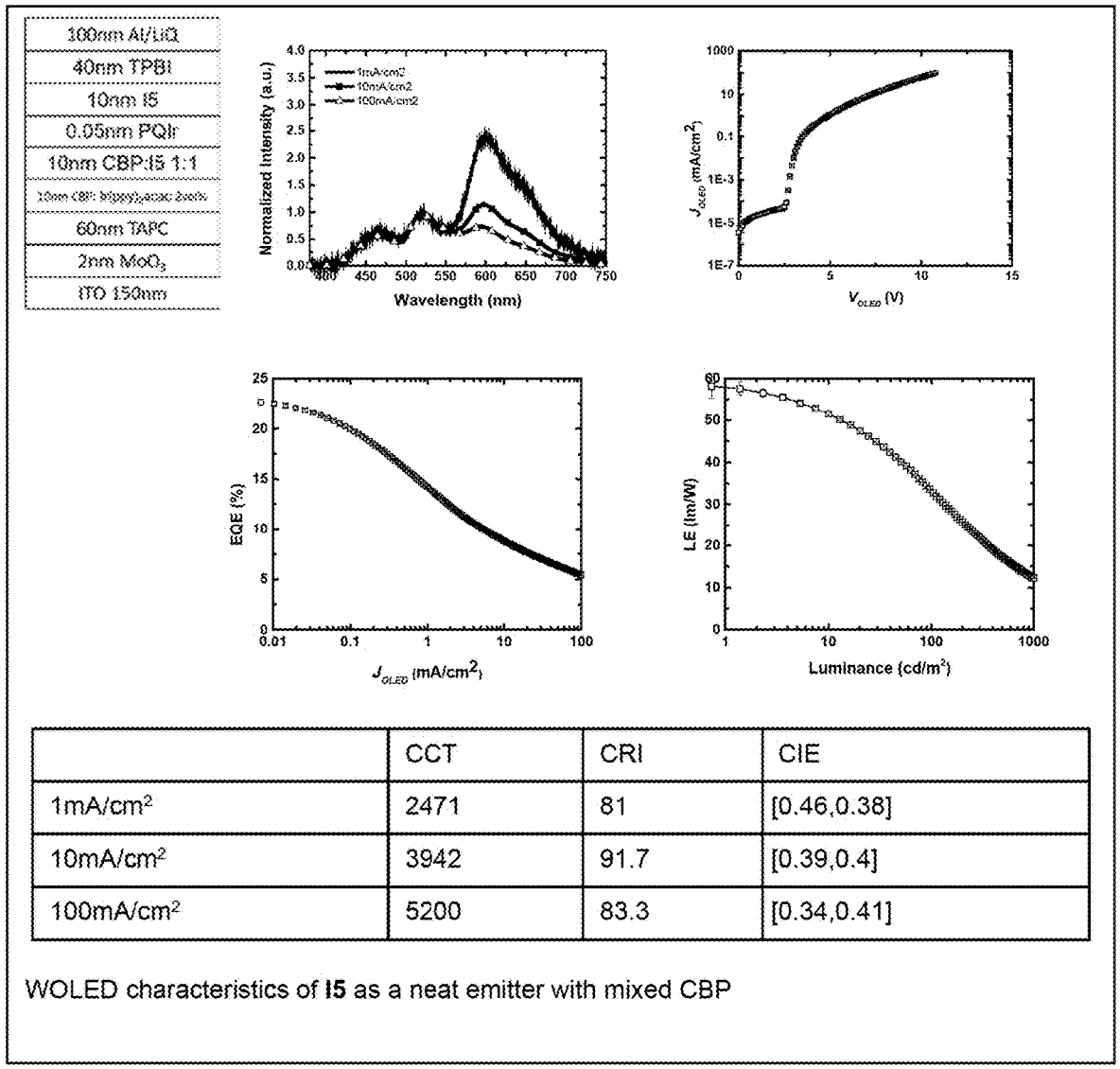
FIG. 42 shows WOLED characteristics of I5 as a neat emitter with mixed CBP according to embodiments disclosed herein.

Compared to the device in FIG. 39, the device in FIG. 40 has well balanced spectrum with CIE coordinates of (0.39, 0.41) and color rendering index of 90 at 10 mA/cm$^2$. Transport layer thicknesses have been adjusted for optimized outcoupling in FIG. 40. Higher luminous efficacy and EQE at low current density are obtained with TPBi as an electron transport layer (FIG. 41). When CBP is mixed with I5 in a 1:1 ratio, EQE and power efficiency is enhanced to 22.5% and 57.81 m/W, respectively as can be seen in FIG. 42. All devices currently suffer from drastic efficiency roll-off at high currents. The efficiency roll-off must be improved for this structure to have any practical value. The luminous power efficacy drops to 17.31 m/W at a forward viewing luminance of 500 nits and further decreases to 12.21 m/W at 1000 nits. Currently, the device in FIG. 42 has a well-balanced white spectrum at a current density of 10 mA/cm2 with CIE coordinates of (0.39,0.4) and color rendering index of 91.7.

Based on these data, a hybrid emissive layer may be constructed following the general parameters that have been found for suitable host and dopant combinations. For example, the data in Tables 9-11 above suggest that I1, I4, I5, and I6 may be suitable fluorescent dopants for use with combinations of hosts and phosphorescent dopants as disclosed herein. These combinations of materials may provide the desirable energy state transitions and performances disclosed herein and referenced previously for early hybrid layers, but without the drawbacks of prior work as disclosed herein.

Generalizing the results of the studies disclosed herein, it has been determined that a hybrid emissive layer may be structured and fabricated such that it includes three materials 1, 2, 3, having the following energy level relationships for the first singlet and triplet states S1, T1, respectively:

$T1_2 \geq T1_1$; $S1_2 \leq S1_1$; and $T1_3 < T1_1$.

In an embodiment, these materials may correspond to the host material, the fluorescent dopant, and the phosphorescent dopant, respectively. That is, in a hybrid emissive layer comprising a host material H, fluorescent dopant F, and phosphorescent dopant P, the singlet and triplet state energy levels may be:

$T1_F \geq T1_H$; $S1_F \leq S1_H$; and $T1_P < T1_H$.

Where $T1_H$ is the first triplet energy level of the host, $T1_F$ is the first triplet energy level of the fluorescent dopant, $S1_F$ is the first singlet energy level of the fluorescent dopant, and $T1_P$ is the first triplet energy level of the phosphorescent dopant. Examples of suitable energy levels may be seen, for example, by comparing FIG. 9B and FIG. 35, which shows energy levels for I5 as disclosed herein. The single and triplet energy levels of the fluorescent dopant, for example as shown by the dashed line and solid line 920, respectively, in FIG. 9B are nested between the singlet and triplet energy levels of the host, in this example I5, given by the solution and solid lines in FIG. 35. As shown by the data disclosed herein, this arrangement can provide efficient WOLED arrangements with enhanced lifetime and operation relative to earlier hybrid emissive layer configurations, which did not require or exhibit the same energy level arrangements. Arrangements as disclosed herein do not lead to, and may prevent, triplet enemy trapping the fluorescent dopant. In contrast, prior devices and materials do not provide for this, because the triplet energy level for the fluorescent dopant typically was well below the triplet level of the host. As previously disclosed, compounds I1, I4, I5, and I6 may be suitable for use in a hybrid layer as disclosed herein, though the embodiments disclosed herein are not limited to these particular materials.

In some embodiments, an OLED incorporating a hybrid emissive layer as disclosed herein may the host material may emit only from the first material, i.e., the fluorescent dopant in some embodiments. Furthermore, in some embodiments the first material, which may be a host material, may be, or may include the fluorescent dopant material. That is, the same material may serve as both the host of the emissive layer and as the fluorescent dopant as disclosed herein. In some cases, the OLED may include additional emissive layers, which may include the same material as the host/fluorescent emissive dopant. Such OLEDs still may exhibit all emission from the first material.

In some embodiments, it may be preferable to maintain a minimum separate between energy levels of the materials. For example, it may be preferred for $T1_H$ is at least 0.1 eV greater than $T1_P$ and/or for $T1_F$ to be at least 0.1 eV greater than $T1_H$. Such arrangements are shown and suggested, for example, by Tables 2.1b and 9-11 herein. Alternatively or in addition, it may be desirable for the S1-T1 energy gaps to fall within specific ranges, as disclosed herein. In particular, it may be desirable for the fluorescent dopant and/or the host material to have relatively small S-T energy gaps as previously described. As a specific example, it may be preferred for the $S1_F$-$T1_F$ gap to be 0.05 to 0.8 eV, 0.1 to 0.8 eV, or less than 0.4 eV. In some embodiments, it also may be preferred for individual energy levels to fall within specific ranges or minimums. For example, as shown by Tables 2.1b and 9-11, it may be preferred for $S1_H$ to be at least 3.5 eV, $T1_H$ to be in the range 2.4-2.6 eV, and/or $T1_P$ to be in the range 1.7-2.5 eV.

The use of materials and combinations of materials as disclosed herein may allow for more efficient and consistent devices than may be achieved using prior hybrid emissive layers or conventional device configurations, as shown by the data presented herein such as at FIGS. 38-42 and Tables 9-11.

EXPERIMENTAL

Synthesis techniques for the dopant and host materials disclosed herein are described below. General synthetic scheme for the preparation of phenanthro[9,10-d]imidazoles.

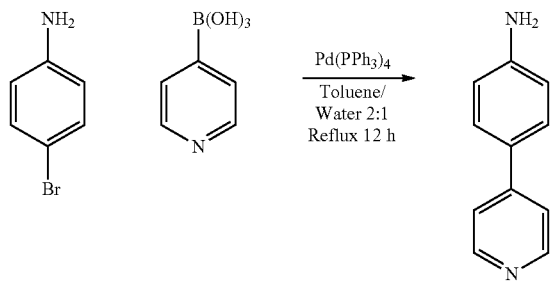

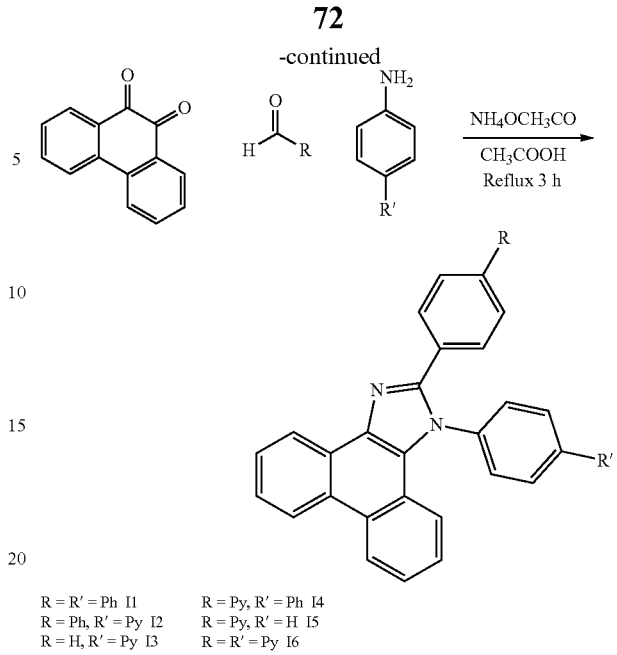

R = R' = Ph I1
R = Ph, R' = Py I2
R = H, R' = Py I3
R = Py, R' = Ph I4
R = Py, R' = H I5
R = R' = Py I6

4-(pyridin-4-yl)aniline: In a 250 ml one-necked round bottomed flask, 4-pyridineboromic acid (14.3 g, 116.2 mmol), 4-bromoaniline (10.0 g, 58.1 mmol), tetrakis(triphenylphosphine)palladium(0) (185 mg, 0.174 mmol), and $Na_2CO_3$ (43.1 g, 406.9 mmol) were added. The flask is purge and backfilled with nitrogen three times. 180 ml of degassed $DMF/H_2O$ (9:2) was canula transferred to the flask and heated to reflux overnight. The reaction mixture was then cooled to room temperature and diluted with DCM. The organic layer was separated, and the solvent removed under reduced pressure. The product was then precipitated from DCM to yield the pale yellow solid (5.30 g, 53%).

1,2-di([1,1'-biphenyl]-4-yl)-1H-phenanthro[9,10-d]imidazole (I1): A mixture of phenanthrene-9,10-dione (2.00 g, 9.61 mmol), [1,1'-biphenyl]-4-amine (1.95 g 11.53 mmol), [1,1'-biphenyl]-4-carbaldehyde (1.75 g, 9.61 mmol) and ammonium acetate (1.48 g, 19.21 mmol) in glacial acetic acid (30 mL) was refluxed for 3 h. The precipitate was filtered and washed with aqueous NaOH deionized water. The residue is dried and sublimed at 250° C. and $1.2 \times 10^{-6}$ torr to give pure product. White solid (4.20 g, 8.04 mmol, 84%).

2-([1,1'-biphenyl]-4-yl)-1-(4-(pyridin-4-yl)phenyl)-1H-phenanthro[9,10-d]imidazole (I2)

A mixture of phenanthrene-9,10-dione (2.20 g, 10.57 mmol), 4-(pyridin-4-yl)aniline (2.16 g 12.68 mmol), [1,1'-biphenyl]-4-carbaldehyde (1.93 g, 10.57 mmol) and ammonium acetate (1.63 g, 21.13 mmol) in glacial acetic acid (70 mL) was refluxed for 3 h. The precipitate was filtered and washed with aqueous NaOH deionized water. The residue is dried and sublimed at 280° C. and $1.2 \times 10^{-6}$ torr to give pure product. White solid (2.13 g, 4.06 mmol, 39%).

2-phenyl-1-(4-(pyridin-4-yl)phenyl)-1H-phenanthro[9,10-d]imidazole (I3): A mixture of phenanthrene-9,10-dione (1.50 g, 7.20 mmol), 4-(pyridin-4-yl)aniline (1.47 g 8.64 mmol), benzaldehyde (0.77 g, 7.20 mmol) and ammonium acetate (1.11 g, 14.41 mmol) in glacial acetic acid (50 mL) was refluxed for 3 h. The precipitate was filtered and washed with aqueous NaOH deionized water. The residue is dried and sublimed at 270° C. and 1.2×10$^{-6}$ torr to give pure product. White solid (1.18 g, 2.64 mmol, 37%).

1-([1,1'-biphenyl]-4-yl)-2-(4-(pyridin-4-yl)phenyl)-1H-phenanthro[9,10-d]imidazole (I4)

A mixture of phenanthrene-9,10-dione (2.00 g, 9.61 mmol), [1,1'-biphenyl]-4-amine (1.95 g 11.53 mmol), 4-(pyridin-4-yl)benzaldehyde (1.76 g, 9.61 mmol) and ammonium acetate (1.48 g, 19.21 mmol) in glacial acetic acid (70 mL) was refluxed for 3 h. The precipitate was filtered and washed with aqueous NaOH deionized water. The residue is dried and sublimed at 270° C. and 1.2×10$^{-6}$ torr to give pure product. White solid (4.20 g, 8.02 mmol, 84%).

1-phenyl-2-(4-(pyridin-4-yl)phenyl)-1H-phenanthro[9,10-d]imidazole (I5): A mixture of phenanthrene-9,10-dione (2.00 g, 9.61 mmol), aniline (1.07 g 11.53 mmol), 4-(pyridin-4-yl)benzaldehyde (1.76 g, 9.61 mmol) and ammonium acetate (1.48 g, 19.21 mmol) in glacial acetic acid (70 mL) was refluxed for 3 h. The precipitate was filtered and washed with aqueous NaOH deionized water. The residue is dried and sublimed at 270° C. and 1.2×10$^{-6}$ torr to give pure product. White solid (3.65 g, 8.15 mmol, 85%).

1,2-bis(4-(pyridin-4-yl)phenyl)-1H-phenanthro[9,10-d]imidazole (I6): A mixture of phenanthrene-9,10-dione (2.50 g, 12.01 mmol), 4-(pyridin-4-yl)aniline (2.45 g 14.41 mmol), 4-(pyridin-4-yl)benzaldehyde (2.20 g, 12.01 mmol) and ammonium acetate (1.85 g, 24.01 mmol) in glacial acetic acid (80 mL) was refluxed for 3 h. The precipitate was filtered and washed with aqueous NaOH deionized water. The residue is dried and sublimed at 270° C. and 1.2×10$^{-6}$ torr to give pure product. White solid (4.30 g, 8.20 mmol, 68%).

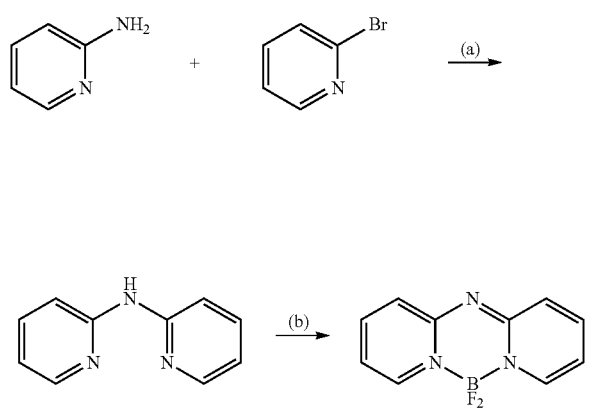

Reaction scheme to make aD

Synthesis of aD: (a) 2,2'-dipyridylamine (aD ligand): A reported procedure was followed (cite); bis(2-diphenylphosphinophenyl) ether(498.99 mg, 926.51 μmol), 2-bromopyridine(3.66, 23.16 mmol), 2-aminopyridine (2.18 g, 23.16 mmol) and t-BuONa (3.12 g, 32.43 mmol) were purged with nitrogen gas in a re-sealable shlenk flask where a degassed dry toluene is cannula transferred. Pd(OAc)$_2$ catalyst was added to the air free flask and refluxed in a 110° C. oil bath for 24 hours. The reaction mixture is cooled to room temperature and diluted with THF and ethyl ether. The solid precipitate was filtered, concentrated, and purified via silica gel column chromatography (2% MeOH/CH$_2$Cl$_2$). An alternative route is to purchase the commercially available 2,2'-dipyridylamine.

(b) azaDIPYR (aD): All reagents were purchased from Sigma Aldrich and used without purification. Anhydrous 1,2 dichloroethane was purchased from EMD Millipore. A solution of the 2,2'-dipyridylamine ligand (300 mg, 1.75 mmol) in dry 1,2-dichloroethane was prepared in an N2-purged schlenk flask equipped with a magnetic stir bar and fitted with a reflux condenser. The flask was submerged in a preheated oil bath and brought to reflux, at which time 2.0 eq. boron trifluoride diethyl etherate (497.40 mg, 3.50 mmol) were added dropwise. The solution was stirred for 2 hours at reflux, then cooled to room temperature and treated with 5 eq. N,N diisopropylethylamine (1.53 mL, 8.70 mmol). The solution was washed with water and the aqueous layer was separated and extracted three times with DCM. The total organic extractions were filtered, and reduced concentrated by rotary evaporation. The products were purified by silica gel flash chromatography with the eluent 50% dichloromethane in hexanes.

(a) 2,2'-diquinolylamine (α-aD ligand): A reported procedure was followed (cite); bis(2-diphenylphosphinophenyl) ether(395.03 mg, 733.48 μmol), 2-bromoquinoline(3.00 g, 18.34 mmol), 2-aminoquinoline (2.78 g, 19.25 mmol) and t-BuONa (2.47 g, 25.67 mmol) were purged with nitrogen gas in a re-sealable shlenk flask where degassed dry toluene is cannula transferred. Pd(OAc)$_2$ (164.67, 733.48 μmol) catalyst was added to the air free flask and refluxed in a 110° C. oil bath for 24 hours. The reaction mixture is cooled to room temperature and diluted with THF and ethyl ether. The solid precipitate was filtered, concentrated, and purified via silica gel column chromatography (2% MeOH/CH$_2$Cl$_2$). A white solid is isolated upon purification (40-80% yield).

(b) n-azaDIPYR (n-aD): All reagents were purchased from Sigma Aldrich and used without purification. Anhydrous 1,2 dichloroethane was purchased from EMD Millipore. A 15 mM solution of 2,2'-diquinolylamine in dry 1,2-dichloroethane was prepared in an N2-purged schlenk flask equipped with a magnetic stir bar and fitted with a reflux condenser. The flask was submerged in a preheated oil bath and brought to reflux, at which time 2.0 eq. boron trifluoride diethyl etherate were added dropwise. The solution was stirred for 2 hours at reflux, then cooled to room temperature and treated with 5 eq. N,N diisopropylethylamine, causing the precipitate to dissolve. The solution was washed with water and the aqueous layer was separated and extracted three times with dichloromethane. The organic layers were combined, dried over sodium sulfate, filtered, and reduced concentrated by rotary evaporation. The products were purified by silica gel flash chromatography with the eluent 80% 2% MeOH/CH$_2$Cl$_2$ solvent mixture in hexanes. For further purification, the material was sublimed. 1H).

Synthetic scheme to make substituted α-aID compound.

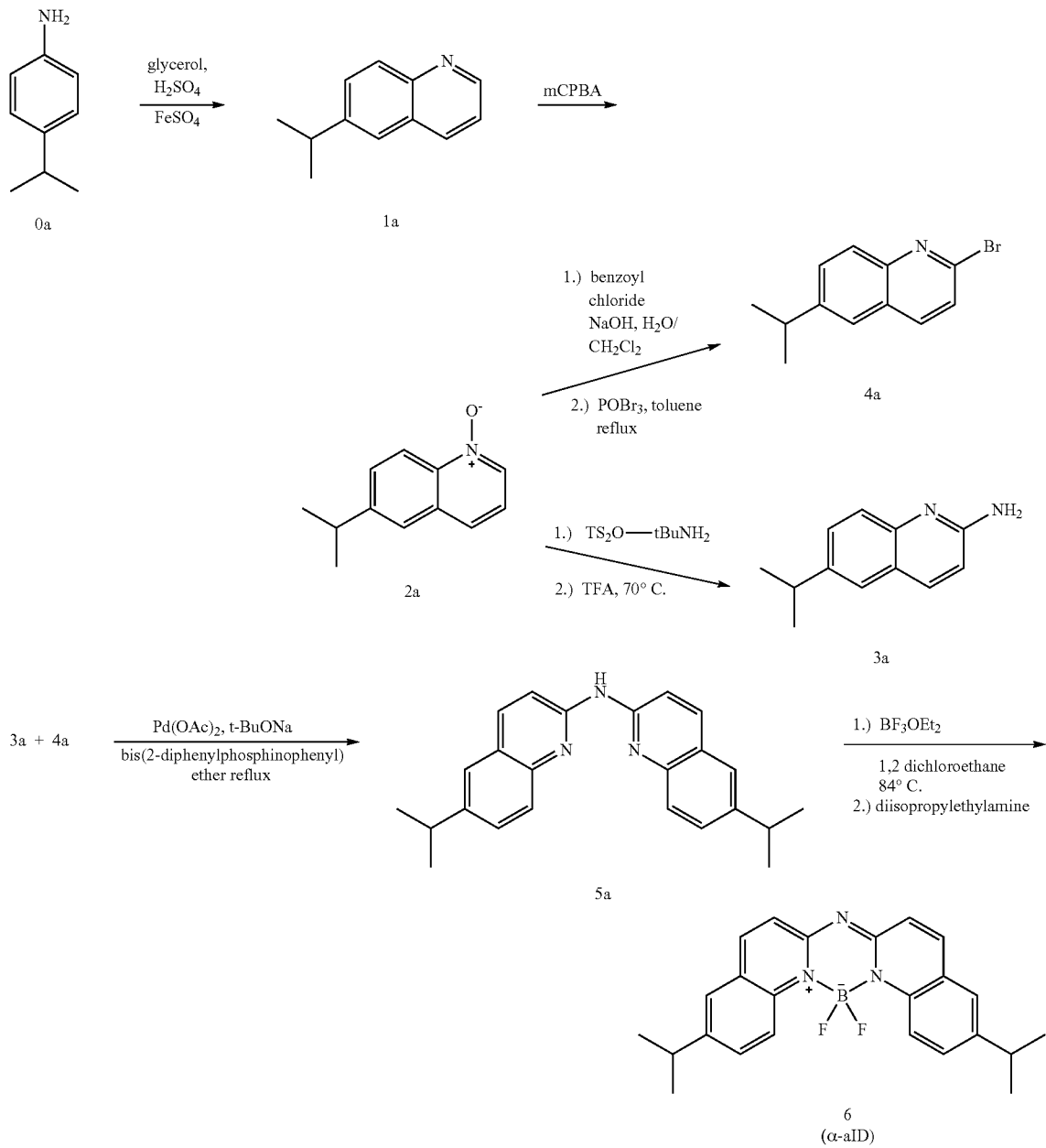

6-isopropylquinoline (1a). 4-isopropylaniline (20 g, 0.147 mole), nitrobenzene (9.86 ml, 0.096 mole), Glycerol (55.85 g, 0.606 mole), and $FeSO_4 \cdot 7H_2O$ (5.14 g, 18.49 mole) were added to a three-neck round bottom flask. While the flask was kept in an ice bath, $H_2SO_4$ (25 ml, 0.473 mole) was added slowly to the reaction mixture. After the addition was completed, the ice bath was removed followed by refluxing the mixture for 20 h under inert conditions. After cooling to room temperature, the pH of the solution was adjusted to pH 7 with 50% NaOH aq. Then, solution was extracted with diethyl ether. After the extraction, $MgSO_4$ was used as a drying agent. Filtration followed by evaporation to give a brown liquid. The product was isolated by reduced pressure distillation to yield the desired light-yellow liquid (yield 20%).

6-isopropylquinoline-1-oxide (2a). Compound (1a) (10.2 g, 0.059 mole) was dissolved in one-neck round bottom flask with $CH_2Cl_2$ (50 ml). M-chloroperoxybenzoic acid (m-CPBA) (12.33 g, 0.071 mole) was added slowly the stirred solution at room temperature. The reaction was stirred overnight. Next, saturated $NaHCO_3$ aq solution was added to stirring solution until no $CO_2$ gas bubbles were observed anymore. Then, pH was adjusted to 10 with NaOH aq solution and extracted with $CH_2Cl_2$ 50 ml three times. The solution was dried over $MgSO_4$. The solvent was removed under reduced pressure. The crude product was then purified by silica gel column chromatography (2% Methanol/$CH_2Cl_2$). White pale-yellow solid was afforded at 60% yield.

6-isopropylquinoline-2-amine (3a). To a round bottom flask, compound (2a) (2.55 g, 0.013 mole) and 30 ml of trifluorotoluene (7.16 ml, 0.068 mole) were mixed in 20 ml of chloroform. After compound (2a) was dissolved, the mixture was cooled to 0° C. with an ice bath. T-butylamine (7.16 ml, 0.068 mole) was added slowly followed by Ts$_2$O (8.89 g, 0.027 mole). The reaction was left to stir for two hours. If the reaction were not completed, portions of t-butylamine (0.6 equiv. to 4.0 equiv.) and Ts$_2$O (0.3 equiv. to 2.3 equiv.) would be added until the reaction is completed. The reaction was then treated with 25 ml TFA at 70° C. for overnight under inert atmosphere. After that, most of the solvents were removed under reduced pressure and them the concentrated oil residue was diluted with CH$_2$Cl$_2$ and quenched with 50% of aq solution of NaOH to pH 10. The solution was extracted with CH$_2$Cl$_2$ three times, dried over MgSO$_4$, and removed under reduced pressure. The crude product was then purified using a silica gel column chromatography (2% Methanol/CH$_2$Cl$_2$). The desired white solid was obtained at 70%.

2-bromo-6-isopropylquinoline (4a). To a round bottom flask cooled to 5° C. with an ice bath, benzoyl chloride (2.33 ml, 0.02 mol) was added slowly to the vigorously stirred mixture of compound (2a) (2.5 g, 0.0133 mol), sodium hydroxide (1 g, 0.025 mol) in water (12 ml) and CH$_2$Cl$_2$ (10 ml). After the addition is complete, the reaction mixture was left to stir for few hours. Then, the mixture was extracted from CH$_2$Cl$_2$. The combined organic layer was dried over MgSO$_4$. Solvent was removed under reduced pressure to obtain a white solid product. After that, the solid was mixed with POBr$_3$ (2.2 g, 0.007 mol) in dry toluene (20 ml) under inert atmosphere, heated to reflux overnight. After cooling to room temperature, the mixture was poured on ice, washed with saturated NaHCO$_3$ and extracted with CH$_2$Cl$_2$ several times. The solvent was removed under reduced pressure. The crude product was then purified using a silica gel column chromatography (50%) Hexane/CH$_2$Cl$_2$). The desired white solid was obtained at 40%.

Bis(6-isopropylquinoline-2-yl)amine (5a). Compound (3a) (2.23 g, 0.012 mol) and compound (4a) (3 g, 0.012 mol) were mixed with bis(2-diphenylphosphinophenyl)ether (0.246 g, 4% mmol), t-BuONa (1.54 g, 0.016 mol), and Pd(OAc)$_2$ (0.1 g, 4% mmol) in a three-neck round bottom flask. The flask was subjected to three cycles of evacuation-backfilling with N$_2$. Dry toluene purged with N$_2$ was transferred to the reaction mixture using a cannula. The reaction was refluxed for 48 h at 110° C. under inert atmosphere. After that, the mixture was cooled to room temperature, extracted from CH$_2$Cl$_2$, dried over MgSO$_4$, and solvent removed under reduced pressure. The crude product was then purified using a silica gel column chromatography (2% Methanol/CH$_2$Cl$_2$). The desired white solid was obtained at 50%.

(α-aID). Compound (5a) (1 g, 0.0028 mol) was dissolved in dry toluene under N$_2$ in a three-neck round bottom flask. DIEA (1.47 ml, 0.008 mol) was slowly injected to the solution. After 30 min stirring, BF$_3$OEt$_2$ (1.39 ml, 0.0011 mol) was slowly added dropwise to the solution. The reaction was then left to reflux overnight. After cooling to room temperature, saturated solution of NaHCO$_3$ aq was added to the reaction mixture, followed by extraction from CH$_2$Cl$_2$. The combined organic layers were dried over MgSO$_4$, and solvent removed under reduced pressure. The crude product was purified by silica gel chromatography (50% Hexane/Ethyl acetate) to afford a yellow solid. The desired product was further sublimed at 190° C. under 1.2×10$^{-6}$ torr.

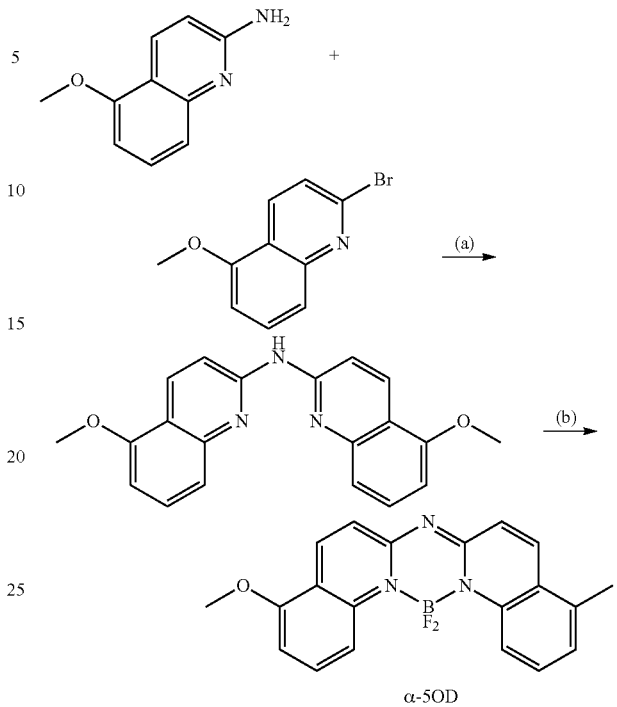

Synthetic scheme to make substituted α-5OD compound.

2,2'-di-5-methoxyquinolylamine (α-5OD ligand): bis(2-diphenylphosphinophenyl) ether (43 mg, 80 μmol), 2-bromo-5-methoxyquinoline (500 mg, 2.1 mmol), 2-amino-5-methoxyquinoline (365 mg, 2.1 mmol) and t-BuONa (269 mg, 2.8 mmol), and Pd(OAc)$_2$ (17.96 mg, 80 μmol) catalyst were added to a three-neck round bottom flask. The air free flask and refluxed in a 110° C. oil bath for 48 hours. The flask was subjected to three cycles of evacuation-backfilling with N$_2$. Dry toluene purged with N$_2$ was transferred to the reaction mixture using a cannula. The reaction was refluxed for 48 h at 110° C. under inert atmosphere. After that, the mixture was cooled to room temperature, extracted from CH$_2$Cl$_2$, dried over MgSO$_4$, and solvent removed under reduced pressure. The crude product was then purified using a silica gel column chromatography (2% Methanol/CH$_2$Cl$_2$).

(α-5OD). In a three-neck round bottom flask, the ligand, 2,2'-di-5-methoxyquinolylamine (α-5OD ligand) (500 mg, 1.51 mmol) was dissolved in dry toluene under N$_2$. DIEA (0.79 ml, 4.53 mmol) was slowly injected to the solution. After 30 min of stirring, BF$_3$OEt$_2$ (0.745 ml, 6.04 mmol) was slowly added dropwise to the solution. The reaction was then left to reflux overnight. After cooling to room temperature, saturated solution of NaHCO$_3$ aq was added to the reaction mixture, followed by extraction from CH$_2$Cl$_2$. The combined organic layers were dried over MgSO$_4$, and solvent removed under reduced pressure. The crude product was purified by silica gel chromatography (2% Methanol/CH$_2$Cl$_2$) to afford a yellow solid. The desired product was further sublimed at 200° C. under 1.2×10$^{-6}$ torr.

5-methoxy-N-(quinolin-2-yl)quinolin-2-amine (αα-OD ligand): bis(2-diphenylphosphinophenyl) ether (17.23 mg, 32 μmol), 2-bromo-5-methoxyquinoline (200 mg, 0.84 mmol), 2-aminoquinoline (121 mg, 0.84 mmol) and t-BuONa (107.64 mg, 1.12 mmol), and Pd(OAc)$_2$ (7.18 mg, 32 μmol) catalyst were added to a three-neck round bottom flask. The air free flask and refluxed in a 110° C. oil bath for 48 hours. The flask was subjected to three cycles of evacuation-backfilling with $N_2$. Dry toluene purged with $N_2$ was transferred to the reaction mixture using a cannula. The reaction was refluxed for 48 h at 110° C. under inert atmosphere. After that, the mixture was cooled to room temperature, extracted from $CH_2Cl_2$, dried over $MgSO_4$, and solvent removed under reduced pressure. The crude product was then purified using a silica gel column chromatography (2% Methanol/$CH_2Cl_2$).

(αα-OD). In a three-neck round bottom flask, the ligand, 5-methoxy-N-(quinolin-2-yl)quinolin-2-amine (α-5OD ligand) (500 mg, 1.51 mmol) was dissolved in dry toluene under $N_2$. DIEA (0.79 ml, 4.53 mmol) was slowly injected to the solution. After 30 min of stirring, $BF_3OEt_2$ (0.745 ml, 6.04 mmol) was slowly added dropwise to the solution. The reaction was then left to reflux overnight. After cooling to room temperature, saturated solution of $NaHCO_3$ aq was added to the reaction mixture, followed by extraction from $CH_2Cl_2$. The combined organic layers were dried over $MgSO_4$, and solvent removed under reduced pressure. The crude product was purified by silica gel chromatography (2% Methanol/$CH_2Cl_2$) to afford a yellow solid. The desired product was further sublimed at 200° C. under $1.2 \times 10^{-6}$ torr.

N-(isoquinolin-1-yl)-5-methoxyquinolin-2-amine (α☐-OD ligand): bis(2-diphenylphosphinophenyl) ether (23.56 mg, 43.74 μmol), 2-amino-5-methoxyquinoline (200 mg, 1.15 mmol), 1-chloroisoquinoline (187.83 mg, 1.15 mmol) and t-BuONa (147.12 mg, 1.53 mmol), and $Pd(OAc)_2$ (9.82 mg, 43.74 μmol) catalyst were added to a three-neck round bottom flask. The air free flask and refluxed in a 110° C. oil bath for 48 hours. The flask was subjected to three cycles of evacuation-backfilling with $N_2$. Dry toluene purged with $N_2$ was transferred to the reaction mixture using a cannula. The reaction was refluxed for 48 h at 110° C. under inert atmosphere. After that, the mixture was cooled to room temperature, extracted from $CH_2Cl_2$, dried over $MgSO_4$, and solvent removed under reduced pressure. The crude product was then purified using a silica gel column chromatography (2% Methanol/$CH_2Cl_2$).

(α☐-OD). In a three-neck round bottom flask, the ligand, N-(isoquinolin-1-yl)-5-methoxyquinolin-2-amine (α☐-OD ligand) (300 mg, 1.0 mmol) was dissolved in dry toluene under $N_2$. DIEA (0.52 ml, 2.99 mmol) was slowly injected to the solution. After 30 min of stirring, $BF_3OEt_2$ (0.491 ml, 3.98 mmol) was slowly added dropwise to the solution. The reaction was then left to reflux overnight. After cooling to room temperature, saturated solution of $NaHCO_3$ aq was added to the reaction mixture, followed by extraction from $CH_2Cl_2$. The combined organic layers were dried over $MgSO_4$, and solvent removed under reduced pressure. The crude product was purified by silica gel chromatography (2% Methanol/$CH_2Cl_2$) to afford a yellow solid. The desired product was further sublimed at 200° C. under $1.2 \times 10^{-6}$ torr.

Reaction scheme to make tolyl substituted azaDIPYR from the boron atom (aDBT₂)

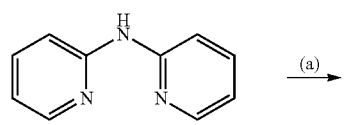

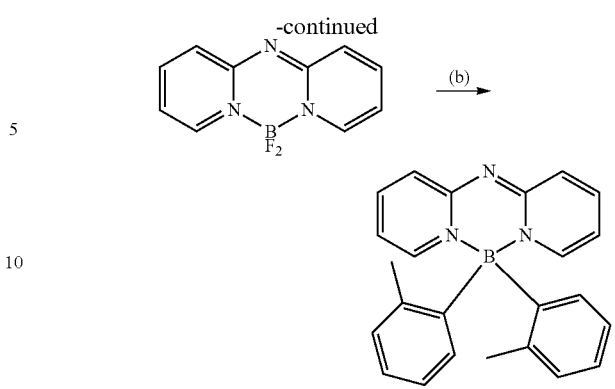

(a) azaDIPYR (aD): All reagents were purchased from Sigma Aldrich and used without purification. Anhydrous 1,2 dichloroethane was purchased from EMD Millipore. A solution of the 2,2'-dipyridylamine ligand (300 mg, 1.75 mmol) in dry 1,2-dichloroethane was prepared in an $N_2$-purged schlenk flask equipped with a magnetic stir bar and fitted with a reflux condenser. The flask was submerged in a preheated oil bath and brought to reflux, at which time 2.0 eq. boron trifluoride diethyl etherate (497.40 mg, 3.50 mmol) were added dropwise. The solution was stirred for 2 hours at reflux, then cooled to room temperature and treated with 5 eq. N,N diisopropylethylamine (1.53 mL, 8.70 mmol). The solution was washed with water and the aqueous layer was separated and extracted three times with dichloromethane. The organic layers were combined, dried over sodium sulfate, filtered, and reduced concentrated by rotary evaporation. The products were purified by silica gel flash chromatography with the eluent 50% dichloromethane in hexanes. (b) azaDIPYRBT₂ (aDBT₂): A solution of aD (528 mg, 2.27 mmol) in dry toluene or dry THF was purged with nitrogen gas in a sealed round bottom flask equipped with a stir bar. o-Tolylmagnesium bromide (2.0 M, 9.06 mL, 9.06 mmol) was added dropwise at 25° C. and allowed to stir for 12 hours. Additional o-Tolylmagnesium bromide was added and allowed to stir for 3 hours. The reaction was quenched with water and extracted three times with 100 mL of ethylacetate. The extracted organic fraction was dried using sodium sulfate, concentrated using a rotary evaporation. The product was purified by silica gel flash chromatography with the eluent 80% ethylacetate in hexanes.

Reaction scheme to make (aCarD)

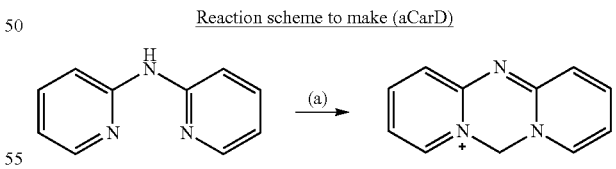

(a) azaDIPYRBPh₂ (aDBPh₂): All reagents were purchased from Sigma Aldrich and used without purification. Anhydrous 1,2 dichloroethane was purchased from EMD Millipore. A solution of the 2,2'-dipyridylamine ligand (800 mg, 4.67 mmol) and diphenylboronic anhydride (1.62 g, 4.67 mmol) in dry 1,2-dichloroethane was prepared in an $N_2$-purged schlenk flask equipped with a magnetic stir bar and fitted with a reflux condenser. The flask was submerged in a preheated oil bath and brought to reflux for 16 hours. The solution was washed with water and the aqueous layer was separated and extracted three times with dichloromethane. The organic layers were combined, dried over sodium sulfate, filtered, and reduced concentrated by rotary evaporation. The product was purified by silica gel flash chromatography with 100% ethylacetate then 100% acetone.

Reaction scheme to make (α-aCarD)

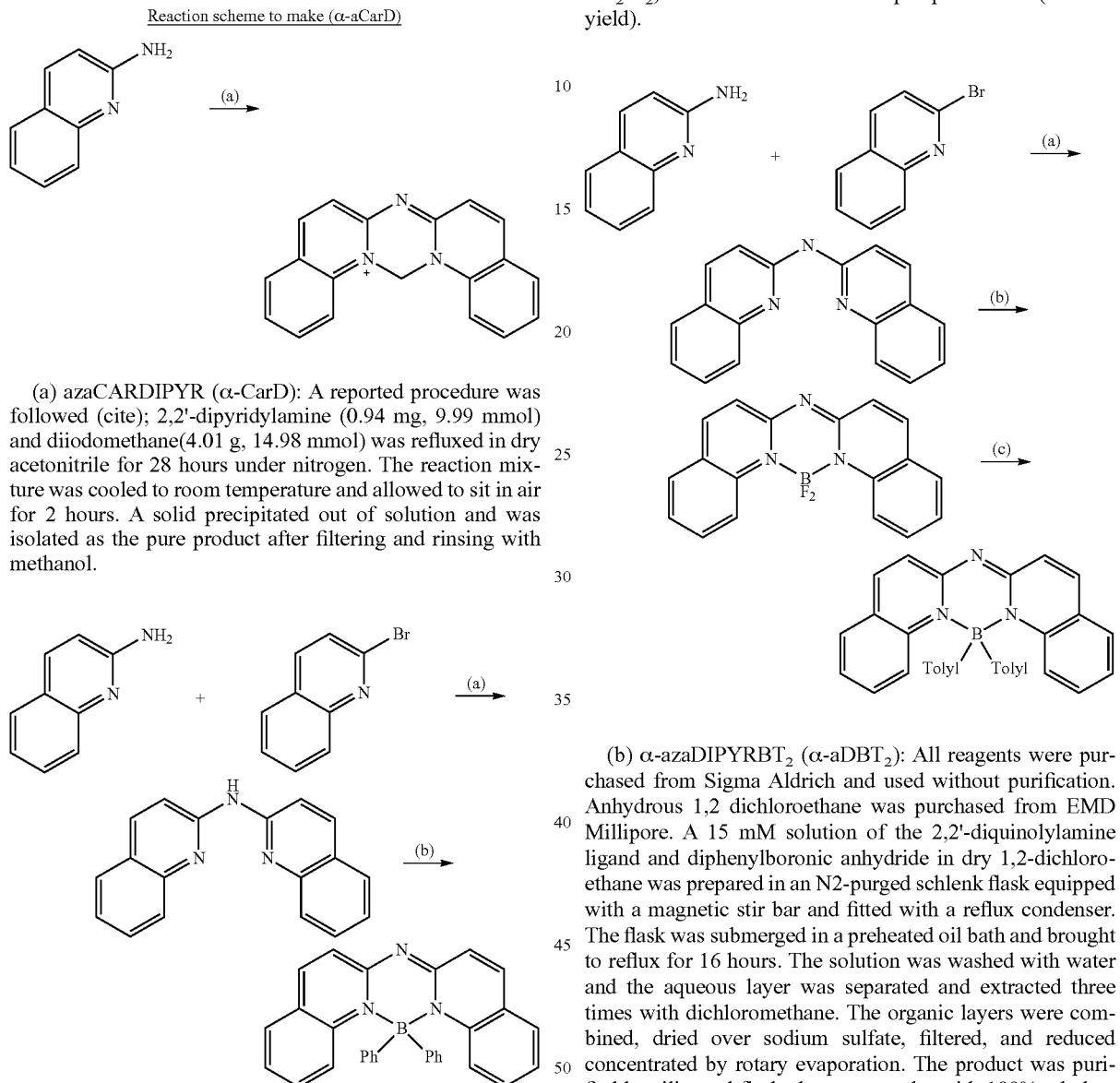

(a) azaCARDIPYR (α-CarD): A reported procedure was followed (cite); 2,2'-dipyridylamine (0.94 mg, 9.99 mmol) and diiodomethane(4.01 g, 14.98 mmol) was refluxed in dry acetonitrile for 28 hours under nitrogen. The reaction mixture was cooled to room temperature and allowed to sit in air for 2 hours. A solid precipitated out of solution and was isolated as the pure product after filtering and rinsing with methanol.

(a) α-azaCARDIPYR (α-aCarD): A reported procedure was followed (cite); 2,2'-diquinolylamine (1.00 g, 6.94) and diiodomethane (2.79, 10.40 mmol) was refluxed in dry acetonitrile for 28 hours under nitrogen. The reaction mixture was cooled to room temperature and allowed to sit in air for 2 hours. A solid precipitated out of solution and was isolated as the pure product after filtering and rinsing with methanol.

(a) 2,2'-diquinolylamine (α-aD ligand): A reported procedure was followed (cite); bis(2-diphenylphosphinophenyl) ether(395.03 mg, 733.48 μmol), 2-bromoquinoline(3.00 g, 18.34 mmol), 2-aminoquinoline (2.78 g, 19.25 mmol) and t-BuONa (2.47 g, 25.67 mmol) were purged with nitrogen gas in a re-sealable shlenk flask where a degassed dry toluene is cannula transferred. Pd(OAc)$_2$ (164.67, 733.48 μmol) catalyst was added to the air free flask and refluxed in a 110° C. oil bath for 24 hours. The reaction mixture is cooled to room temperature and diluted with THF and ethyl ether. The solid precipitate was filtered, concentrated, and purified via silica gel column chromatography (2% MeOH/CH$_2$Cl$_2$). A white solid is isolated upon purification (40-80% yield).

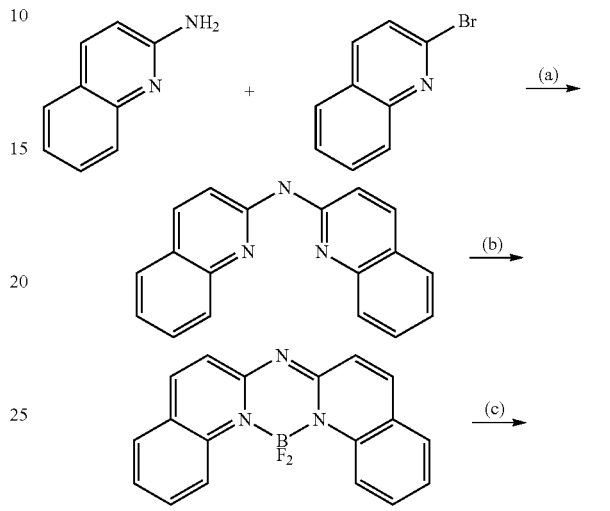

(b) α-azaDIPYRBT$_2$ (α-aDBT$_2$): All reagents were purchased from Sigma Aldrich and used without purification. Anhydrous 1,2 dichloroethane was purchased from EMD Millipore. A 15 mM solution of the 2,2'-diquinolylamine ligand and diphenylboronic anhydride in dry 1,2-dichloroethane was prepared in an N2-purged schlenk flask equipped with a magnetic stir bar and fitted with a reflux condenser. The flask was submerged in a preheated oil bath and brought to reflux for 16 hours. The solution was washed with water and the aqueous layer was separated and extracted three times with dichloromethane. The organic layers were combined, dried over sodium sulfate, filtered, and reduced concentrated by rotary evaporation. The product was purified by silica gel flash chromatography with 100% ethylacetate then 100% acetone.

a) 2,2'-diquinolylamine (α-aD ligand): A reported procedure was followed (cite); bis(2-diphenylphosphinophenyl) ether(395.03 mg, 733.48 μmol), 2-bromoquinoline(3.00 g, 18.34 mmol), 2-aminoquinoline (2.78 g, 19.25 mmol) and t-BuONa (2.47 g, 25.67 mmol) were purged with nitrogen gas in a re-sealable shlenk flask where a degassed dry toluene is cannula transferred. Pd(OAc)$_2$ (164.67, 733.48 μmol) catalyst was added to the air free flask and refluxed in a 110° C. oil bath for 24 hours. The reaction mixture is cooled to room temperature and diluted with THF and ethyl ether. The solid precipitate was filtered, concentrated, and purified via silica gel column chromatography (2% MeOH/CH$_2$Cl$_2$). A white solid is isolated upon purification (40-80% yield).

(b) α-azaDIPYR (α-aD): All reagents were purchased from Sigma Aldrich and used without purification. Anhydrous 1,2 dichloroethane was purchased from EMD Millipore. A 15 mM solution of 2,2'-diquinolylamine in dry 1,2-dichloroethane was prepared in an N2-purged schlenk flask equipped with a magnetic stir bar and fitted with a reflux condenser. The flask was submerged in a preheated oil bath and brought to reflux, at which time 2.0 eq. boron trifluoride diethyl etherate were added dropwise. The solution was stirred for 2 hours at reflux, then cooled to room temperature and treated with 5 eq. N,N diisopropylethylamine, causing the precipitate to dissolve. The solution was washed with water and the aqueous layer was separated and extracted three times with dichloromethane. The organic layers were combined, dried over sodium sulfate, filtered, and reduced concentrated by rotary evaporation. The products were purified by silica gel flash chromatography with the eluent 2% MeOH/CH$_2$Cl$_2$ solvent mixture in hexanes.

(c) α-azaDIPYRBT$_2$ (α-aDBT$_2$): A solution of α-aD (528 mg, 1.59 mmol) in dry toluene or dry THF was purged with nitrogen gas in a sealed round bottom flask equipped with a stir bar. o-Tolylmagnesium bromide (2.0M, 3.18 mL, 6.36 mmol) was added dropwise at 25° C. and allowed to stir for 12 hours. Additional o-Tolylmagnesium bromide was added and allowed to stir for 3 hours. The reaction was quenched with water and extracted three times with 100 mL of ethylacetate. The extracted organic fraction was dried using sodium sulfate, concentrated using a rotary evaporation. The product was purified by silica gel flash chromatography with the eluent 70% ethylacetate in hexanes.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. An organic light emitting diode (OLED) comprising:
   an anode;
   a cathode; and
   a hybrid first emissive layer disposed between the anode and the cathode, wherein the hybrid emissive layer comprises:
      a first material having a triplet state energy level T1$_H$ and a singlet state energy level S1$_H$;
      a second material having a triplet state energy level T1$_F$ and a singlet state energy level S1$_F$; and
      a third material having a triplet state energy level T1$_P$ and a single state energy level S1$_P$;
   wherein:

$T1_F \geq T1_H$; $S1_F \leq S1_H$ and $T1_P < T1_H$;

wherein the first material is a compound of Formula I:

Formula I

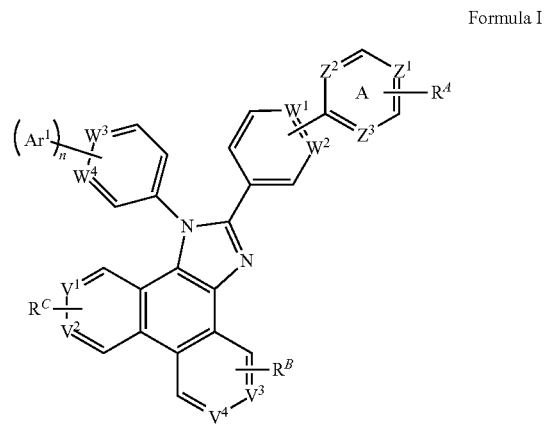

wherein
   W$^1$ and W$^2$ are independently selected from C, CH, or N; wherein one of W$^1$ or W$^2$ is C that is substituted with Ring A;
   W$^3$ and W$^4$ are independently selected from C, CR$^W$, or N, and n is 0 or 1, wherein if n is 1 then one of W$^3$ or W$^4$ is C that is substituted with AO;
   Z$^1$, Z$^2$, and Z$^3$ are independently selected from CR$^A$ or N, and at least one of Z$^1$, Z$^2$, or Z$^3$ is N;
   V$^1$ and V$^2$ are independently selected from CR$^C$ or N;
   V$^3$ and V$^4$ are independently selected from CR$^B$ or N; and
   Ar$^1$ is selected from an optionally substituted aryl, or an optionally substituted heteroaryl;
   R$^W$ is independently selected from the group consisting of hydrogen, deuterium, alkyl, cycloalkyl, alkoxy, aryloxy, amino, silyl, heterocyclic, aryl, heteroaryl, nitrile, isonitrile, and combinations thereof;
   each R$^A$ is independently hydrogen or a substituent selected from the group consisting of deuterium, alkyl, cycloalkyl, alkoxy, aryloxy, amino, silyl, heterocyclic, aryl, heteroaryl, nitrile, isonitrile, and combinations thereof; or optionally, two adjacent R$^A$ join to form a fused aromatic ring, which is optionally substituted;
   R$^B$ and R$^C$ independently represent from mono substitution to the maximum possible number of substitution, or no substitution; and
   each R$^B$ and R$^C$ is independently hydrogen or a substituent selected from the group consisting of deuterium, alkyl, cycloalkyl, alkoxy, aryloxy, amino, silyl, heterocyclic, aryl, heteroaryl, nitrile, isonitrile, and combinations thereof, or optionally, two adjacent R$^B$ or R$^C$ join to form a fused aromatic ring, which is optionally substituted.

2. The OLED of claim 1, wherein the second material is a fluorescent emissive material.

3. The OLED of claim 1, wherein the third material is a phosphorescent emissive material.

4. The OLED of claim 1, wherein T1$_H$ is at least 0.1 eV greater than T1$_P$.

5. The OLED of claim 1, wherein T1$_F$ is at least 0.1 eV greater than T1$_H$.

6. The OLED of claim 1, wherein all emission by the OLED is from the first material.

7. The OLED of claim 6, further comprising a second emissive layer, the second emissive layer comprising the first material.

8. The OLED of claim 6 wherein the first and second materials are the same material.

9. The OLED of claim 1, wherein the energy gap between $S1_F$ and $T1_F$ is 0.05 eV to 0.8 eV.

10. The OLED of claim 1, wherein $T1_H$ is 2.4 eV to 2.6 eV.

11. The OLED of claim 1, wherein $S1_H$ is at least 3.5 eV.

12. The OLED of claim 1, wherein $T1_P$ is 1.7 to 2.5 eV.

13. The OLED of claim 2, wherein the fluorescent emissive material has a fluorescence efficiency of at least 60%.

14. The OLED of claim 1, wherein the second material is selected from compounds A and B:

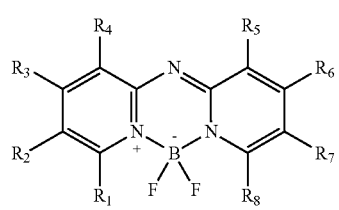

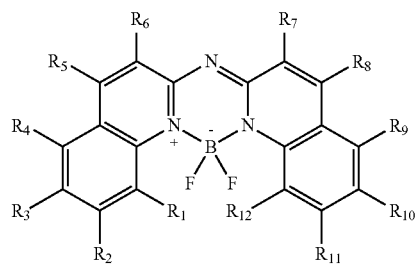

wherein each $R_1$ to $R_{12}$ is independently hydrogen or a substituent selected from the group consisting of deuterium, halogen, alkyl, cycloalkyl, heteroalkyl, heterocycloalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

15. The OLED of claim 1, wherein the second material emits light with a peak wavelength of 400 nm to 510 nm.

16. The OLED of claim 1, wherein the compound is selected from the group consisting of

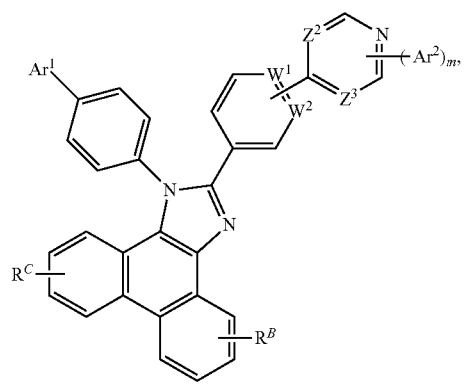

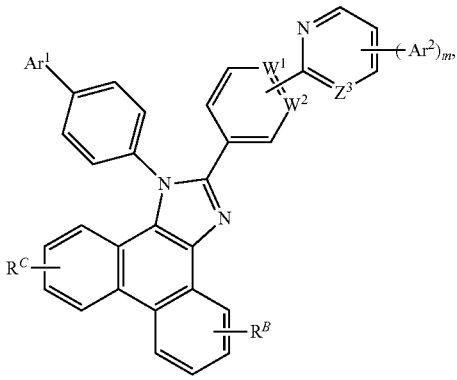

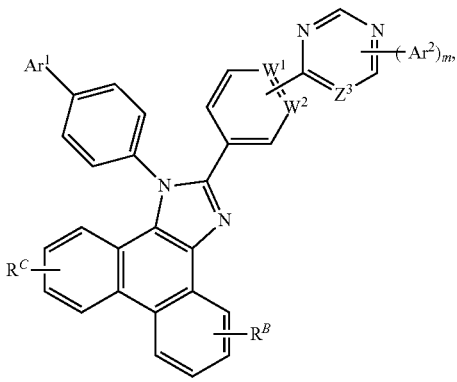

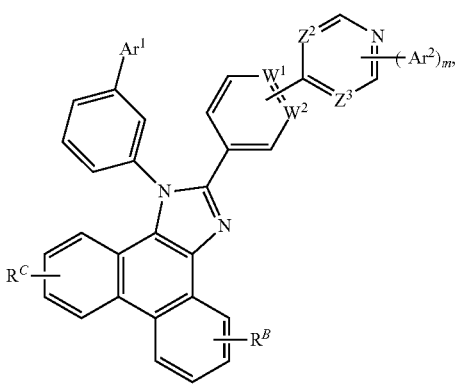

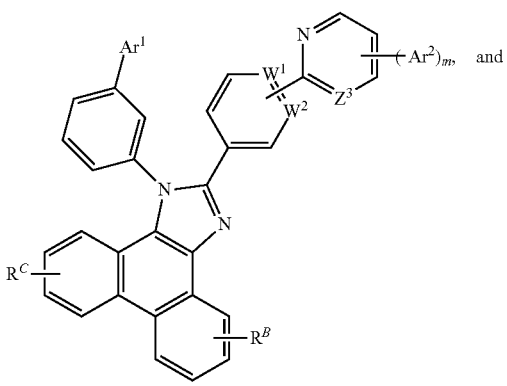

and

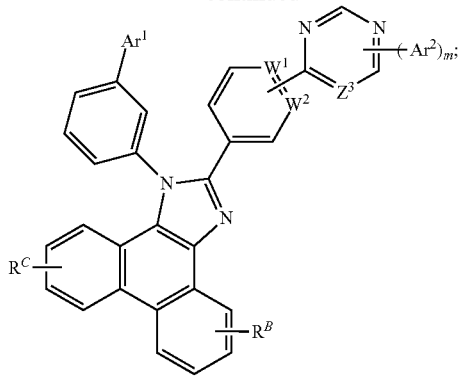

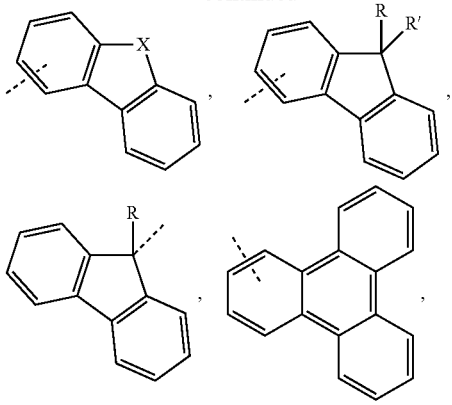

wherein m is 0 or 1, and Ar² is aryl or heteroaryl, each of which is optionally substituted.

17. The OLED of claim 1, wherein Ar¹ and $R^A$ are independently selected from the group consisting of

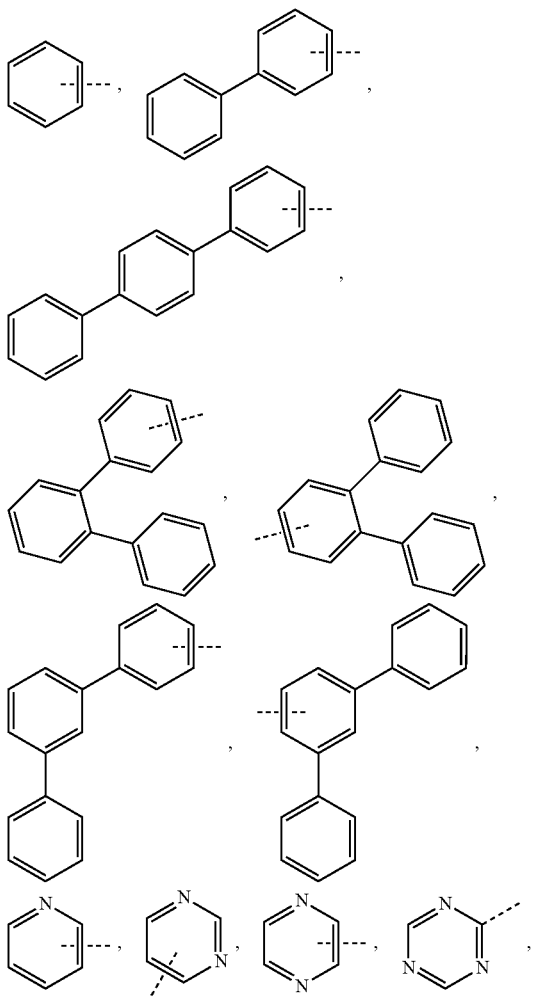

and combinations thereof, or any one aza variant thereof,
wherein X is selected from O, S, or Se;
R, R', and R" are independently selected from the group consisting of hydrogen, deuterium, alkyl, cycloalkyl, heteroalkyl, amino, silyl, alkynyl, aryl, heteroaryl, and combinations thereof; and
the dotted line represents attachment to Formula I.

* * * * *